(12) United States Patent
Zhang et al.

(10) Patent No.: US 10,987,336 B2
(45) Date of Patent: *Apr. 27, 2021

(54) METHOD OF PREVENTING OR TREATING SIDE EFFECT OF TUMOR THERAPY

(71) Applicant: ONQUALITY PHARMACEUTICALS CHINA LTD., Shanghai (CN)

(72) Inventors: Shiyi Zhang, Shanghai (CN); Zhaoyu Wu, Shanghai (CN); Chao Liu, Shanghai (CN); Linan Yang, Shanghai (CN); Leying Chen, Shanghai (CN); Jie Luo, Shanghai (CN)

(73) Assignee: ONQUALITY PHARMACEUTICALS CHINA LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/855,677

(22) Filed: Apr. 22, 2020

(65) Prior Publication Data

US 2020/0253915 A1 Aug. 13, 2020

Related U.S. Application Data

(63) Continuation of application No. PCT/CN2019/082623, filed on Apr. 15, 2019.

(30) Foreign Application Priority Data

Apr. 16, 2018 (CN) .......................... 201810339975.5

(51) Int. Cl.
| | |
|---|---|
| *A61K 31/34* | (2006.01) |
| *A61P 17/00* | (2006.01) |
| *A61K 31/04* | (2006.01) |
| *A61K 45/06* | (2006.01) |
| *A61K 9/00* | (2006.01) |
| *A61K 9/06* | (2006.01) |

(52) U.S. Cl.
CPC .............. *A61K 31/34* (2013.01); *A61K 31/04* (2013.01); *A61P 17/00* (2018.01); *A61K 9/0014* (2013.01); *A61K 9/06* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,322,433 A | 3/1982 | Leslie et al. |
| 4,450,175 A | 5/1984 | Warshaw |
| 4,654,209 A | 3/1987 | Leslie et al. |
| 5,504,117 A | 4/1996 | Gorfine |
| 6,492,398 B1 | 12/2002 | Vyas |
| 6,620,818 B1 | 9/2003 | Davis |
| 6,780,849 B2 | 8/2004 | Herrmann et al. |
| 6,979,688 B2 | 12/2005 | Ford |
| 6,987,129 B2 | 1/2006 | Mak et al. |
| 7,402,557 B2 | 7/2008 | Miller et al. |
| 7,696,247 B2 | 4/2010 | Herrmann et al. |
| 8,729,056 B2 | 5/2014 | Ishizaka et al. |
| 8,784,408 B2 | 7/2014 | DeLand et al. |
| 8,795,263 B2 | 8/2014 | DeLand et al. |
| 9,271,956 B2 | 3/2016 | Auclair |
| 9,427,605 B2 | 8/2016 | Peters |
| 9,428,582 B2 | 8/2016 | Edvardsen et al. |
| 9,480,707 B2 | 11/2016 | Perricone |
| 9,700,579 B2 | 7/2017 | Ehrlich et al. |
| 10,583,111 B2 | 3/2020 | Zhang et al. |
| 2002/0049188 A1 | 4/2002 | Azarnoff et al. |
| 2003/0157037 A1 | 8/2003 | Bunger et al. |
| 2003/0203915 A1 | 10/2003 | Fang et al. |
| 2005/0215514 A1 | 9/2005 | Ford |
| 2006/0030622 A1 | 2/2006 | Mak et al. |
| 2007/0172847 A1 | 7/2007 | Bonavida et al. |
| 2008/0045909 A1 | 2/2008 | Fossel |
| 2009/0048219 A1 | 2/2009 | Garvey |
| 2009/0203050 A1 | 8/2009 | Bonavida et al. |
| 2010/0016446 A1 | 1/2010 | Gonda et al. |
| 2010/0166891 A1 | 7/2010 | Schmidt |

(Continued)

FOREIGN PATENT DOCUMENTS

| | | |
|---|---|---|
| CA | 2410990 C | 8/2011 |
| CN | 1292691 A | 4/2001 |

(Continued)

OTHER PUBLICATIONS

Marcus E. Carr, "Hand-foot Syndrome in a Patient with Multiple Fire Ant Stings", 2004, Southern Medical Journal, vol. 97, No. 7, pp. 707-709. (Year: 2004).*
Masabumi Shibuya, "VEGF-VEGFR Signals in Health and Disease", 2014, Biomolecules & Therapeutic, 22(1), pp. 1-9. (Year: 2014).*
Chris G. Adigun, "Adverse Drug Reactions of the Lower Extremities", 2016, Clin. Podiatr. Med. Surg., 33(3), pp. 397-408. (Year: 2016).*
Common Terminology Criteria for Adverse Events, 2017, version 5.0, U.S. Department of Health and Human Services, https://ctep.cancer.gov/protocoldevelopment/electronic_applications/docs/CTCAE_v5_Quick_Reference_8.x11.pdf. (Year: 2017).*

(Continued)

*Primary Examiner* — My-Chau T. Tran
(74) *Attorney, Agent, or Firm* — Choate, Hall & Stewart LLP; Brenda Herschbach Jarrell; Xiaodong Li

(57) ABSTRACT

The present application relates to use of a nitric oxide releasing agent in the preparation of a medicament for preventing or treating diseases or disorders associated with administration of a VEGFR inhibitor and/or VEGF inhibitor. The present application further provides a method for preventing or treating diseases or disorders associated with administration of a VEGFR inhibitor and/or VEGF inhibitor in a subject. The method comprise administering, to a subject in need, a prophylactically or therapeutically effective amount of the nitric oxide releasing agent.

30 Claims, 19 Drawing Sheets

(56) References Cited

U.S. PATENT DOCUMENTS

| | | |
|---|---|---|
| 2011/0077260 A1 | 3/2011 | Ford |
| 2011/0190244 A1 | 8/2011 | Zalcberg |
| 2011/0196353 A1 | 8/2011 | DeLand et al. |
| 2013/0045956 A1 | 2/2013 | Ishizaka et al. |
| 2013/0225690 A1 | 8/2013 | Perez-Soler et al. |
| 2014/0011820 A1 | 1/2014 | Rodemer |
| 2014/0051730 A1 | 2/2014 | Fariello et al. |
| 2014/0336268 A1 | 11/2014 | Salentine et al. |
| 2014/0369949 A1 | 12/2014 | Peters |
| 2015/0313896 A1 | 11/2015 | Bouvier et al. |
| 2015/0313901 A1 | 11/2015 | Ford |
| 2015/0335597 A1 | 11/2015 | Pui et al. |
| 2016/0039852 A1 | 2/2016 | Russell et al. |
| 2016/0074405 A1 | 3/2016 | Hurwitz |
| 2016/0101114 A1 | 4/2016 | Lacouture et al. |
| 2016/0151427 A1 | 6/2016 | Whitlock et al. |
| 2017/0216441 A1 | 8/2017 | Muni |
| 2017/0354649 A1 | 12/2017 | Wang et al. |
| 2019/0282536 A1 | 9/2019 | Zhang et al. |

FOREIGN PATENT DOCUMENTS

| | | |
|---|---|---|
| CN | 1355807 A | 6/2002 |
| CN | 1107499 C | 5/2003 |
| CN | 1139380 C | 2/2004 |
| CN | 1568943 A | 1/2005 |
| CN | 1267212 C | 8/2006 |
| CN | 101146556 A | 3/2008 |
| CN | 102458473 A | 5/2012 |
| CN | 102421436 B | 5/2014 |
| CN | 103446261 B | 4/2015 |
| CN | 204411249 U | 6/2015 |
| CN | 105381070 A | 3/2016 |
| CN | 106163280 A | 11/2016 |
| CN | 106535936 A | 3/2017 |
| CN | 106539924 A | 3/2017 |
| CN | 107158287 A | 9/2017 |
| CN | 107412455 A | 12/2017 |
| CN | 107617010 A | 1/2018 |
| EP | 2251688 A1 | 11/2010 |
| EP | 2368549 A1 | 9/2011 |
| EP | 2729174 A1 | 5/2014 |
| WO | WO-95/32715 A1 | 12/1995 |
| WO | WO-96/27372 A1 | 9/1996 |
| WO | WO-99/38506 A2 | 8/1999 |
| WO | WO-00/10559 A1 | 3/2000 |
| WO | WO-00/52013 A2 | 9/2000 |
| WO | WO-01/89572 A1 | 11/2001 |
| WO | WO-02/13982 A1 | 2/2002 |
| WO | WO-2006/100154 A1 | 9/2006 |
| WO | WO-2006/113479 A2 | 10/2006 |
| WO | WO-2009/100367 A2 | 8/2009 |
| WO | WO-2009/114745 A1 | 9/2009 |
| WO | WO-2010/011650 A1 | 1/2010 |
| WO | WO-2010/125143 A1 | 11/2010 |
| WO | WO-2010/148572 A1 | 12/2010 |
| WO | WO-2011/000218 A1 | 1/2011 |
| WO | WO-2011/022652 A1 | 2/2011 |
| WO | WO-2011/022680 A2 | 2/2011 |
| WO | WO-2011/047256 A1 | 4/2011 |
| WO | WO-2012/082976 A1 | 6/2012 |
| WO | WO-2012/153331 A2 | 11/2012 |
| WO | WO-2013/009535 A1 | 1/2013 |
| WO | WO-2013/029009 A1 | 2/2013 |
| WO | WO-2013/083695 A1 | 6/2013 |
| WO | WO-2013/085784 A1 | 6/2013 |
| WO | WO-2013/138075 A1 | 9/2013 |
| WO | WO-2013/157891 A1 | 10/2013 |
| WO | WO-2014/047140 A1 | 3/2014 |
| WO | WO-2014/134502 A1 | 9/2014 |
| WO | WO-2015/095640 A1 | 6/2015 |
| WO | WO-2015/182905 A1 | 12/2015 |
| WO | WO-2015/197524 A1 | 12/2015 |
| WO | WO-2016/022170 A1 | 2/2016 |
| WO | WO-2016/210230 A1 | 12/2016 |
| WO | WO-2017/009824 A1 | 1/2017 |
| WO | WO-2017/029647 A1 | 2/2017 |
| WO | WO-2017/154001 A1 | 9/2017 |
| WO | WO-2017/165440 A1 | 9/2017 |
| WO | WO-2017/223182 A1 | 12/2017 |
| WO | WO-2019/059246 A1 | 3/2019 |

OTHER PUBLICATIONS

Arriola, E. et al., Management of the adverse events of afatinib: a consensus of the recommendations of the Spanish expert panel, Future Oncol., 11(2): 267-277 (2015).

Aw, D. C-W. et al., Management of epidermal growth factor receptor tyrosine kinase inhibitor-related cutaneous and gastrointestinal toxicities, Asia-Pac J Clin Oncol., 14: 23-31. (2018).

BIDIL® (isosorbide dinitrate and hydralazine hydrochloride), Highlights of Prescribing Information, 11 pages (Revised Mar. 2019).

Califano, R. et al., Expert Consensus on the Management of Adverse Events from EGFR Tyrosine Kinase Inhibitors in the UK, Drugs, 75: 1335-1348 (2015).

Chu, C.-Y. et al., Taiwanese Dermatological Association consensus for the prevention and management of epidermal growth factor receptor tyrosine kinase inhibitor-related skin toxicities, Journal of the Formosan Medical Association, 116: 413-423 (2017).

Cubero, D. et al., Cutaneous side effects of molecularly therapies for the treatment of solid tumors, Drugs in Context, 7:212516 (2018).

dilatrate®-SR (isosorbide dinitrate), Drug Summary, 8 pages (Revised Oct. 2014).

Gomez, P. and Lacouture, M.E., Clinical Presentation and Management of Hand-Foot Skin Reaction Associated with Sorafenib in Combination with Cytotoxic Chemotherapy: Experience in Breast Cancer, The Oncologist, 16:1508-1519 (2011).

Hirsh, V., Managing treatment-related adverse events associated with EGFR tyrosine kinase inhibitors in advanced non-small-cell lung cancer, Current Oncology, 18(3): 126-138 (2011).

International Search Report for PCT/CN2019/082623, 7 pages (dated Jul. 19, 2019).

Isordil® Titradose™ (isosorbide dinitrate), Drug Summary, 8 pages (Revised Jan. 2015).

Kozuki, T., Skin problems and EGFR-tyrosine kinase inhibitor, Japanese Journal of Clinical Oncology, 46(4): 291-298 (2016).

Lacouture, M.E. et al., Clinical practice guidelines for the prevention and treatment of EGFR inhibitor-associated dermatologic toxicities, Support Care Cancer, 19: 1079-1095 (2011).

Li, J. et al., Chinese consensus on management of tyrosine kinase inhibitor-associated side effects in gastrointestinal stromal tumors, World J Gastroenterol., 24(46):5189-5202 (2018).

Meadows, K. et al., Treatment of Palmar Plantar Erythrodysesthesia (PPE) with Topical Sildenafil: A Pilot Study, Support Care Cancer, 23(5):1311-1319 (2015).

NITRO-BID, Savage Laboratories, Drug Summary, 2 pages (Revised Sep. 2011).

RECTIV® (nitroglycerin), Highlights of Prescribing Information, 4 pages (Revised Nov. 2016).

Schmidinger, M., Understanding and managing toxicities of vascular endothelial growth factor (VEGF) inhibitors, EJC Supp., 11(2):172-191 (2013).

Thatcher, N. et al., Expert Consensus on the Management of Erlotinib-Associated Cutaneous Toxicity in the U.K., The Oncologist, 14: 840-847 (2009).

Written Opinion for PCT/CN2019/082623, 7 pages (dated Jul. 19, 2019).

Zhang, Y-h. and Peng, S-x. Advances in the study of nitric oxide-donating drugs, Acta Pharmaceutica Sinica, 44(11): 1200-1210 (2009). English Abstract.

Chanprapaph, K. et al., Epidermal Growth Factor Receptor Inhibitors: A Review of Cutaneous Adverse Events and Management, Derma. Res. Pract., 8 pages (2014).

Chanprapaph, K. et al., Multikinase Inhibitor-Induced Hand-Foot Skin Reaction: A Review of Clinical Presentation, Pathogenesis, and Management, Am. J. Clin. Dermatol., 16 pages (2016).

(56) References Cited

OTHER PUBLICATIONS

Lacouture, M.E. et al., Dermatologic Toxicity Occurring During Anti-EGFR Monoclonal Inhibitor Therapy in Patients With Metastatic Colorectal Cancer: A Systematic Review, Clin. Color. Cancer, 17(2):85-96 (2018).

Lipworth, A.D. et al., Hand-Foot Syndrome (Hand-Foot Skin Reaction, Palmar-Plantar Erythrodysesthesia): Focus on Sorafenib and Sunitinib, Oncology, 77:257-271 (2009).

Yang, C.H. et al., Hand-foot skin reaction in patients treated with sorafenib: a clinicopathological study of cutaneous manifestationsdue to multitargeted kinase inhibitor therapy, Brit. Jrnl. Derma., 158:592-596 (2008).

* cited by examiner

METHOD OF PREVENTING OR TREATING SIDE EFFECT OF TUMOR THERAPY

INVENTION FIELD

The present application relates to treatment of diseases, for instance a method of preventing or treating diseases or disorder associated with administration of a VEGFR inhibitor and/or VEGF inhibitor.

BACKGROUND

Mutation or overexpression of vascular endothelial growth factor receptor (VEGFR) has been found to be associated with a variety of cancers, and patients suffering from such cancers can be treated by the therapy of inhibiting VEGFR and/or VEGF (e.g., administering a VEGFR inhibitor and/or VEGF inhibitor). However, this type of therapy commonly causes serious side effects, especially in skin, facial organs and gastrointestinal tract. The serious side effects caused by therapies of inhibiting VEGFR and/or VEGF will compromise the life quality of patients, reducing the compliance and resistance of patients, causing medicament withdrawal or underdosage of the VEGFR/VEGF inhibitor thereby adversely affecting the therapeutic effect, or even resulting in an accelerated development of diseases and shortened survival of patients.

There is no effective therapeutic regimen controlling the side effects associated with administration of a VEGFR inhibitor and/or VEGF inhibitor presently. Thus, there is an urgent need for a therapeutic regimen capable of controlling these side effects successfully.

SUMMARY OF THE INVENTION

The present application provides a method of preventing or treating disease or disorder associated with administration of a VEGFR inhibitor and/or VEGF inhibitor. In particular, the present application relates to a use of a nitric oxide releasing agent for preventing or treating a disease or disorder associated with administration of VEGFR inhibitor and/or VEGF inhibitor in a subject, that may effectively control the side effects caused by VEGFR inhibitor and/or VEGF inhibitor, such as, skin tissue disease or disorder associated with administration of said VEGFR inhibitor and/or VEGF inhibitor, facial organ disease or disorder associated with administration of said VEGFR inhibitor and/or VEGF inhibitor and/or gastrointestinal disease or disorder associated with administration of said VEGFR inhibitor and/or VEGF inhibitor, and the like.

Different from using higher dosage (such as, about 2%) of nitric oxide releasing agent (such as, nitroglycerin) used to prevent or treat angina, in this application, surprisingly, the dosage of nitric oxide releasing agent (such as, nitroglycerin) used may be as low as 0.5% or less, such as less than 0.4% less than 0.3%, less than 0.25%, less than 0.2%, less than 0.15%, or less than 0.1%, and is effective in preventing or treating side effects associated with tumor therapy, for instance, effective in preventing or treating disease or disorder associated with administration of a VEGFR inhibitor and/or VEGF inhibitor, for example, effective in preventing or treating skin tissue disease or disorder associated with administration of a VEGFR inhibitor and/or VEGF inhibitor, facial organ disease or disorder associated with administration of a VEGFR inhibitor and/or VEGF inhibitor and/or gastrointestinal disease or disorder associated with administration of a VEGFR inhibitor and/or VEGF inhibitor, and the like. Before the present application, nitric oxide releasing agent has not been used to treat the above disease or disorder.

In one aspect, the present application provides a use of a nitric oxide releasing agent in the preparation of a medicament. The medicament may be used for preventing or treating a disease or disorder associated with administration of the VEGFR inhibitor and/or VEGF inhibitor. For instance, the disease or disorder may be caused by administration of the VEGFR inhibitor and/or the VEGF inhibitor. In some embodiments, the VEGFR inhibitor or VEGF inhibitor is used for treating tumor. In some embodiments, the location of the disease or disorder is different from that of tumor. In some embodiments, the medicament is formulated to be suitable for topical administration. In some embodiments, the location of said topical administration is not a primary location of tumor or a potential metastasis site of tumor. In some embodiments, the concentration of the nitric oxide releasing agent in the medicament is about 0.0001% (w/w) to about 50% (w/w). In some embodiments, the medicament is formulated to be suitable for external administration. In some embodiments, the medicament is formulated as ointment. In some embodiments, the medicament further comprises one or more additional active ingredients. In some embodiments, the medicament does not substantially affect the therapeutic effect of the VEGFR inhibitor and/or the VEGF inhibitor (e.g., the effect of treating cancers).

In another aspect, the present application provides a nitric oxide releasing agent for preventing or treating a disease or disorder associated with administration of the VEGFR inhibitor and/or VEGF inhibitor in a subject. For instance, the disease or disorder may be caused by administration of a VEGFR inhibitor and/or the VEGF inhibitor.

In another aspect, the present application provides a method of preventing or treating a disease or disorder associated with administration of a VEGFR inhibitor and/or VEGF inhibitor in a subject, comprising a prophylactically or therapeutically effective amount of the nitric oxide releasing agent administering to the subject. In some embodiments, the subject comprises a human or non-human animal. For instance, the non-human animal may comprise an animal selected from the group consisting of monkey, chicken, goose, cat, dog, mouse, and rat. In some embodiments, the subject may comprise cancer subject. In some embodiments, the subject was, is and/or will be administrated the VEGFR inhibitor or VEGF inhibitor. In some embodiments, the subject suffers or susceptible to suffer said disease or disorder associated with administration of a VEGFR inhibitor and/or VEGF inhibitor. In some embodiments, the severity of the disease or disorder increase after administrating the VEGFR inhibitor and/or VEGF inhibitor. In some embodiments, the subject has not suffered the disease or disorder before administrating the VEGFR inhibitor or VEGF inhibitor. In some embodiments, the VEGFR inhibitor and/or VEGF inhibitor doesn't comprise the nitric oxide releasing agent. In some embodiments, the VEGFR inhibitor and/or VEGF inhibitor doesn't comprise a nitroglycerin. In some embodiments, the disease or disorder is caused by administration of the VEGFR inhibitor and/or the VEGF inhibitor to the subject. For instance, the nitric oxide releasing agent may be administered before, simultaneously with, or after the administration of the VEGFR inhibitor and/or the VEGF inhibitor to the subject. In some embodiments, the VEGFR inhibitor and/or the VEGF inhibitor is used to treating tumor. In some embodiments, the location of the disease or disorder is different from that of tumor. In some embodiments, the nitric oxide releasing agent is topically administered. In some embodiments, the location of said topical administration is not a primary location of tumor or a potential metastasis site of tumor. In some embodiments, the nitric oxide releasing agent is administered at a concentration of about 0.0001% (w/w) to about 50% (w/w). In some embodiments, the nitric oxide releasing agent is external administered. In some embodiments, the nitric oxide releasing agent is contained in an ointment for administration. In some embodiments, the nitric oxide releasing agent is administered together with one or more additional active ingredients. In some embodiments, the administration of the nitric oxide releasing agent does not substantially affect the therapeutic effect of the VEGFR inhibitor and/or the VEGF inhibitor.

In another aspect, the present application provides a combination of medicaments or kit. The combination of medicaments or kit may comprise: 1) a VEGFR inhibitor and/or a VEGF inhibitor; and 2) a nitric oxide releasing agent. In some embodiments, the VEGFR inhibitor and/or the VEGF inhibitor and the nitric oxide releasing agent are not mixed with each other. In some embodiments, the VEGFR inhibitor and/or the VEGF inhibitor and the nitric oxide releasing agent are each independently present in a separate container. In some embodiments, the nitric oxide releasing agent is formulated to be suitable for external administration. In some embodiments, the nitric oxide releasing agent is formulated as ointment. In some embodiments, the concentration of the nitric oxide releasing agent is about 0.0001% (w/w) to about 50% (w/w). In some embodiments, the nitric oxide releasing agent of 2) is capable of preventing or treating the diseases or disorders caused by the VEGFR inhibitor and/or the VEGF inhibitor of 1). In some embodiments, the nitric oxide releasing agent of 2) does not substantially affect the therapeutic effect of the VEGFR inhibitor and/or the VEGF inhibitor of 1). In some embodiments, the nitric oxide releasing agent of 2) is administered before, simultaneously with, or after the administration of the VEGFR inhibitor and/or the VEGF inhibitor of 1).

In another aspect, the present application provides a method comprising administrating nitric oxide releasing agent to a subject, wherein the subject was, is and/or will be administrated with VEGFR inhibitor and/or VEGF inhibitor, and suffer or is susceptible to suffer a disease or disorder associated with administration of VEGFR inhibitor and/or VEGF inhibitor.

In another aspect, the present application provides a method of preventing or treating a disease or disorder, comprising administrating nitric oxide releasing agent to a subject, wherein the subject was, is and/or will be administrated a VEGFR inhibitor and/or VEGF inhibitor.

In another aspect, the present application provides a method of preventing or treating a disease or disorder, comprising administrating a nitric oxide releasing agent to a subject that is susceptible to suffer or suffers the disease or disorder, wherein said disease or disorder is hand-foot syndrome.

In some embodiments, the subject was, is and/or will be administrated a VEGFR inhibitor and/or VEGF inhibitor.

In another aspect, the present application provides a method comprising the steps of: 1) monitoring one or more features of skin tissue, facial organ and/or gastrointestinal tract of a subject administrated a VEGFR inhibitor and/or VEGF inhibitor; 2) when the monitoring shows the subject suffering skin tissue disease or disorder, facial organ disease or disorder and/or gastrointestinal disease or disorder associated with administration of the VEGFR inhibitor and/or VEGF inhibitor, administrating the nitric oxide releasing agent to the subject.

In some embodiments, the method further comprises continuously monitoring the skin tissue disease or disorder, facial organ disease or disorder and/or gastrointestinal tract disease or disorder, and reducing or withdrawing the VEGFR inhibitor and/or VEGF inhibitor optionally.

In some embodiments, the severity of the disease or disorder increases after the administration of the VEGFR inhibitor and/or VEGF inhibitor.

In some embodiments, the subject has not suffered the disease or disorder before the administration the VEGFR inhibitor and/or VEGF inhibitor.

In some embodiments, the VEGFR inhibitor and/or VEGF inhibitor doesn't comprise the nitric oxide releasing agent. In some embodiments, the VEGFR inhibitor and/or VEGF inhibitor doesn't comprise a nitroglycerin.

In some embodiments, the disease or disorder is an epithelial disease or disorder.

In some embodiments, the administration of the VEGFR inhibitor and/or VEGF inhibitor is used to treat cancer. In some embodiments, the location of said disease or disorder is different from that of cancer.

In some embodiments, the subject is topically administrated the nitric oxide releasing agent.

In some embodiments, the subject is topically administrated the nitric oxide releasing agent at location of disease or disorder that substantially doesn't comprise a tumor cell. In some embodiments, administrate the nitric oxide releasing agent to the subject at no-cancer location.

In some embodiments, the at least one of the VEGFR inhibitors as described in the present application directly effects on a VEGFR protein and/or a nucleic acid encoding a VEGFR protein.

In some embodiments, the at least one of the VEGF inhibitors as described in the present application directly effects on a VEGF protein and/or a nucleic acid encoding a VEGF protein.

In some embodiments, the VEGFR inhibitor of the present application and/or the VEGF inhibitor of the present application is used for treating cancers.

In some embodiments, the VEGFR inhibitor of the present application comprises a small molecular VEGFR inhibitor, a protein macromolecule specifically binding to VEGFR, an RNAi inhibiting the expression of a VEGFR protein and/or an antisense oligonucleotide inhibiting the expression of a VEGFR protein.

In some embodiments, the VEGF inhibitor of the present application comprises a VEGF trapping agent and/or an agent of reducing the expression level of VEGF.

In some embodiments, the VEGFR inhibitor of the present application inhibits VEGFR1, VEGFR2 and/or VEGFR3.

In some embodiments, the VEGFR inhibitor and/or VEGF inhibitor of the present application comprises Ramucirumab, Bevacizumab, Regorafenib, Ponatinib, Cabozantinib, Lenvatinib, Sorafenib, Pazopanib, Apatinib, Axitinib, Nintedanib, Vandetanib, Sunitinib, Midostaurin, Tivozanib, Fruquintinib, Cediranib, Brivanib, Donafenib, Sulfatinib, Anlotinib, Famitinib, Tesevatinib, Vorolanib, Motesanib, Linifanib, Semaxanib, Dovitinib, Orantinib, Vatalanib, Telatinib, Glesatinib, Delitinib, Ilorasertib, Rebastinib, Golvatinib, Foretinib, Ningetinib, Tafetinib, Altiratinib, TAS-115, Chiauranib, Henatinib, 4SC-203, AAL-993, ACTB-1003, AEE-788, AMG-628, Arenobufagin, BAW2881, BIBF-1202, BMS-690514, BMS-794833, CEP-11981, CEP-5214, CP-547632, CYC116, DW532, ENMD-2076, FIIN-1, GFB-204, BFH-772, BMS599626, BMS690514, PP 121, MGCD 265 analogue, AC480, Ki 8751, KRN 633, WHI-P 154, TAK593, JI 101, AZD-2932, SCR-1481B1, Isoliquiritigenin, JNJ-26483327, KI-20227, LY2457546, ODM-203, OSI-930, PF-00337210, CGP41231, R1530, RAF265, SAR131675, Semaxinib, SIM010603, SKLB1002, SKLB610, SU 5205, SU11652, SU14813, SU-1498, SU-4312, SU5402, T-1840383, Tanshinone IIA, TAS-115, TG 100572, TG 100801, TG100572 HCl, Toceranib, Tyrosine phosphorylation inhibitor A9, Tesevatinib, XL-844, XL999, ZD4190 HCl, ZM-306416, ZM323881 HCl, ABT-510, NVP-ACC789, ADT-OH, BMS-645737, EG 00229, XL-820, SGI-7079, Endostatin, Taxifolin, Aflibercept, a pharmaceutically acceptable salt thereof and/or any combination of the foregoing.

In some embodiments, the VEGFR inhibitor and/or VEGF inhibitor of the present application is administered in combination with one or more additional therapies. The one or more additional therapies may comprise one or more additional anti-tumor therapies.

In some embodiments, the disease or disorder of the present application is caused by the VEGFR and/or VEGF inhibition.

In some embodiments, the disease or disorder of the present application comprises skin tissue disease or disorder, facial organ disease or disorder, and/or gastrointestinal disease or disorder associated with administration of the VEGFR inhibitor and/or VEGF inhibitor.

In some embodiments, the skin tissue disease or disorder, facial organ disease or disorder and/or gastrointestinal disease or disorder associated with administration of the VEGFR inhibitor and/or VEGF inhibitor of the present application comprises epithelial disease or disorder associated with administration of the VEGFR inhibitor and/or VEGF inhibitor in the skin tissue, the facial organ and/or the gastrointestinal tract.

In some embodiments, the epithelial disease or disorder associated with administration of the VEGFR inhibitor and/or VEGF inhibitor of the present application comprises the disease or disorder associated with lesion of endothelial cell and/or disease or disorder associated with lesion of epithelial cell, and wherein the lesion of endothelial cell and/or the lesion of epithelial cell is associated with administration of a VEGFR inhibitor and/or VEGF inhibitor. The endothelial cell may comprise vascular endothelial cell. The epithelial cell may comprise skin epithelial cell, oral epithelial cell, nasal epithelial cell, gastric epithelial cell and/or intestinal epithelial cell.

In some embodiments, the disease or disorder associated with administration of the VEGFR inhibitor and/or VEGF inhibitor selected from the group consisting of rash associated with administration of the VEGFR inhibitor and/or VEGF inhibitor, hand-foot syndrome associated with administration of the VEGFR inhibitor and/or VEGF inhibitor, pruritus associated with administration of the VEGFR inhibitor and/or VEGF inhibitor, erythema associated with administration of the VEGFR inhibitor and/or VEGF inhibitor, xerosis cutis associated with administration of the VEGFR inhibitor and/or VEGF inhibitor, alopecia associated with administration of the VEGFR inhibitor and/or VEGF inhibitor, paronychia associated with administration of the VEGFR inhibitor and/or VEGF inhibitor, pigmentation disorder associated with administration of the VEGFR inhibitor and/or VEGF inhibitor, oral mucositis associated with administration of the VEGFR inhibitor and/or VEGF inhibitor, xerostomia associated with administration of the VEGFR inhibitor and/or VEGF inhibitor, epistaxis associated with administration of the VEGFR inhibitor and/or VEGF inhibitor, nasopharyngitis associated with administration of the VEGFR inhibitor and/or VEGF inhibitor, cheilitis associated with administration of the VEGFR inhibitor and/or VEGF inhibitor, esophagitis associated with administration of the VEGFR inhibitor and/or VEGF inhibitor, esogastritis associated with administration of the VEGFR inhibitor and/or VEGF inhibitor, gastric ulcer associated with administration of the VEGFR inhibitor and/or VEGF inhibitor, diarrhea associated with administration of the VEGFR inhibitor and/or VEGF inhibitor, vomiting associated with administration of the VEGFR inhibitor and/or VEGF inhibitor, nausea associated with administration of the VEGFR inhibitor and/or VEGF inhibitor, anorexia associated with administration of the VEGFR inhibitor and/or VEGF inhibitor, constipation associated with administration of the VEGFR inhibitor and/or VEGF inhibitor, and/or abdominal pain associated with administration of the VEGFR inhibitor and/or VEGF inhibitor. In some embodiments, the disease or disorder associated with administration of the VEGFR inhibitor and/or VEGF inhibitor comprises hand-foot syndrome associated with administration of the VEGFR inhibitor and/or VEGF inhibitor. In some embodiments, the severity of the disease or disorder associated with administration of the VEGFR inhibitor and/or VEGF inhibitor is Grade 1 or above, Grade 2 or above, Grade 3 or above, Grade 4 or above, and/or Grade 5 or above according to NCI-CTCAE V5.0.

In some embodiments, the nitric oxide releasing agent is capable of producing a substance selected from the group consisting of $NO^+$, $NO^-$, $N_2O$, $NO$, $N_2O_3$, $NO_2$, $NO_3^-$ and $NO_2^-$. For instance, the nitric oxide releasing agent is capable of directly or indirectly producing NO. in some embodiments, the nitric oxide releasing agent comprise NO.

In some embodiments, the nitric oxide releasing agent comprises a substance comprises an organic molecule, an inorganic molecule, a macromolecule, a nanomaterial, and/or an ammonia oxidizing microorganism (AOM).

In some embodiments, the nitric oxide releasing agent comprises an organic molecule, and said organic molecule comprises nitroglycerin, isosorbide mononitrate, pentaerythritol tetranitrate, isosorbide dinitrate, trolnitrate, Nicorandil, propatyl nitrate, Molsidomine, 5-amino-3-(4-morpholinyl)-1,2,3-oxadiazole, isoamyl nitrite, 3,3-di(aminoethyl)-1-hydroxyl-2-carbonyl-1-triazene (NOC-18), sulfo nucleophilic complex disodium salt, S-nitrosoglutathione, S-nitroso-N-acetypenicillamine, 4-phenyl-3-furonitrile, (±)-(E)-4-Ethyl-2-[(E)-hydroxyimino]-5-nitro-3-hexenamide, Streptozocin, NG-Hydroxy-L-arginine acetate salt, $O_2$-(2,4-Dinitrophenyl) 1-[(4-ethoxycarbonyl)piperazin-1-yl]-diolate, N-nitrosodibutylamine, 3-morpholinosydnonimine, Linsidomine, 3-(4-acetylphenyl) sydnone, diethylamino nucleophilic complex/AM and/or Itramin. For instance, the organic molecule may be selected from the group consisting of nitroglycerin, isosorbide mononitrate, isosorbide dinitrate and any combination thereof. In some embodiment, the nitric oxide releasing agent comprises organic molecule, and the organic molecule comprises nitroglycerin.

In some embodiments, the nitric oxide releasing agent comprises an inorganic molecule, and the inorganic molecule comprises nitryl complex, nitrosyl complex, metal nitrosamino complex, nitrate, and/or nitrite. In some embodiments, the nitric oxide releasing agent comprises an inorganic molecule, and the inorganic molecule comprises sodium nitroprusside.

In some embodiments, the nitric oxide releasing agent comprises ammonia oxidizing microorganism (AOM), and the ammonia oxidizing microorganism (AOM) comprises ammonia oxidizing bacteria (AOB). In some embodiments, the nitric oxide releasing agent comprises ammonia oxidizing microorganism (AOM), and said ammonia oxidizing microorganism (AOM) comprises *Nitrosomonas, Nitrosococcus Nitrosospira, Nitrosocystis, Nitrosolobus* and/or *Nitrosovibrio*.

In some embodiments, the nitric oxide releasing agent has a relative molecular weight of 2000 Daltons or below, 1500 Daltons or below, 1200 Daltons or below, 1000 Daltons or below, 900 Daltons or below, 800 Daltons or below, 700 Daltons or below, 600 Daltons or below, 500 Daltons or below, 400 Daltons or below, 300 Daltons or below, 200 Daltons or below, or 100 Daltons or below.

In some embodiments, the nitric oxide releasing agent comprises a macromolecule or a nanomaterial, and the macromolecule or nanomaterial comprises S-nitrosothiol silica nanospheres, S-nitrosoethanedithiol chitin, and/or oligopropylenediamine-grafted chitosan NONOate.

In some embodiments, the nitric oxide releasing agent has one or more groups as following: diazeniumdiolate, hydroxyldiazenesulfonic acid, S-nitrosothiol, furoxan, oxime, N-nitrosoamine, N-hydroxylguanidine, nitrate, nitrite, nitrate ester, nitrite ester, sydnonimine, sydnone, oxatriazol-5-imine, oxatriazol-5-one, hydroxylamine, dioxadiazacyclobutene, N-hydroxylnitrosoamine, N-nitrosoimine, hydroxyurea and metal nitrosamino complex.

Persons skilled in the art can recognize other aspects and advantages of this disclosure from the detailed description hereinafter. The following detailed description only reveals and describes exemplary embodiments of this disclosure. As those skilled in the art will recognize, this disclosure enables persons skilled in the art to modify the disclosed embodiments without departing the spirit and scope of the present application. Correspondingly, the drawings and the description in the present specification are only illustrative, but not limitative.

BRIEF DESCRIPTION OF DRAWINGS

The features of the invention as claimed in the present application are defined by the accompanying claims. The features and advantages of the inventions as disclosed herein can be better understood by referring to the exemplary embodiments and the accompanying drawings. The drawings are briefly described as follows:

DETAILED DESCRIPTION

Figure 1:
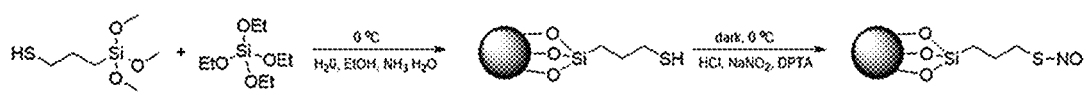
FIG. 1 depicts an exemplary synthesis scheme of S-nitrosothiol silica nanospheres.
Figure 2:
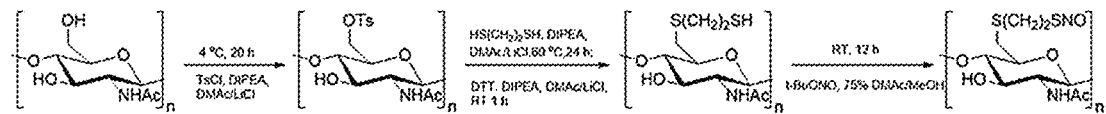
FIG. 2 depicts an exemplary synthesis scheme of S-nitrosoethanedithiol chitin.
Figure 3:
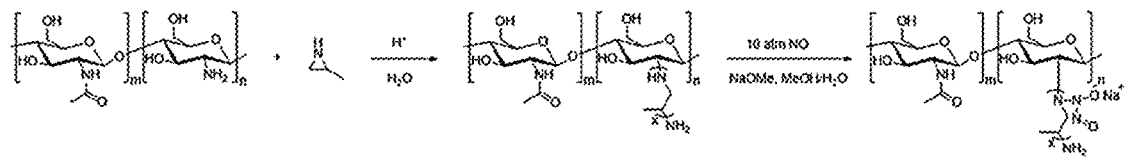
FIG. 3 depicts an exemplary synthesis scheme of oligopropylenediamine-grafted chitosan NONOate.

The embodiments of the present application are described hereinafter by means of specific examples. Persons skilled in the art can readily understand the other advantages and effects of the inventions as described herein from the disclosure of the present specification.

VEGFR inhibitor and/or VEGF Inhibitor

As used herein, the term "VEGFR" generally refers to Vascular Endothelial Growth Factor Receptor which belongs to the Receptor tyrosine kinases (RTKs) family. It comprises primarily three subtypes, including VEGFR1, VEGFR2, and VEGFR3 as reported. Of those, VEGFR1, and VEGFR2 are primarily distributed on the surface of tumor vascular endothelium, regulating the tumor angiogenesis; and VEGFR3s is primarily distributed on the surface of lymph endothelium, regulating the tumor lymphangiogenesis. It is reported that VEGFR2s is the primary VEGF signal transduction receptors during the angiogenesis and mitosis processes. The VEGF family comprises primarily VEGF-A, VEGF-B, VEGF-C, VEGF-D, VEGF-E and placental growth factor (PGF). VEGF-A in combination with VEGFR-1 and VEGFR-2 can regulate almost all the cell responses to VEGF as reported. The activation of VEGFR-2 in endothelial cells results in increased proliferation, migration, survival and improved vascular permeability (see, Waldner, Maximilian J. et al., the Journal of Experimental Medicine 207.13, 2010). The expression of VEGFR or the increased kinase activity thereof is associated with a series of human cancers.

As used herein, the term "VEGF" generally refers to Vascular Endothelial Growth Factor which is known as the specific growth factor of the key endothelial cells required by pathological angiogenesis signal pathway according to reports. The inhibition of VEGF receptor tyrosine kinase signal pathway blocks the angiogenesis during the growth of tumors, resulting in stagnation or regression of angiogenic tumors (see, Gerald McMahon, the Oncologist 2000, 5:3-10).

As used herein, the term "VEGFR inhibitor" generally refers to any substance or agent capable of causing the decreased expression, quantity or activity of VEGFR which is known in the art or may be discovered in the future, comprising any substance which may cause an inhibition of biological activity associated with VEGFR activity when the substance or agent is administered to a subject (including an inhibition of downstream biological effect produced by combination of any VEGFR with its natural ligand). In some embodiments, the VEGFR inhibitor may comprise any agent capable of blocking the VEGFR activity or any downstream biological effect thereof during the treatment of cancers. For instance, the VEGFR inhibitor may be used to treat tumors. For instance, the VEGFR inhibitor may inhibit one or more functions of VEGFR directly. For instance, the VEGFR inhibitor may combine with a nucleic acid sequence encoding VEGFR. For instance, the VEGFR inhibitor may reduce the transcription level of VEGFR protein.

As used herein, the term "VEGF inhibitor" generally refers to any substance or agent capable of causing the decreased expression, quantity or activity of VEGF which is known in the art or may be discovered in the future, comprising any substance which may cause an inhibition of biological activity associated with VEGF activity when the substance or agent is administered to a subject. In some embodiments, the VEGF inhibitor may comprise any agent capable of blocking the VEGF activity or any downstream biological effect thereof during the treatment of cancers. For instance, the VEGF inhibitor may be used to treat tumors. For instance, the VEGF inhibitor may inhibit one or more functions of VEGF directly. For instance, the VEGF inhibitor may combine with a nucleic acid sequence encoding VEGF. For instance, the VEGFR inhibitor may reduce the transcription level of VEGF protein.

As used herein, whatever in vitro or in vivo, the method of detecting and/or evaluating the inhibition level of the VEGF and/or VEGFR is normal in the art. And the method may be used in verify, standardize, screen and/or evaluate the VEGF inhibitor and/or VEGFR inhibitor of the present application.

As used herein, the term "disease or disorder associated with administration of a VEGFR inhibitor and/or VEGF inhibitor" generally refers to disease or disorder related to administrate VEGFR inhibitor and/or VEGF inhibitor to a subject. For instance, the disease or disorder may be disease or disorder caused by administrating VEGFR inhibitor and/or VEGF inhibitor to a subject. For instance, the disease or disorder may comprise skin tissue disease or disorder associated with administration of the VEGFR inhibitor and/or VEGF inhibitor, facial organ disease or disorder associated with administration of the VEGFR inhibitor and/or VEGF inhibitor, and/or gastrointestinal disease or disorder associated with administration of the VEGFR inhibitor and/or VEGF inhibitor. For instance, the disease or disorder may comprise rash associated with administration of the VEGFR inhibitor and/or VEGF inhibitor, hand-foot syndrome associated with administration of the VEGFR inhibitor and/or VEGF inhibitor, pruritus associated with administration of the VEGFR inhibitor and/or VEGF inhibitor, erythema associated with administration of the VEGFR inhibitor and/or VEGF inhibitor, xerosis cutis associated with administration of the VEGFR inhibitor and/or VEGF inhibitor, alopecia associated with administration of the VEGFR inhibitor and/or VEGF inhibitor, paronychia associated with administration of the VEGFR inhibitor and/or VEGF inhibitor, pigmentation disorder associated with administration of the VEGFR inhibitor and/or VEGF inhibitor, oral mucositis associated with administration of the VEGFR inhibitor and/or VEGF inhibitor, xerostomia associated with administration of the VEGFR inhibitor and/or VEGF inhibitor, epistaxis associated with administration of the VEGFR inhibitor and/or VEGF inhibitor, nasopharyngitis associated with administration of the VEGFR inhibitor and/or VEGF inhibitor, cheilitis associated with administration of the VEGFR inhibitor and/or VEGF inhibitor, esophagitis associated with administration of the VEGFR inhibitor and/or VEGF inhibitor, gastric ulcer associated with administration of the VEGFR inhibitor and/or VEGF inhibitor, diarrhea associated with administration of the VEGFR inhibitor and/or VEGF inhibitor, vomiting associated with administration of the VEGFR inhibitor and/or VEGF inhibitor, nausea associated with administration of the VEGFR inhibitor and/or VEGF inhibitor, anorexia associated with administration of the VEGFR inhibitor and/or VEGF inhibitor, constipation associated with administration of the VEGFR inhibitor and/or VEGF inhibitor, and/or abdominal pain associated with administration of the VEGFR inhibitor and/or VEGF inhibitor. In present application, the disease or disorder associated with administration of the VEGFR inhibitor and/or VEGF inhibitor may be hand-foot syndrome associated with administration of the VEGFR inhibitor and/or VEGF inhibitor.

As used herein, the term "tumor" generally refers to neoformation formed by local tissue cell proliferation under the action of various tumorigenic factors, which is also known as neoplasm. According to the cellular properties of the neoformation and the harm extent to an organism, the tumors are in turn classified to two types, i.e., benign tumors and malignant tumors, and cancer is a general term for malignant tumors. The tumors may be selected from the group consisting of malignant epithelial malignant tumors (epithelium-derived cancers), lung cancer (e.g., non-small cell lung cancer), breast cancer, skin cancer, bladder cancer, colon cancer, bowel cancer, prostate cancer, pancreas cancer, uterine cancer, cervical cancer, ovarian cancer, esophagus cancer, head and neck cancer, stomach cancer and laryngeal cancer. For instance, the tumor may be liver cancer, kidney cancer, colorectal cancer, stomach cancer, esophageal cancer or thyroid cancer.

As used herein, the VEGFR inhibitor and/or the VEGF inhibitor may be identified or screened by a method known in the art, e.g., by detecting the change of expression or activity of VEGFR and/or VEGF after administration of the candidate substance/agent. The expression of VEGFR and/or VEGF may also be detected by a method known in the prior art, e.g., an immunohistochemical method, PCR, RT-PCR, in-situ hybridization, Southern blot, Western blot, Northern blot, spectrophotometry, and ELISA, and the like.

As used herein, at least one (e.g., at least 1, at least 2, at least 3, at least 4, at least 5, at least 6, at least 7, at least 8, at least 9, at least 10, or more) of the VEGFR inhibitor may directly act on a VEGFR protein and/or a nucleic acid encoding a VEGFR protein.

As used herein, at least one (e.g., at least 1, at least 2, at least 3, at least 4, at least 5, at least 6, at least 7, at least 8, at least 9, at least 10, or more) of the VEGF inhibitor may directly act on a VEGF protein and/or a nucleic acid encoding a VEGF protein.

For instance, the VEGFR inhibitor may comprise a small molecular VEGFR inhibitor, a protein macromolecule specifically binding to VEGFR, an RNAi inhibiting the expression of a VEGFR protein and/or an antisense oligonucleotide inhibiting the expression of VEGFR protein.

As used herein, the term "small molecular VEGFR inhibitor" may comprise a small molecular VEGFR inhibitor reversibly or irreversibly binding to VEGFR or a small molecular VEGFR inhibitor specifically binding to a mutant VEGFR. For instance, the small molecular VEGFR inhibitor may comprise Regorafenib, Ponatinib, Cabozantinib, Lenvatinib, Sorafenib, Apatinib, Axitinib, Nintedanib, Vandetanib, Sunitinib, Midostaurin, Tivozanib, Fruquintinib, Cediranib, Brivanib, Donafenib, Sulfatinib, Anlotinib, Famitinib, Tesevatinib, Vorolanib, Motesanib, Linifanib, Semaxanib, Dovitinib, Orantinib, Vatalanib, Telatinib, Glesatinib, Lucitanib, Ilorasertib, Rebastinib, Golvatinib, Foretinib, Ningetinib, Tafetinib, Altiratinib, TAS-115, Chiauranib, Henatinib, 4SC-203, AAL-993, ACTB-1003, AEE-788, AMG-628, Arenobufagin, BAW2881, BIBF-1202, BMS-690514, BMS-794833, CEP-11981, CEP-5214, CP-547632, CYC116, DW532, ENMD-2076, FIIN-1, GFB-204, BFH-772, BMS599626, BMS690514, PP 121, MGCD 265 analogue, AC480, Ki 8751, KRN 633, WHI-P 154, TAK593, JI 101, AZD-2932, SCR-1481B1, Isoliquiritigenin, JNJ-26483327, KI-20227, LY2457546, ODM-203, OSI-930, PF-00337210, CGP41231, R1530, RAF265, SAR131675, Semaxinib, SIM010603, SKLB1002, SKLB610, SU 5205, SU11652, SU14813, SU-1498, SU-4312, SU5402, T-1840383, Tanshinone IIA, TAS-115, TG 100572, TG 100801, TG100572 HCl, Toceranib, Tyrosine phosphorylation inhibitor A9, Tesevatinib, XL-844, XL999, ZD4190 HCl, ZM-306416, ZM323881 HCl, ABT-510, NVP-ACC789, ADT-OH, BMS-645737, EG 00229, XL-820, SGI-7079, Endostatin and/or Taxifolin.

As used herein, the term "specifically binding" generally means that in a complicated mixture, the VEGFR inhibitor may specifically recognize and bind to VEGFR, but does not substantially recognize or bind to other components in the complicated mixture. For instance, the affinity of the inhibitor to VEGFR may be at least 2 times the affinity of the inhibitor to other non-specific binding ingredients (e.g., at least 2 times, 3 times, 4 times, 5 times, 6 times, 7 times, 8 times, 9 times, 10 times or more). In some embodiments, the equilibrium dissociate constant of the VEGFR inhibitor with VEGFR is less than or equal to $10^{-6}$ (e.g., less than or equal to $10^{-7}M$, less than or equal to $10^{-8}M$, less than or equal to $10^{-9}M$, less than or equal to $10^{-10}$ M or less).

As used herein, the protein macromolecule that specifically binds to VEGFR may be an antibody, the antibody variant, fusion protein, derivative or a fragment thereof that targets VEGFR. For instance, it may be an antibody that specifically binds to VEGFR or a fragment of antigen binding thereof.

As used herein, the antibody generally refers to a polypeptide molecule capable of specifically recognizing and/or neutralizing a specific antigen. For instance, the antibody may comprise an immunoglobulin composed of at least two heavy (H) chains and two light (L) chains that are linked to each other via disulfide bond, and comprise any molecule containing an antigen binding fraction thereof. The term "antibody" may comprise a monoclonal antibody, an antibody fragment or an antibody derivative, including, but not limited to, a human antibody (full humanized antibody), a humanized antibody, a chimeric antibody, a single-stranded antibody (e.g., scFv), and an antibody fragment binding to an antigen (e.g., Fab, Fab' and $(Fab)_2$ fragment). Of those, the chimeric antibody may be an antibody in which a part of the amino acid sequence of each heavy chain or light chain is homologous to the corresponding amino acid sequence of an antibody derived from a species, or belongs to a particular classification, while the remainder segment of the chain is homologous to the corresponding sequence of another species. Of those, the humanized antibody may refer to a chimeric antibody which comprise a small amount of sequence derived from a non-human immunoglobulin, thereby decreasing the immunogenicity when a heteroantibody is introduced into humans, but keeping a complete antigen binding affinity and specificity of the antibody. Of those, the full humanized antibody may comprise antibody produced by human or human immune cells, or derived from a non-human source (e.g., a genetically modified non-human animal by using a humanized antibody library), or other sequences encoding a human antibody.

As used herein, the fragment of antigen binding of an antibody may be one or more fragments having a specific antigen binding function. The antigen binding function of an antibody may be achieved by a full-length fragment of the antibody. The antigen binding function of the antibody may also be achieved by means of: a heavy chain containing Fv, ScFv, dsFv, Fab, Fab' or F(ab')₂ fragment, or a light chain containing Fv, ScFv, dsFv, Fab, Fab' or F(ab')₂ fragment. (1) Fab fragment, that is a monovalent fragment composed of VL, VH, CL and CH domains; (2) F(ab')₂ fragment, that is a divalent fragment containing two Fab fragments linked by a disulfide bond in the hinge region; (3) Fd fragment composed of VH and CH domains; (4) Fv fragment composed of VL and VH domains of one arm of the antibody; (5) dAb fragment composed of VH domain (Ward et al., (1989) Nature 341: 544-546); (6) isolated complementary determining region (CDR); (7) a combination of two or more isolated CDRs that may be optionally linked via a linker; (8) Camelized single domain antibody, that is an antibody comprising two heavy chain variable regions but not containing light chain and (9) nanobody, comprising a heavy chain variable region, CH2 and CH3. Moreover, it may further comprise monovalent single-stranded molecule Fv (scFv) formed by pairing VL and VH (scFv) (see, Bird et al. (1988) Science 242: 423-426; and Huston et al. (1988) Proc. Natl. Acad. Sci. 85: 5879-5883). The term "portion of antigen binding" may further comprise an immunoglobulin fusion protein comprising binding domains selected from the group consisting of (1) a peptide of binding domain fused with a peptide of immunoglobulin hinge region; (2) a heavy chain CH2 constant region of Immunoglobulin fused with a hinge region; and (3) a heavy chain CH3 constant region of immunoglobulin fused with a CH2 constant region.

For instance, the protein macromolecule that specifically binds to VEGFR may be Ramucimmab, a fragment of antigen binding or a functional variant thereof.

As used herein, the term "VEGF trapping agent" generally refers to an agent capable of trapping VEGF by binding thereof. For instance, the VEGF trapping agent may be selected from the group consisting of Bevacizumab and Aflibercept.

As used herein, the term "an agent of reducing the expression of VEGF" generally refers to a substance capable of directly or indirectly decreasing the expression of VEGF in a subject. For instance, the agent of reducing the expression of VEGF may be selected from the group consisting of Temsirolimus and Thalidomide.

As used herein, the term "RNAi" generally refers to RNA interference, which is generally an exogenous or endogenous double-stranded RNA molecule or a small molecular RNA, and typically inhibits the expression or translation of a target gene through the specific degradation of RNAi caused by targeting mRNA. In general, RNAi comprises two types of small molecular RNAs: microRNA (miRNA) and small interference RNA (siRNA), which are capable of binding to other mRNA molecules, thereby increasing or decreasing the activity thereof, e.g., preventing mRNA from being translated to protein. In an eukaryotic animal, RNAi path cleaves a long double-stranded RNA (dsRNA) by RNaseIII enzyme (e.g., Dicer, DCL or Drosha) to double-stranded siRNA fragments having about 20-23 nucleotides in length. Each siRNA is resolved to two single-stranded RNAs (ssRNA), i.e., a passenger chain and a guide chain. The passenger chain is degraded, while the guide chain is integrated into an RNA inducing silencing complex (RISC). When the guide chain is complementary to an mRNA molecule, the RISC cleaves the mRNA molecule, thereby resulting in the degradation of the mRNA molecule.

As used herein, an RNAi that inhibits the expression of a VEGFR protein may inhibit the expression or translation of VEGFR by targeting a mRNA encoding VEGFR so as to specifically degrading the mRNA. As used herein, the RNAi inhibiting the expression of VEGF protein may inhibit the expression or translation of VEGF by targeting an mRNA encoding VEGF so as to specifically degrading the mRNA.

As used herein, the term "oligonucleotide" generally refers to an oligomer or polymer of ribonucleic acid (RNA) or deoxyribonucleic acid (DNA) or any mimic thereof or structurally modified nucleic acid. The term comprises oligonucleotides consisting of naturally occurring nucleobases, pentose and covalent nucleoside (backbone), and non-naturally occurring oligonucleotides having similar function. The modified or substituted oligonucleotide is generally superior to the naturally occurring forms as they have, e.g. increased cell uptake, increased affinity to target nucleic acid, and increased stability in the presence of nuclease.

As used herein, the term "antisense oligonucleotide" generally refers to a single-stranded oligonucleotide having nucleobase sequence that may at least partially hybridize with the corresponding region or fragment of the target nucleic acid. As used herein, the antisense oligonucleotide may comprise about 8 to about 50 nucleobases.

As used herein, the VEGFR inhibitor is capable of inhibiting VEGFR1, VEGFR2 and/or VEGFR3. For instance, the VEGFR inhibitor is capable of inhibiting one, two or three of VEGFR1, VEGFR2, and VEGFR3.

In some embodiments, the VEGFR inhibitor may comprise Ramucirumab, Bevacizumab, Regorafenib, Ponatinib, Cabozantinib, Lenvatinib, Sorafenib, Pazopanib, Apatinib, Axitinib, Nintedanib, Vandetanib, Sunitinib, Midostaurin, Tivozanib, Fruquintinib, Cediranib, Brivanib, Donafenib, Sulfatinib, Anlotinib, Famitinib, Tesevatinib, Vorolanib, Motesanib, Linifanib, Semaxanib, Dovitinib, Orantinib, Vatalanib, Telatinib, Glesatinib, Lucitanib, Ilorasertib, Rebastinib, Golvatinib, Foretinib, Ningetinib, Tafetinib, Altiratinib, TAS-115, Chiauranib, Henatinib, 4SC-203, AAL-993, ACTB-1003, AEE-788, AMG-628, arenobufagin, BAW2881, BIBF-1202, BMS-690514, BMS-794833, CEP-11981, CEP-5214, CP-547632, CYC116, DW532, ENMD-2076, FIIN-1, GFB-204, BFH-772, BMS599626, BMS690514, PP 121, MGCD 265 analogue, AC480, Ki 8751, KRN 633, WHI-P 154, TAK593, JI 101, AZD-2932, SCR-1481B1, Isoliquiritigenin, JNJ-26483327, KI-20227, LY2457546, ODM-203, OSI-930, PF-00337210, CGP41231, R1530, RAF265, SAR131675, Semaxinib, SIM010603, SKLB1002, SKLB610, SU 5205, SU11652, SU14813, SU-1498, SU-4312, SU5402, T-1840383, tanshinone IIA, TAS-115, TG 100572, TG 100801, TG100572 HCl, Toceranib, Tyrosine phosphorylation inhibitor A9, Tesevatinib, XL-844, XL999, ZD4190 HCl, ZM-306416, ZM323881 HCl, ABT-510, NVP-ACC789, ADT-OH, BMS-645737, EG 00229, XL-820, SGI-7079, Endostatin, Taxifolin, Aflibercept, and/or a pharmaceutically acceptable salt of the VEGFR inhibitor and/or VEGF inhibitor above.

As used herein, the term "pharmaceutically acceptable salt" may refer to a pharmaceutically acceptable salt of the compound. In some embodiments, the pharmaceutically acceptable salt may be selected from the group consisting of Sorafenib tosylate, Sunitinib malate, Pazopanib hydrochloride, and Dovitinib (TKI258) lactate.

As used herein, the VEGFR inhibitor and/or the VEGF inhibitor may be administered in combination with one or more additional therapies. In some embodiments, the one or more additional therapies may comprise one or more additional anti-tumor therapy. For instance, the additional anti-tumor therapy may comprise cytotoxic anticancer agents, immunotherapeutic anticancer agents, or hormonotherapeutic anticancer agents. The additional anti-tumor therapies may further comprise radiotherapy or surgery therapy.

As used herein, when a VEGFR inhibitor and/or a VEGF inhibitor is administered in combination with additional anti-tumor therapies, they may be simultaneously administered to a subject or individually administered at intervals. For instance, the additional anti-tumor therapy may be a part of a single dosage form, and mixed with the VEGFR inhibitor and/or the VEGF inhibitor to form a single composition. As another example, the additional anti-tumor therapy may be a separate agent, which is administered separately from the VEGFR inhibitor and/or the VEGF inhibitor. As used herein, if the additional anti-tumor therapy and the VEGFR inhibitor and/or the VEGF inhibitor form a single composition, the VEGFR inhibitor and/or the VEGF inhibitor may be present and/or administered at a level of about 1-99% (e.g., about 5-95%, about 1%, about 5%, about 10%, about 20%, about 30%, about 40%, about 50%, about 60%, about 70%, about 80%, about 90%, about 95% or about 99%) in relation to the total dosage.

Cytotoxic anticancer agents used in treating cancer may comprise alkylating agents such aschlormethine, nitrogen mustard N-oxide hydrochloride, Chloroambucil, Cyclophosphamide, Ifosfamide, thiotepa, isothiocyanate, Busulfan, Nimustine hydrochloride, mitropium bromide, Melphalan, Dacarbazine, Ranimustine, promethamine sodium phosphate, Diethylenetriamine, Carmustine, Lomustine, Streptozotocin, pipobroman, ethoglucid, Carboplatin, Cisplatin, Miriplatin, Nedaplatin, tenetamide, omustine, dichloropyridine, prednimustine, prednimustine, pumitepa, Ribomustin, Temozolomide, diclofenac, trovafloxacin, zinstatin, simvastatin, penems, cystemustine and bizelesin; antimetabolite such as mercaptopurine, 6-mercaptopurine glycoside, 6-thioinosine, methotrexate, pemetrexed, vortioxetine, cytarabine, oxaliplatin, tizanidine hydrochloride, 5-FU and derivant of like (such as, fluorouracil, tegafur, UFT, Doxycycline, carmofur, capecitabine, etc); antitumor antibiotic such as actinomycin D, actinomycin C, mitomycin, Chromomycin A3, Bleomycin hydrochloride, Bleomycin, cetimycin hydrochloride, Doxorubicin hydrochloride, Mitoxantrone hydrochloride and Idarubicin hydrochloride; and/or, plant-derived cytotoxic anticancer drugs such as Etoposide, Etoposide phosphate, Vinblastine sulfate, Vincristine sulfate, Teniposide, paclitaxel, paclitaxel and vinorelbine and of like; VEGF inhibitor such as Bevacizumab, and thoseVEGF inhibitor disclosed at PCT patent application WO 2005/012359, WO 2005/044853, WO 98/45332, WO 96/30046, WO 94/10202, U.S. Pat. Nos. 7,060,269, 6,582,959, 6,703,020, 6,054,297, U.S. patent application US2006/009360, US2005/0186208, US2003/0206899, US2003/0190317, US2003/0203409 and US2005/0112126.

Immunotherapy agent used to treat cancer may comprise bubinini, Crestine, Benzofurazan, Lentinan, Ubenimex, Interferon, Interleukin, macrophage colony-stimulating factor, granulocyte colony-stimulating factor, Erythropoietin, lymphotoxin, BCG, *Corynebacterium Parvum*, everolimus, levamisole, PolysaccharideK, procodazole and/or immune checkpoint inhibitor (such as CTLA4 inhibitor, TIM-3 inhibitor, PD-1 inhibitor (such as, Nivolumab, Pembrolizumab, Pidilizumab, AMP514 (Amplimmune), AMP-224, and other PD-1 inhibitors disclosed PCT patent application WO2006/121168, WO2009/114335, WO2009/101611, U.S. Pat. No. 8,609,089, U.S. patent application US2010/028330, US2012/0114649), PD-L1 inhibitor (such as, YW243.55.S70, MPDL3280A, MEDI-4736, MSB-0010718C, MDX-1105, and other PD-L1 inhibitors disclosed in PCT patent application WO2010/077634 and U.S. Pat. No. 7,943,743)).

Hormonotherapeutic anti-cancer agent used in treating cancer may comprise urinastatin, diethylstilbestrol, chlorinated costen, medroxyprogesterone acetate, Megestrol acetate, cyproterone acetate, cyproterone acetate, danazol, allylestrenol, progesterone, mepartricin, Raloxifene, Levofloxacin, antiestrogen (such as, Tamoxifen citrate salt, toremifene citrate salt and of like), contraceptive pill, prostacyclin, testolactone, amino succinimide, LH-RH agonist (such as, goserelin acetate, buserelin, leuprorelin and of like), droloxifene, epiandrosterone, ethinylestradiol sulfonate, flubendazole hydrochloride, anastrozole, letrozole, exemestane, vorozole, anti-androgens (such as, flutamide, bicalutamide, nilutamide and of like), 5α-statin (such as, finasteride, episteride), corticosteroid (such as, Dexamethasone, Prednisolone, Betamethasone, Triamcinolone acetonide and of like) and/or androgen antagonists (such as, abiraterone and of like).

VEGFR and/or VEGF Inhibition-Associated Disease or Disorder

As used herein, the disease or disorder associated with administration of the VEGFR inhibitor and/or VEGF inhibitor may be statistically significantly associated with the VEGFR and/or VEGF inhibition. In some embodiments, the disease or disorder associated with administration of the VEGFR inhibitor and/or VEGF inhibitor is caused by the VEGFR and/or VEGF inhibition. For instance, the disease or disorder associated with administration of the VEGFR inhibitor and/or VEGF inhibitor may comprise skin tissue disease or disorder, facial organ disease or disorder and/or gastrointestinal disease or disorder associated with administration of the VEGFR inhibitor and/or VEGF inhibitor. For instance, the skin tissue disease or disorder, facial organ disease or disorder and/or gastrointestinal disease or disorder associated with administration of the VEGFR inhibitor and/or VEGF inhibitor may comprise a epithelial disease or disorder associated with administration of the VEGFR inhibitor and/or VEGF inhibitor in skin tissue, facial organ and/or gastrointestinal tract. In some embodiments, the disease or disorder associated with administration of the VEGFR inhibitor and/or VEGF inhibitor comprises side effects or adverse reactions caused by the VEGFR inhibitor and/or the VEGF inhibitor.

As used herein, the disease or disorder associated with administration of the VEGFR inhibitor and/or VEGF inhibitor may be a new indication that may be different from any other disease or disorder of the past. For instance, the diagnostic methods, treatment methods and/or symptoms of the disease or disorder associated with administration of the VEGFR inhibitor and/or VEGF inhibitor are all unique. For instance, erythromycin ointment is capable of treating rash, while has no effect on treating the rash associated with administration of the VEGFR inhibitor and/or VEGF inhibitor.

As used herein, the term "skin tissue disease or disorder" generally refers to the pathologic changes occurred in the morphology, structure and/or function of skin (including hair and nail). For instance, the skin tissue disease or disorder may comprise, but is not limited to rash, hand-foot syndrome, pruritus, erythema, xerosis cutis, alopecia, paronychia, pigmentation disorder, and the like.

As used herein, the term "rash" generally refers to a skin change capable of affecting the color, appearance, or texture of skin. Rash may be localized to only a portion of the body, or affect the overall skin. Rash further comprises urticaria.

As used herein, the term "hand-foot syndrome" is also known as Hand Foot Syndrome (HFS), or Palmar Plantar Erythrodysesthesia (PPE), or Hand-foot skin reaction (HFSR), which was first described in 1984 by Jacob Lokich and Cery Moor of New England Diaconis Hospital of Harvard Medical School. The typical clinical manifestations are progressive. The primary clinical manifestations comprise finger (toe) fever, pain, erythematous swelling, serious person for desquamation, ulcer, and severe pain, etc. The pathologic manifestations of HFS primarily comprise, e.g., basal keratinocyte vacuolar degeneration, skin perivascular lymphocyte infiltration, keratinocyte apoptosis, and skin edema, and the like. For instance, HFS may comprise palmar or plantar dysesthesia, or acral erythema caused by chemotherapy, or the like. Tumor patients may develop the corresponding symptoms during the process of chemotherapy or molecular targeted therapy (e.g., the VEGFR inhibitor and/or the VEGF inhibitor).

Currently, there are a variety of classification methods for hand-foot syndrome (HFS), wherein the criterion of the American National Cancer Institute (NCI) is relatively common used. This criterion classifies the hand-foot syndrome as 3 Grades: Grade 1 is minimal skin changes or dermatitis with paresthesia (e.g., fingerprints disappearance, pigmentation, erythema, decrustation, paresthesia, dysesthesia, skin numbness, etc.), but does not affect daily activities; Grade 2 is the same level of skin change as Grade 1 with pain, slightly affects daily activities, and the skin surface is intact; and Grade 3 is ulcerative dermatitis or serious painful cutaneous lesions, seriously affects daily life, and has obvious tissue damage (e.g., desquamation, blisters, hemorrhage, edema, etc.).

Moreover, the World Health Organization (WHO) classifies HFS as four grades: Grade 1 is a feeling of dysesthesia, paresthesia, or tingling in the hands and feet; Grade 2 is discomfort when holding objects and walking, painless swelling, or erythema; Grade 3 is painful erythema and swelling of palms and soles, periungual erythema and swelling; and Grade 4 is decmstation, ulceration, blistering and severe pain.

As used herein, the term "erythema" generally refers to local or systemic red maculae caused by localized or systemic expansion of dermal papillary capillary network.

As used herein, the term "paronychia" generally refers to an infectious lesion of soft tissues around finger (toe) nails, which is generally caused by subcutaneous invasion and reproduction of bacteria through slight skin damage near the nails, and has clinical manifestations including painful redness and swelling of the affected area, with inflammatory exudation, and granulation tissue proliferation, etc.

As used herein, the term "pigmentation disorder" generally refers to a disorder in which the skin exhibits a lighter or darker color as compared with normal conditions, produces stains, or discolors. Hypopigmentation is due to the insufficiently production of pigments in the body, while hyperpigmentation is due to the excess production of pigments in the body.

As used herein, the term "facial organ disease or disorder" generally refers to a pathologic change occurred in the morphology, structure, and/or function of organs including ears, eyebrows, eyes, nose, mouth, etc. For instance, the facial organ disease or disorder may comprise but are not limited to oral Mucositis, xerostomia (dry mouth), epistaxis, nasopharyngitis and/or cheilitis.

As used herein, the term "nasopharyngitis" generally refers to inflammatory reactions of nasopharyngeal mucosa, submucosa and lymphoid tissues, and may be classified to acute nasopharyngitis and chronic nasopharyngitis. Symptoms comprise, but are not limited to, nasopharyngeal dryness and discomfort, sticky secretions different to be coughed up, and are often accompanied with nausea, severe cases of hoarseness, sore throat, headache, dizziness, fatigue, indigestion, hypothermia, as well as other local or systemic symptoms. Nasopharyngeal examination shows chronic mucosa congestion, hyperplasia, hypertrophy, secretion covering or dry scab, etc.

As used herein, the term "cheilitis" generally refers to inflammatory disease or disorder occurring in lips. For instance, it may comprise inflammations of perioral skin, vermilion border, and/or buccal mucosa, and the like. It may be classified into: acute cheilitis and chronic cheilitis, according to the course of disease; erosive cheilitis, eczematous cheilitis, desquamative cheilitis, according to the clinic symptom characteristics; and chronic non-specific cheilitis, cheilitis glandularis, cheilitis of benign lymph adenosis, cheilitis granulomatosa, Melkersson-Rosenthal Syndrome, actinic cheilitis and allergic cheilitis, etc., according to the etiology and pathology.

As used herein, the term "gastrointestinal disease or disorder" generally refers to the pathological change of morphology, structure and/or function of gastric or intestinal tissues (e.g., digestive tract tissues from gastric pylorus to anus). For instance, the gastrointestinal disease or disorder may comprise, but is not limited to, diarrhea, vomiting, nausea, anorexia, constipation and/or abdominal pain, and the like.

As used herein, the VEGFR inhibitor and/or VEGF inhibitor may be used to treat tumor. For instance, the location of the disease or disorder is different from that of tumor.

As used herein, the skin tissue disease or disorder, facial organ disease or disorder and/or gastrointestinal disease or disorder associated with administration of the VEGFR inhibitor and/or VEGF inhibitor, may comprise epithelial disease or disorder associated with administration of the VEGFR inhibitor and/or VEGF inhibitor in the skin tissue, facial organ and/or gastrointestinal tract.

As used herein, the term "epithelial tissue" comprises one or more layers of free and surface-closed cells covering the whole body, comprising, skin, mucus, cavity, slurry and gland spaces. All the epithelial layers comprise two special domains, that is, the top domain facing the mucus (or cavity) space and the basolateral membrane facing the serosal (or deep) space. Thus, an important function of epithelial tissues is to provide a proper barrier to separate and control a variety of physiological processes between the two spaces. The epithelial tissue comprises epithelial cells and endothelial cells.

As used herein, the term "epithelial disease or disorder" generally refers to disease or disorder caused by lesion of epithelial cell and/or endothelia cell. For instance, the epithelial disease or disorder may comprise rash, acne, skin pruritus, alopecia, hair change, erythema, skin exfoliation, herpes, hirsutism, hyper-pigmentation, nail disorders, paronychia and schizonychia, xerosis cutis, hypersensitivity, mucositis, nasopharyngitis, nasopharyngitis, xerostomia, cheilitis, oral mucositis and/or gastrointestinal mucosal injury. As another example, the epithelial disease or disorder may also comprise skin epithelial cell disease or disorder (e.g., rash, acne, rosacea, atopic dermatitis, contact dermatitis, seborrheic dermatitis, lupus, scleroderma, pemphigus, pigmentation, black spot, leukoderma, urticaria, tinea corporis, the skin pruritus, alopecia, hair change, erythema, paronychia and schizonychia, xerosis cutis, hypersensitivity and psoriasis), oral epithelial cell disease or disorder (e.g., pemphigus, herpes labialis, herpetic stomatitis, granulomatous cheilitis, oral mucositis, pemphigoid, xerostomia syndrome, Bechet disease and oral sarcoidosis, etc.), nasal epithelial cell disease or disorder (epistaxis, sinusitis, nasal furuncle and nasal polyps, etc.), stomach epithelial cell diseases or disorders (e.g., gastritis, intestinal metaplasia, gastric perforation, gastric fistula, gastric ulcer and gastrointestinal polyp) and/or small intestine epithelial cell disease or disorder (e.g., enteritis, Crohn's disease, enterobrosis, intestinal fistula, enterelcosis, ulcerative colitis and NSAIDs bowel disease).

As used herein, the epithelial disease or disorder associated with administration of the VEGFR inhibitor and/or VEGF inhibitor may comprise the disease or disorder associated with lesion of endothelia cell, and/or the disease or disorder associated with epithelial cell lesion, wherein the lesion of endothelia cell and/or epithelial are associated with the VEGFR and/or VEGF inhibition.

For instance, the endothelial cells may comprise vascular endothelial cell. The lesion of vascular endothelial cell may comprise endothelia dysfunction. For instance, the lesion of vascular endothelia cell may comprise degenerative vascular disease (e.g., atherosclerosis, media arteriosclerosis and arteriolosclerosis (e.g., habilitative arteriolosclerosis and proliferative arteriolosclerosis)), inflammatory vascular disease (e.g., infectious arteritis, arteritis syphilitica, giant cell arteritis, thromboangitis obliterans and rheumatic arteritis), functional vascular disease (e.g., Raynaud's disease, acrocyanosis and erythema acrodynia) and congenital vascular disease (e.g., congenital arteriovenous fistula) and the like.

As used herein, the epithelial cell may comprise skin epithelial cell, oral epithelial cell, nasal epithelial cell, gastric epithelial cell and/or intestinal epithelial cell. For instance, the lesion of epithelial cell may comprise lesion of skin epithelial cell (e.g., rash, acne, rosacea, atopic dermatitis, contact dermatitis, seborrheic dermatitis, lupus, scleroderma, pemphigus, pigmentation, black spot, leukoderma, urticaria, tinea corporis, the skin pruritus, alopecia, hair change, erythema, paronychia and schizonychia, xerosis cutis, hypersensitivity and psoriasis), lesion of oral epithelial cell (e.g., pemphigus, herpes labialis, herpetic stomatitis, granulomatous cheilitis, oral mucositis, pemphigoid, xerostomia syndrome, Bechet disease and oral sarcoidosis, etc.), lesion of nasal epithelial cell (epistaxis, sinusitis, nasal furuncle and nasal polyps, etc.), lesion of gastric epithelial cell (e.g., gastritis, intestinal metaplasia, gastric perforation, gastric fistula, gastric ulcer and gastrointestinal polyp) and/or lesion of small intestine epithelial cell (e.g., enteritis, Crohn's disease, enterobrosis, intestinal fistula, enterelcosis, ulcerative colitis and NSAIDs bowel disease).

It is found by the inventor that the inhibition of VEGFR and/or VEGF may cause injury of endothelial cell, and endothelial tissue, thereby causing the disease or disorder of skin tissue, oral tissue, nasal tissue and/or gastrointestinal tissue. During the occurring and development of these disease or disorder, the course of disease generally begins with the injury/lesion of endothelial cell and endothelia tissue, together with the lesion symptoms of epithelial cell, and finally presents as endothelia cell lesion associated with administration of the VEGFR inhibitor and/or VEGF inhibitor, and/or epithelial cell lesion associated with administration of the VEGFR inhibitor and/or VEGF inhibitor in a patient.

In some embodiments, the disease or disorder associated with administration of the VEGFR inhibitor and/or VEGF inhibitor may comprise a rash associated with administration of the VEGFR inhibitor and/or VEGF inhibitor, hand-foot syndrome associated with administration of the VEGFR inhibitor and/or VEGF inhibitor, pruritus associated with administration of the VEGFR inhibitor and/or VEGF inhibitor, erythema associated with administration of the VEGFR inhibitor and/or VEGF inhibitor, xerosis cutis associated with administration of the VEGFR inhibitor and/or VEGF inhibitor, alopecia associated with administration of the VEGFR inhibitor and/or VEGF inhibitor, paronychia associated with administration of the VEGFR inhibitor and/or VEGF inhibitor, pigmentation disorder associated with administration of the VEGFR inhibitor and/or VEGF inhibitor, oral mucositis associated with administration of the VEGFR inhibitor and/or VEGF inhibitor, xerostomia associated with administration of the VEGFR inhibitor and/or VEGF inhibitor, epistaxis associated with administration of the VEGFR inhibitor and/or VEGF inhibitor, nasopharyngitis associated with administration of the VEGFR inhibitor and/or VEGF inhibitor, cheilitis associated with administration of the VEGFR inhibitor and/or VEGF inhibitor, esophagitis associated with administration of the VEGFR inhibitor and/or VEGF inhibitor, esogastritis associated with administration of the VEGFR inhibitor and/or VEGF inhibitor, gastric ulcer associated with administration of the VEGFR inhibitor and/or VEGF inhibitor, diarrhea associated with administration of the VEGFR inhibitor and/or VEGF inhibitor, vomiting associated with administration of the VEGFR inhibitor and/or VEGF inhibitor, nausea associated with administration of the VEGFR inhibitor and/or VEGF inhibitor, anorexia associated with administration of the VEGFR inhibitor and/or VEGF inhibitor, constipation associated with administration of the VEGFR inhibitor and/or VEGF inhibitor, and/or, abdominal pain associated with administration of the VEGFR inhibitor and/or VEGF inhibitor. For instance, disease or disorder associated with administration of the VEGFR inhibitor and/or VEGF inhibitor comprise hand-foot syndrome associated with administration of the VEGFR inhibitor and/or VEGF inhibitor. For instance, the severity of hand-foot syndrome associated with administration of the VEGFR inhibitor and/or VEGF inhibitor is Grade 1 or above, Grade 2 or above, Grade 3 or above, Grade 4 or above, and/or Grade 5 or above according to NCI-CTCAE V5.0.

In some embodiments, the disease or disorder may comprise rash, hand-foot syndrome, pruritus, erythema, xerosis cutis, alopecia, paronychia, pigmentation disorder, oral mucositis, xerostomia, epistaxis, nasopharyngitis, cheilitis, esophagitis, esogastritis, gastric ulcer, diarrhea, vomiting, nausea, anorexia, constipation, and/or, abdominal pain. For instance, the disease or disorder comprises hand-foot syndrome.

In some embodiments, the VEGFR and/or VEGF inhibition-associated disease or disorder cannot substantially be treated or ameliorated by administration of an agent selected from the group consisting of: 1% sildenafil, urea frost, Vaseline ointment, urea ointment, brimonidine ointment, vitamin B6 ointment, nicotine ointment, dexamethasone ointment, hydrocortisone ointment, Vkl ointment (0.1%), erythrosine ointment and triamcinolone ointment.

Nitric Oxide Releasing Agent

As used herein, the term "the nitric oxide releasing agent" generally refers to any substance capable of contributing to, producing and/or releasing nitric oxide. In some embodiments, the nitric oxide releasing agent may directly contribute to, produce and/or release nitric oxide. For instance, the nitric oxide releasing agent may stimulate other substances so as to contribute to, produce and/or release nitric oxide.

For instance, the nitric oxide releasing agent serves as a reactant of a chemical or enzyme-catalyzed reaction and contributes to, produces and/or releases nitric oxide via such reaction. In some embodiments, the nitric oxide releasing agent serves a catalyst of a chemical or enzyme-catalyzed reaction, and stimulates other substances to contribute to, produce and/or release nitric oxide via such reaction. The nitric oxide releasing agent may comprises nitric oxide itself.

The nitric oxide releasing agents may be identified or screened by methods well known in the art, e.g., it is possible to detect the ability of the compound to be tested for contributing, producing, releasing and/or directly or indirectly transferring nitric oxide by detecting the levels of nitrite, NO, $NO^{2-}$ and/or S-nitroso thiol. Any method known in the art may be used to detect the level of nitrite, NO, $NO^{2-}$ and/or S-nitroso thiol. For instance, the nitric oxide releasing agents may be identified or screened by detecting nitrite, e.g., analyzing nitrite by Griess Analysis (Molecular Probes), which is on the basis of the reaction between nitrite and para-amino benzenesulfonic acid, followed by detecting the reaction product via spectrophotometry. It is also possible to carry out the measurement by reducing nitrite/nitrate to NO in a reflux chamber at 95° C. by a highly sensitive chemiluminescence technology. As another example, it is possible to identify or screen the nitric oxide releasing agents by detecting the Hb-NO level in blood. It is known that NO binds closely to hemoglobin (Hb), and the interaction between NO and Hb is known as the primary pathway of NO metabolism in blood vessels. Thus, the Hb-NO level in blood is a good indicator of the endogenous production of NO. In some embodiments, it is possible to determine the paramagnetic hemoglobin-NO adduct (Hb-NO) in the whole blood and the erythrocytes by electron paramagnetic response (EPR) spectroscopy so as to identify or screen the nitric oxide releasing agents. As another example, it is possible to identify or screen the nitric oxide releasing agents by amperometry of NO-specific electrode. This method requires inserting a NO electrode into the living body or sample. As another example, it is possible to identify or screen the nitric oxide releasing agents by detecting S-nitroso thiol. In Eco Medics CLD 88 Exhalyzer (Annex, Herts, UK), the S-nitroso thiol of a protein is measured by using chemiluminescence detection (Feelisch, M. et al., Concomitant S-, N-, and heme-nitros(yl)ation in biological tissues and fluids: implications for the fate of NO in vivo. FASEB. J 16, 1775-85 (2002)). As another example, it is possible to indirectly detect the NO level so as to identify or screen the nitric oxide releasing agents. For instance, an EndoPAT method is used to perform a non-invasive endothelial function detection to measure the NO level. The particular detection method may be found in U.S. Pat. No. 9,696,324. It is also possible to indicate the NO level in serum by means of specifically reducing $NO_3^-$ to $NO_2^-$ by using a nitrate reductase, reacting $NO_2^-$ with a chromogenic agent to generate a colored substance, and measuring the absorbance, thereby identifying or screening the nitric oxide releasing agents.

As used herein, the nitric oxide releasing agent is capable of producing at least one of $NO^+$, $NO^-$, $N_2O$, NO, $N_2O_3$, $NO_2$, $NO_3^-$ and $NO_2^-$. For instance, the nitric oxide releasing agent is capable of directly or indirectly producing NO.

As used herein, the nitric oxide releasing agent may comprise an organic molecule, an inorganic molecule, a macromolecule, a nanomaterial, and/or an Ammonia Oxidizing Microorganism (AOM). For instance, the nitric oxide releasing agent may be NO.

As used herein, the item "organic molecular" generally refer to compound comprising carbon element, and not comprising oxide of carbon, carbonic acid, carbonate, cyanogen, cyanide, oxocyanide, cyanate, thiocyanogen, metal carbide and of like.

For instance, the nitric oxide releasing agent may comprise organic molecules, and the organic molecules may comprise nitroglycerin, isosorbide mononitrate, pentaerythritol tetranitrate, isosorbide dinitrate, trolnitrate, Nicorandil, propatyl nitrate, Molsidomine, 5-amino-3-(4-morpholinyl)-1,2,3-oxadiazole, isoamyl nitrite, 3,3-di(aminoethyl)-1-hydroxyl-2-carbonyl-1-triazene (NOC-18), sulfa nucleophilic complex disodium salt, S-nitroso glutathione, S-nitroso-N-acetyl penicillamine, 4-phenyl-3-furonitrile, (±)-(E)-4-Ethyl-2[(E)-hydroxyimino]-5-nitro-3-hexenamide, streptozocin, NG-Hydroxy-L-arginine acetate salt, $O_2$-(2,4-Dinitrophenyl) 1-[(4-ethoxycarbonyl)piperazin-1-yl]diazen-1-ium-1,2-diolate, N-nitrosodibutylamine, 3-morpholinosydnonimine, linsidomine, 3-(4-acetylphenyl) sydnone, diethylamine nucleophilic complex/AM, and/or Itramin. For instance, the nitric oxide releasing agent may comprise organic molecules, and the organic molecules may comprise nitroglycerin, isosorbide mononitrate, and/or isosorbide dinitrate. In some embodiments, the organic molecules may comprise nitroglycerin.

As used herein, the nitric oxide releasing agent may comprise inorganic molecule, and the inorganic molecule may comprise nitryl complex, nitrosyl complex, metal nitrosamine complex, nitrate and/or nitrite. For instance, the inorganic molecule may comprise sodium nitroprusside.

As used herein, the nitric oxide releasing agent may have a relative molecular weight of 2000 Daltons or below, 1500 Daltons or below, 1200 Daltons or below, 1000 Daltons or below, 900 Daltons or below, 800 Daltons or below, 700 Daltons or below, 600 Daltons or below, 500 Daltons or below, 400 Daltons or below, 300 Daltons or below, 200 Daltons or below, or 100 Daltons or below.

As used herein, the nitric oxide releasing agent may be a polymer comprising NO-donating groups. Any suitable polymer may be used, including crosslinked or uncross linked polymer, dendritic polymer, metal compound, organic metal compound, inorganic compound and other polymer scaffolds.

The NO-releasing polymers may comprise, NO-releasing co-condensation silica, such as, diazoxide Bisulfate-functionalized polysiloxanepolyciliate, NO-releasing zeolite (see, U.S. Patent Application US2006/0269620 or US2010/0331968), NO-releasing metal organic framework (MOF) (see, U.S. Patent Application US2010/0239512 or US2011/0052650), NO-releasing multi-donor compound (see, U.S. Patent Application US2014/0171395), NO-releasing dendritic polymer or metal structure (see, U.S. Patent Application US2009/0214618), NO-releasing coating (see, U.S. Patent Application US2011/0086234), and the compounds described in U.S. Patent Application US2010/0098733 and PCT Patent Application WO2012/100174, the disclosure of which are hereby incorporated by reference in their entity. In some embodiments, the nitric oxide releasing agent is a nanomaterial containing NO-donating group (s), e.g., nanociystal that is a co-condensation siloxane network formed by silicon dioxide.

As another example, the NO-releasing polymer may further comprise S-nitrosothiol silica nanospheres, 5-nitrosoethanedithiol chitin, oligopropylenediamine-grafted chitosan nitric oxide/nucleophile complexes and/or the nitric oxide releasing agents manufactured by Novan Inc. (e.g., SB204, SB206, SB208, SB414 or NVN3100) and those disclosed in U.S. Patent U.S. Pat. Nos. 8,282,967, 8,956,658, 8,962,029, 9,403,851, 9,403,852, 9,187,501, 8,399,005, 8,981,139, 9,713,652, 9,238,038, 9,669,041, 8,591,876, 9,526,738, 9,737,561, 9,427,605, U.S. Patent Application US2009/0214618, US2012/0021055, US2012/0034169, US2014/0005426, US2014/0058124, US2015/0182543, US2016/0060279, US2014/0065200, US2015/0225488, US2010/0297200, US2013/0196951, US2013/0344334, US2014/0017121, US2011/0086234, US2014/0134321, US2010/0098733, US2012/0230921, US2014/0171395, US2016/0083339, US2016/0199295, US2014/0255318, US2017/0246205, US2012/0136323, US2012/0156163, US2014/0057001, US2012/0134951, US2017/0056437, US2017/0312307, US2017/0216197, US2015/0024052, US2008/0311163, US2016/0256366, US2015/0111973, US2017/0196905, PCT Patent Application WO2017/079268, WO2004/009253, WO2017/151905, WO2016/160089 and WO2017/019614.

As used herein, oligopropylenediamine-grafted chitosan nucleophile complex may comprise diazeniumcliolate. For instance, a nitric oxide releasing agent may be oligopropylenediamine-grafted chitosan NONOate. As used herein, NONOate may comprise a chemical compound with a structure of $R^1R^2N$—(NO—)—N═O, wherein, $R^1$ and $R^2$ are both alkyls.

As used herein, the nitric oxide releasing agent may comprise ammonia oxidizing microorganisms (AOM), and the ammonia oxidizing microorganisms (AOM) may comprise ammonia oxidizing bacteria (AOB). For instance, the ammonia oxidizing microorganisms (AOM) may comprise *Nitrosomonas, Nitrosococcus, Nitrosospira, Nitrosocystis, Nitrosolobus* and/or *Nitrosovibrio*. For instance, the ammonia oxidizing microorganisms (AOM) may comprise AOBiome, microbiota releasing NO of LLC (such as AOB101, AOB102, AOB103, AOB201, AOB201 or AOB203), and those disclosed in U.S. Pat. No. 7,820,420B2, U.S. Pat. No. 9,738,870B2, WO2017004534A2, U.S. Ser. No. 10/078,054B2, US2017189454A1, US20170191109A1, US20180092948A1, WO2018057710A1, WO2018017583A1, WO2018111888A1, US20070148136A1, US2005106126A1, US20170037363A1, CN1997731A, US20170189454A1 and WO2017004557A1.

As used herein, the term "polymer" generally mean that any compound with a molecular weight of greater than 2000 Daltons, greater than 3000 Daltons, greater than 4000 Daltons, greater than 5000 Daltons, greater than 6000 Daltons, greater than 7000 Daltons, greater than 8000 Daltons, greater than 9000 Daltons, greater than 10000 Daltons, greater than 12000 Daltons, greater than 15000 Daltons or greater than 20000 Daltons.

As used herein, the term "small molecule" generally means that any compound with a molecular weight of 2000 Daltons or less, 1500 Daltons or less, 1200 Daltons or less, 1000 Daltons or less, 900 Daltons or less, 800 Daltons or less, 700 Daltons or less, 600 Daltons or less, 500 Daltons or less, 400 Daltons or less, 300 Daltons or less, 200 Daltons or less or 100 Daltons or less.

As used herein, the nitric oxide releasing agent may have one or more groups as follow: diazeniumdiolate, hydroxykliazenesulfonic acid, S-nitrosothiol, furoxan, oxime, N-nitrosoamine, N-hydroxylguanidine, diazeniumcliolate, nitrate, nitrite, nitrate ester, nitrite ester, sydnonimine, sydnone, oxatriazol-5-imine, oxatriazol-5-one, hydroxylamine, dioxadiazacyclobutene, N-hydroxylnitrosoamine, N-nitrosoimine, hydroxycarbamide and metal nitrosamino complex.

For instance, the nitric oxide releasing agent may has one or more groups selected from Table 1:

TABLE 1

| NO. | Compound | Structure of compound | Description |
|---|---|---|---|
| 1 | Diazeniumdiolate | (structure) | Of those, R, R1, R2 may be organic chemical groups; M may be metal cation; X may be inorganic anion; a, b, n may be positive integer. |
| 2 | Diazeniumdiolate ester | (structure) | |
| 3 | Hydroxyldiazenesulfonic acid | (structure) | |
| 4 | S-nitrosothiol | R—S—N═O | |
| 5 | Furoxan | (structure) | |
| 6 | Oxime | (structure) | |

TABLE 1-continued
| NO. | Compound | Structure of compound | Description |
|---|---|---|---|
| 7 | N-nitrosoamine | | |
| 8 | N-hydroxylguanidine | | |
| 9 | Nitrate | | |
| 10 | Nitrate ester | | |
| 11 | Nitrite | | |
| 12 | Nitrite ester | | |
| 13 | Sydnonimine | | |
| 14 | Sydnone | | |
| 15 | Oxatriazol-5-imine | | |
| 16 | Oxatriazol-5-one | | |
| 17 | Hydroxylamine | $H_2N-OH$ | |
| 18 | Dioxadiazacyclobutene | | |
| 19 | N-hydroxylnitrosoamine | | |
| 20 | N-nitrosoimine | | |
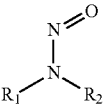

TABLE 1-continued

| NO. | Compound | Structure of compound | Description |
|---|---|---|---|
| 21 | N-hydroxycarbamide | 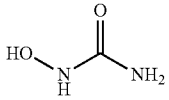 | |
| 22 | Metal nitrosamino complex | 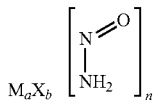 | |

As used herein, the nitric oxide releasing agent may be positively charged, electrically neutral, or negatively charged under physiological conditions. As used herein, the nitric oxide releasing agent may have a logP ranging from 1 to 5. For instance, the nitric oxide releasing agent may have a logP ranging from 1.5 to 3.5.

The nitric oxide releasing agent of the present application may be used to prevent or treat the administration of a VEGFR inhibitor and/or VEGF inhibitor-associated diseases or disorders.

Method of Preventing and/or Treating Diseases and Related Uses

As used herein, the nitric oxide releasing agent may be used to prepare a medicament for preventing or treating the administration of a VEGFR inhibitor and/or VEGF inhibitor-associated diseases or disorders.

As used herein, the nitric oxide releasing agent may be used to prevent or treat the rash associated with administration of the VEGFR inhibitor and/or VEGF inhibitor, hand-foot syndrome associated with administration of the VEGFR inhibitor and/or VEGF inhibitor, pruritus associated with administration of the VEGFR inhibitor and/or VEGF inhibitor, erythema associated with administration of the VEGFR inhibitor and/or VEGF inhibitor, xerosis cutis associated with administration of the VEGFR inhibitor and/or VEGF inhibitor, alopecia associated with administration of the VEGFR inhibitor and/or VEGF inhibitor, paronychia associated with administration of the VEGFR inhibitor and/or VEGF inhibitor, pigmentation disorder associated with administration of the VEGFR inhibitor and/or VEGF inhibitor, oral mucositis associated with administration of the VEGFR inhibitor and/or VEGF inhibitor, xerostomia associated with administration of the VEGFR inhibitor and/or VEGF inhibitor, epistaxis associated with administration of the VEGFR inhibitor and/or VEGF inhibitor, nasopharyngitis associated with administration of the VEGFR inhibitor and/or VEGF inhibitor, cheilitis associated with administration of the VEGFR inhibitor and/or VEGF inhibitor, esophagitis associated with administration of the VEGFR inhibitor and/or VEGF inhibitor, esogastritis associated with administration of the VEGFR inhibitor and/or VEGF inhibitor, gastric ulcer associated with administration of the VEGFR inhibitor and/or VEGF inhibitor, diarrhea associated with administration of the VEGFR inhibitor and/or VEGF inhibitor, vomiting associated with administration of the VEGFR inhibitor and/or VEGF inhibitor, nausea associated with administration of the VEGFR inhibitor and/or VEGF inhibitor, anorexia associated with administration of the VEGFR inhibitor and/or VEGF inhibitor, constipation associated with administration of the VEGFR inhibitor and/or VEGF inhibitor, and/or, abdominal pain associated with administration of the VEGFR inhibitor and/or VEGF inhibitor. For instance, the nitric oxide releasing agent may be used to prevent or treat hand-foot syndrome associated with administration of the VEGFR inhibitor and/or VEGF inhibitor.

As used herein, the nitric oxide releasing agent may be used to prevent or treat rash, hand-foot syndrome, pruritus, erythema, xerosis cutis, alopecia, paronychia, pigmentation disorder, oral mucositis, xerostomia, epistaxis, nasopharyngitis, cheilitis, esophagitis, esogastritis, gastric ulcer, diarrhea, vomiting, nausea, anorexia, constipation, and/or, abdominal pain. For instance, the nitric oxide may be used to prevent or treat hand-food syndrome.

In some embodiments, the medicament is formulated to be suitable for topical administration. In some embodiments, the location of topical administration may not be a primary location of tumor or potential metastasis site of tumor. For instance, the administrating site may be not a primary location of tumor. For another instance, the administrating site may be not a metastasis site of tumor. For instance, the metastasis site may comprise a site of tumor metastasis caused by lymphatic metastasis, vascular metastasis and/or transcoelomic metastasis. In some embodiments, the metastasis site may comprise bone, brain, liver, stomach and/or lungs. For another instance, the administrating site may be not a recurrence site of tumor. In the medicament of the present application, the nitric oxide releasing agent may be present at a concentration of about 0.0001% (w/w) to about 50% (w/w), e.g., it may vary in a range from about 0.0001% (w/w) to about 10% (w/w), from about 0.0001% (w/w) to about 9.5% (w/w), from about 0.0001% (w/w) to about 9% (w/w), from about 0.0001% (w/w) to about 8.5% (w/w), from about 0.0001% (w/w) to about 8% (w/w), from about 0.0001% (w/w) to about 7.5% (w/w), from about 0.0001% (w/w) to about 7% (w/w), from about 0.0001% (w/w) to about 6.5% (w/w), from about 0.0001% (w/w) to about 6% (w/w), from about 0.0001% (w/w) to about 5.5% (w/w), from about 0.0001% (w/w) to about 5% (w/w), from about 0.0001% (w/w) to about 4.5% (w/w), from about 0.0001% (w/w) to about 4% (w/w), from about 0.0001% (w/w) to about 3.5% (w/w), from about 0.0001% (w/w) to about 3% (w/w), from about 0.0001% (w/w) to about 2.5% (w/w), from about 0.0001% (w/w) to about 2% (w/w), from about 0.0001% (w/w) to about 1.5% (w/w), from about 0.0001% (w/w) to about 1% (w/w), from about 0.0001% (w/w) to about 0.5% (w/w), from about 0.0001% (w/w) to about 0.01% (w/w) or less. In the medicament of the present application, the nitric oxide releasing agent may be present as a concentration vary in a range from about 0.0001% (w/w) to about 1% (w/w), about 0.0001% (w/w) to about 0.9% (w/w), from about 0.0001% (w/w) to about 0.6% (w/w), from about 0.05% (w/w) to about 0.5% (w/w), from about 0.05% (w/w) to about 0.4% (w/w), from about 0.05%

(w/w) to about 0.3% (w/w), from about 0.05% (w/w) to about 0.2% (w/w), from about 0.1% (w/w) to about 0.2% (w/w) or less. For instance, the nitric oxide releasing agent may be present at a concentration of about 0.2% (w/w). Or, the nitric oxide releasing agent may be present at a concentration of about 0.1% (w/w).

As used herein, the medicament comprising the nitric oxide releasing agent may not substantially affect the therapeutic effect of the VEGFR inhibitor and/or the VEGF inhibitor. For instance, by administration of a medicament comprising the nitric oxide releasing agent, it is not required to increase the dose of the VEGFR inhibitor and/or the VEGF inhibitor to achieve substantially the same therapeutic effect.

In some embodiments, the medicament is formulated to be suitable for external administration.

In some embodiments, the medicament is formulated to be suitable for topically dermal administration. For instance, the medicament may be ointment, lotion or cream.

As used herein, the medicament may further comprise one or more additional active ingredients. For instance, the active ingredients may refer to a monomeric compound having medical effect or biological activity. For instance, the other active ingredients may be selected from the group consisting of anti-inflammatory agents, analgesics, local anesthetics, antihistamines, preservatives, immunosuppresses, and anti-bleeding agents.

As used herein, the medicament may further comprise a pharmaceutically acceptable carrier. For instance, the pharmaceutically acceptable carrier may be selected from the group consisting of fillers, adhesives, disintegrating agents, buffers, preservatives, lubricants, flavoring agents, thickeners, colorants and emulsifying agents.

In another aspect, the present application provides a nitric oxide releasing agent used to prevent or treat a VEGFR and/or VEGF inhibition-associated disease or disorder (for instance, a VEGFR and/or VEGF inhibition-associated epithelial tissue disease or disorder.)

In another aspect, the present application provides a method of preventing or treating VEGFR and/or VEGF inhibition-associated diseases or disorders in a subject. The method comprising administering to the subject a prophylactically or therapeutically effective amount of the nitric oxide releasing agent of the present application.

As used herein, the term "prevent" may be interchangeably used with "prophylactically treat". In the present application, the term "prevent" generally refers to prevent the occurrence, reoccurrence or diffusion of diseases or one or more symptoms thereof by taking some actions in advance. As used herein, the term "treat" generally refers to eliminate or improve disease or ameliorate one or more symptoms associated with the diseases.

As used herein, the term "subject" generally refers to a human or non-human animal (including mammals, rodents, and birds, etc.) in need of accepting a diagnosis, prognosis, improvement, prevention, and/or treatment. For instance, the subject may be a livestock (such as cow, pig, goat, chicken, rabbit or horse), or rodents (such as rat and mouse), or primates (such as gorilla and monkey), domestic animals (such as dog and cat). As used herein, the subject may be those subject that need a nitric oxide releasing agent to treat or prevent. As used herein, the subject may comprise cancer patient. For instance, the subject may have been, is and/or will be administrated the VEGFR inhibitor and/or the VEGF inhibitor. For instance, the VEGFR inhibitor and or VEGF inhibitor may be the VEGFR inhibitor and or VEGF inhibitor described in the present application.

As used herein, the severity of the disease or disorder may increase after administrating the VEGFR inhibitor or VEGF inhibitor. For instance, the severity of the disease or disorder may increase about 5% or above, 10% or above, 15% or above, 20% or above, 25% or above, 30% or above, 35% or above, 40% or above, 45% or above, 50% or above, 60% or above, 70% or above, 80% or above, 90% or above, 100% or above, 200% or above or more.

As used herein, the subject may not suffer the disease or disorder before administrating the VEGFR inhibitor and/or VEGF inhibitor. As used herein, the term "the subject doesn't suffer the disease or disorder" generally refers to the subject has no previous medical history related to the administration of a VEGFR inhibitor and/or VEGF inhibitor-associated disease or disorder. For instance, the subject doesn't suffer the disease or disorder associated with the administration of the VEGFR inhibitor and/or VEGF inhibitor for one day more, one week more, one month more, one year more, ten years more before administrating the VEGFR inhibitor and/or VEGF inhibitor, or since the subject was born.

As used herein, the VEGFR inhibitor and/or VEGF inhibitor doesn't comprise the nitric oxide releasing agent. For instance, the VEGFR inhibitor and/or VEGF inhibitor doesn't comprise nitroglycerin.

As used herein, the term "effective amount" refers to an amount of medicament capable of ameliorating or eliminating diseases or symptoms of the subject, or prophylactically inhibiting or prohibiting the occurrence of diseases or symptoms. In general, the particular effective amount may determine depending on the body weight, age, sex, diet, excretion rate, medical history, current therapy, time of administration, dosage form, administration mode, administration route, combination of medicaments, health conditions or cross infection potential of the subject, allergy, hypersensitivity, and side effects, and/or degree of epithelial (or endothelial) tissue disease development. The skilled man in the art (e.g., physicians or veterinarians) may decrease or increase the administration dosage in portion in accordance with these or other conditions.

In some embodiments, the nitric oxide releasing agent administrated may be present at a concentration of about 0.0001% (w/w) to about 50% (w/w), e.g., it may vary in a range from about 0.0001% (w/w) to about 10% (w/w), from about 0.0001% (w/w) to about 9.5% (w/w), from about 0.0001% (w/w) to about 9% (w/w), from about 0.0001% (w/w) to about 8.5% (w/w), from about 0.0001% (w/w) to about 8% (w/w), from about 0.0001% (w/w) to about 7.5% (w/w), from about 0.0001% (w/w) to about 7% (w/w), from about 0.0001% (w/w) to about 6.5% (w/w), from about 0.0001% (w/w) to about 6% (w/w), from about 0.0001% (w/w) to about 5.5% (w/w), from about 0.0001% (w/w) to about 5% (w/w), from about 0.0001% (w/w) to about 4.5% (w/w), from about 0.0001% (w/w) to about 4% (w/w), from about 0.0001% (w/w) to about 3.5% (w/w), from about 0.0001% (w/w) to about 3% (w/w), from about 0.0001% (w/w) to about 2.5% (w/w), from about 0.0001% (w/w) to about 2% (w/w), from about 0.0001% (w/w) to about 1.5% (w/w), from about 0.0001% (w/w) to about 1% (w/w), from about 0.0001% (w/w) to about 0.5% (w/w), from about 0.0001% (w/w) to about 0.01% (w/w) or less. In the medicament of the present application, the nitric oxide releasing agent may be present as a concentration vary in a range from about 0.0001% (w/w) to about 1% (w/w), about 0.0001% (w/w) to about 0.9% (w/w), from about 0.0001% (w/w) to about 0.6% (w/w), from about 0.05% (w/w) to about 0.5% (w/w), from about 0.05% (w/w) to about 0.4% (w/w), from about 0.05% (w/w) to about 0.3% (w/w), from about 0.05%

(w/w) to about 0.2% (w/w), from about 0.1% (w/w) to about 0.2% (w/w) or less. For instance, the nitric oxide releasing agent may be present at a concentration of about 0.2% (w/w). Or, the nitric oxide releasing agent may be present at a concentration of about 0.1% (w/w).

As used herein, the subject may comprise a human or non-human animal. For instance, the non-human animal may be selected from the group consisting of monkey, chicken, goose, cat, dog, mouse, and rat. Moreover, the non-human animal may further comprise any animal species other than human, e.g., livestock, or rodents, or primates, or domestic animals, or domestic fowls. The human may be Caucasian, African, Asian, Semite, or other races, or a combination of various races. As another example, the human may be elderly, adult, adolescent, child, or infant.

The effective amount in humans may be derived from the effective amount in the laboratory animals. For instance, Freireich et al. describe the relation between the dosages in animals and humans (milligrams per square meter of body surface) (Freireich et al., Cancer Chemother. Rep. 50, 219 (1966)). The body surface area may be approximately determined in accordance with the height and body weight of the patient. See, e.g., Scientific Tables, Geigy Pharmaceuticals, Ardsley, N.Y., 537 (1970).

In the method of the present application, the VEGFR and/or VEGF inhibition may be caused by administration of the VEGFR inhibitor and/or the VEGF inhibitor to the subject.

For instance, the nitric oxide releasing agent may be administered before, simultaneously with, or after the administration of the VEGFR inhibitor and/or the VEGF inhibitor to the subject. When the VEGFR inhibitor and/or the VEGF inhibitor and the nitric oxide releasing agent of the present application are simultaneously administered, the nitric oxide releasing agent is administered at a level of about 0.0001-10% (e.g., about 0.005-10%, about 0.01-10%, about 0.05-10%, about 0.1-10%, about 0.2-10%, about 0.3-10%, about 0.4-10%, about 0.5-10%, about 0.6-10%, about 0.7-10%, about 0.8-10%, about 0.9-10%, about 0.95-10%, about 1-10%, about 2-10%, about 3-10%, about 5-10%, about 6-10%, about 8-10% or less) in relative to the total dose. In an embodiment in which the nitric oxide releasing agent and the VEGFR inhibitor and/or the VEGF inhibitor are administered at intervals, the nitric oxide releasing agent may be administered at intervals before or after the administration of the VEGFR inhibitor and/or the VEGF inhibitor. The time interval may be 1 min, 2 mins, 5 mins, 10 mins, 20 mins, 30 mins, 45 mins, 1 hour, 2 hours, 3 hours, 4 hours, 5 hours, 6 hours, 12 hours, 18 hours, 1 day, 2 days, 3 days, 1 week, 2 weeks, 3 weeks, 1 month, 2 months, 3 months or longer.

In some embodiments, the nitric oxide releasing agent is externally administered. In some embodiments, the nitric oxide releasing agent is administered in an ointment. In some embodiments, the nitric oxide releasing agent is administered together with one or more additional active ingredients. In some embodiments, the administration of the nitric oxide releasing agent does not substantially affect the therapeutic effect of the VEGFR inhibitor and/or the VEGF inhibitor.

In another aspect, the present application provides a combination of medicaments (e.g., a kit). The combination of medicaments may comprise: 1) the VEGFR inhibitor and/or the VEGF inhibitor of the present application; and 2) the nitric oxide releasing agent of the present application. In some embodiments, the VEGFR inhibitor and/or the VEGF inhibitor and the nitric oxide releasing agent are not mixed with each other.

In some embodiments, the VEGFR inhibitor and/or the VEGF inhibitor and the nitric oxide releasing agent each independently presents in a separate container. For instance, the combination of medicaments may comprise two or more medicaments which are packaged separately from each other, wherein at least one of the medicaments comprises the VEGFR inhibitor and/or the VEGF inhibitor of the present application and wherein at least one additional medicament comprises the nitric oxide releasing agent of the present application.

In some embodiments of the combination of medicaments, the nitric oxide releasing agent of 2) is capable of preventing or treating the disease or disorder associated with the VEGFR inhibitor and/or the VEGF inhibitor of 1) (e.g., the disease or disorder associated with administration of VEGFR inhibitor or VEGF inhibitor of the present application). In some embodiments, the nitric oxide releasing agent of 2) does not substantially affect the therapeutic effect of the VEGFR inhibitor and/or the VEGF inhibitor of 1). In some embodiments, the nitric oxide releasing agent of 2) is administered before, simultaneously with, or after the administration of the VEGFR inhibitor and/or the VEGF inhibitor of 1).

As used herein, the term "does not substantially affect" may refer to, comparing to the therapeutic effect of using the VEGFR inhibitor and/or VEGF inhibitor independently, the therapeutic effect of using the nitric oxide releasing agent of 2) or kit and the VEGFR inhibitor and/or VEGF inhibitor of 1) of combination of medicaments is equal, or not worse significantly. For instance, to any subject, compared with therapeutic effect of administration of the VEGFR inhibitor and/or VEGF inhibitor independently, the decreased tumor volume of administration the nitric releasing agent of 1) and the VEGFR inhibitor and/or VEGF inhibitor of 2) of the combination of medicaments or kit is equal or, decreased by no less than about 5%, no less than about 4%, no less than about 3%, no less than about 2%, no less than about 1%, no less than about 0.5%, no less than about 0.1%, no less than about 0.01%, no less than about 0.001%, or less.

The present application further provides a method comprising administrating a nitric oxide releasing agent to a subject, of those the subject was, is and/or will be administrated a VEGFR inhibitor and/or VEGF inhibitor, and suffer or susceptible to suffer the disease or disorder associated with administration of a VEGFR inhibitor and/or VEGF inhibitor.

The present application further provides a method comprising administrating nitric oxide releasing agent to a subject suffering or susceptible to suffer the disease or disorder, of those the subject was, is and/or will be administrated a VEGFR inhibitor and/or VEGF inhibitor.

As used herein, the subject may have suffered the disease or disorder associated with administration of the VEGFR inhibitor and/or VEGF inhibitor, or, the subject may have greater probability to suffer the disease or disorder associated with administration of the VEGFR inhibitor and/or VEGF inhibitor.

As used herein, the term "susceptible to" generally refer to a subject have a greater probability to suffer a disease or disorder associated with administration of a VEGFR inhibitor and/or VEGF inhibitor. For instance, the greater probability may refer to the probability of a subject suffering the disease or disorder associated with administration of a VEGFR inhibitor and/or VEGF inhibitor increases by about at least 10%, at least 20%, at least 30%, at least 40%, at least 50%, at least 60%, at least 70%, at least 80%, at least 90%, at least 100%, at least 150%, at least 200% or higher, compared with that of a health subject.

The present application further provides a method of preventing or treating diseases or disorders, comprising administrating a nitric oxide releasing agent to a subject that suffers or susceptible to the disease or disorder, of those the disease or disorder is hand-food syndrome.

For instance, the subject may have been, is or will be administrated with a VEGFR inhibitor and/or VEGF inhibitor.

For instance, the disease or disorder may be hand-foot syndrome. For instance, the disease or disorder may be a disease or disorder associated with administration of the VEGFR inhibitor and/or VEGF inhibitor. For instance, the disease or disorder may be a hand-foot syndrome associated with administration of the VEGFR inhibitor and/or VEGF inhibitor.

The present application provides a method comprising the steps of: 1) monitoring one or more features of skin tissue, facial organ and/or gastrointestinal tract of a subject administrated a VEGFR inhibitor and/or VEGF inhibitor; 2) when the monitoring shows the subject suffer skin tissue disease or disorder, facial organ disease or disorder and/or gastrointestinal disease or disorder associated with administration of the VEGFR inhibitor and/or VEGF inhibitor, administrating the nitric oxide releasing agent to the subject.

As used herein, the term "features of skin tissue" generally refers to features capable of representing skin tissue disease or disorder. For instance, the features may comprise features capable of representing a disease or disorder associated with administration of the VEGFR inhibitor and/or VEGF inhibitor. For instance, the feature may comprise feature capable of representing rash associated with administration of the VEGFR inhibitor and/or VEGF inhibitor, hand-foot syndrome associated with administration of the VEGFR inhibitor and/or VEGF inhibitor, pruritus associated with administration of the VEGFR inhibitor and/or VEGF inhibitor, erythema and/or purpura associated with administration of the VEGFR inhibitor and/or VEGF inhibitor, xerosis cutis and/or chapped associated with administration of the VEGFR inhibitor and/or VEGF inhibitor, alopecia associated with administration of the VEGFR inhibitor and/or VEGF inhibitor, paronychia associated with administration of the VEGFR inhibitor and/or VEGF inhibitor, and/or pigmentation disorder associated with administration of the VEGFR inhibitor and/or VEGF inhibitor. For instance, the feature may comprise area and degree of erythema, the area and degree of purpura, the numbers and degree of pimples, the numbers and degree of pustule, the numbers and degree of nodule, the range and degree of skin swelling, the degree of skin ulcer, degree of xerosis, degree of skin chapped, degree of skin keratinization, degree of skin lichen, the area and degree of skin desquamation, state of skin tight, degree of skin pruritus, degree of vascular inflammation between dermis with hypodermic, the degree of necrotic skin tissue, the degree of skin ulcer, the area of livedo reticularis, the degree of skin pigmentation, the numbers of blister and bullae, part/area/degree of alopecia, degree of skin granulation, degree of skin seborrhea, degree of folliculitis, the degree of periungual swelling and redness, the degree of paronychia, the pigmentation of periungual skin, the degree of onychatrophia, onychatrophia or onychauxis, abnormal color of nail bed, nail stripe, nail ridge, nail pterygium and of like.

As used herein, the term "features of facial organ" generally refers to the features representing facial disease or disorder. For instance, the features may comprise the features representing the disease or disorder associated with administration of a VEGFR inhibitor and/or VEGF inhibitor. For instance, the features may comprise the features representing. The feature may comprise feature capable of representing a disease or disorder associated with administration of a VEGFR inhibitor and/or VEGF inhibitor. For instance, the feature may comprise feature capable of representing an oral mucositis associated with administration of a VEGFR inhibitor and/or VEGF inhibitor, xerostomia associated with administration of a VEGFR inhibitor and/or VEGF inhibitor, epistaxis associated with administration of a VEGFR inhibitor and/or VEGF inhibitor, nasopharyngitis associated with administration of a VEGFR inhibitor and/or VEGF inhibitor, and/or cheilitis associated with administration of a VEGFR inhibitor and/or VEGF inhibitor. For instance, the feature may comprise congestion degree of oral mucosa, edema degree of oral mucosa, herpes degree of oral mucosa, ulcer degree of oral mucosa, degree of oral submucosa glandular defect, degree of lingual gland/sublingual gland/parotid gland and atrophy, the degree of xerostomia, the degree of caries, the degree of tongue swelling, the degree of peripheral tooth mark, frequency of nosebleed, the amount of nosebleed, degree of oropharynx and nasopharynx mucosal edema, degree of oropharynx and nasopharynx mucosal herpes, degree of oropharynx and nasopharynx mucosal ulcer, degree of oropharynx and nasopharynx mucosal hyperplasia, degree of oropharynx and nasopharynx follicular hyperplasia, the degree of lip and around-lip swelling, the degree of lip and around-lip herpes, degree of lip and around-lip erythema, degree of lip and around-lip skin desquamation, degree of lip and around-lip skin lichenification and the degree of lip and around-lip skin erosion and of like.

As used herein, the term "features of gastrointestinal tract" generally refers to feature capable of representing gastrointestinal disease or disorder. For instance, the feature may comprise feature capable of representing a disease or disorder associated with administration of a VEGFR inhibitor and/or VEGF inhibitor. For instance, the feature may comprise capable of representing an esophagitis associated with administration of the VEGFR inhibitor and/or VEGF inhibitor, esogastritis associated with administration of the VEGFR inhibitor and/or VEGF inhibitor, gastric ulcer associated with administration of the VEGFR inhibitor and/or VEGF inhibitor, diarrhea associated with administration of the VEGFR inhibitor and/or VEGF inhibitor, vomiting associated with administration of the VEGFR inhibitor and/or VEGF inhibitor, nausea associated with administration of the VEGFR inhibitor and/or VEGF inhibitor, anorexia associated with administration of the VEGFR inhibitor and/or VEGF inhibitor, constipation associated with administration of the VEGFR inhibitor and/or VEGF inhibitor, and/or abdominal pain associated with administration of the VEGFR inhibitor and/or VEGF inhibitor. For instance, the feature may comprise degree of appetite loss, degree of stomach belching, degree of swallowing hard, degree of burning sensation of the sternum, degree of sternal pain, time and degree of upper abdominal pain (when hungry or satiety), degree of bloating, degree of diarrhea, numbers of defecation, defecation time, abdominal pain before defecation, rectal tenesmus, abnormal defecation (such as black-blood stool, fresh-blood stool, mucus stool, mucus-blood stool, watery stool, egg-dropping stool, etc.), vomiting frequency, vomitus situation, nausea, degree of malnutrition, degree of micronutrient deficiency, etc.

As used herein, the method comprises continually monitoring the skin tissue disease or disorder, facial organ disease or disorder and/or gastrointestinal disease or disorder, and optionally reducing or withdrawing the VEGFR inhibitor and/or VEGF inhibitor. For instance, the continually monitoring may refer to monitoring for about at least one day, at least one week, at least ten days, at least two weeks, at least three weeks, at least one month, at least three months, or longer after administration of the VEGFR inhibitor and/or VEGF inhibitor. For instance, the reducing or withdrawing may refer to reducing the dosage of the VEGFR inhibitor and/or VEGF inhibitor administered to the subject by about at least 5%, at least 10%, at least 20%, at least 30%, at least 40%, at least 50%, at least 60%, at least 70%, at least 80%, at least 90%, at least 95%, at least 99% or 100%, comparing with the dosage of the VEGFR inhibitor and/or VEGF inhibitor administered in step 1) of the method.

As used herein, the severity of the disease or disorder associated with administration of the VEGFR inhibitor and/or VEGF inhibitor may increase after the administration of VEGFR inhibitor and/or VEGF inhibitor. For instance, the severity may increase by at least 5%, at least 10%, at least 20%, at least 30%, at least 40%, at least 50%, at least 60%, at least 70%, at least 80%, at least 90% or more.

As used herein, the subject may not suffer the disease or disorder before administrating the VEGFR inhibitor and/or VEGF inhibitor.

As used herein, the VEGFR inhibitor and/or VEGF inhibitor may not comprise the nitric oxide releasing agent. For instance, the VEGFR inhibitor and/or VEGF inhibitor may not comprise nitroglycerin.

As used herein, the disease or disorder may be epithelial tissue disease or disorder.

As used herein, the administration of the VEGFR inhibitor and/or VEGF inhibitor may be used to treat cancer. For instance, the location of the disease or disorder may be different from that of tumor.

As used herein, the nitric oxide releasing agent may be administrated to the subject. For instance, the nitric oxide releasing agent may be administrated topically to the location substantially not comprising tumor cells. As used herein, it may administrate the nitric oxide releasing agent to the subject topically. For instance, it may administrate the nitric oxide releasing agent to the subject at a site that substantially doesn't comprise tumor cells.

As used herein, the item "the location substantially not comprising tumor cells" generally refer to a tissue organ or location where the amount of cancer cell is low enough to be reckoned as substantially not comprised. For instance, the substantially not comprise may refer to the amount of cancer cells is less than 0.01%, less than 0.005%, less than 0.001%, less than 0.0001%, less than 0.00001% or less of the amount of overall cells of this location.

For another instance, it may administrate the nitric oxide releasing agent to a no-cancer location.

As used herein, the term of "no-cancer location" generally refer to a site that is not a cancer nidus or cancer metastasis site. For instance, the cancer nodus may be a primary site of a cancer. For instance, the cancer metastasis site may be a place of the same tumor as the tumor of the primary site. For instance, the cancer metastasis site may be formed by a lymphatic metastasis, vascular metastasis or transcoelomic metastasis.

In the context of the present invention (especially in the context of the following claims, unless otherwise stated herein or clearly contradictory to the context, the terms "a" and "an" and "the" and "at least a/an/one" and similar referents are to be understood as comprising both singular and plural forms. Unless otherwise stated herein or clearly contradictory to the context, when the term "at least one" is followed by one or more of items as listed (for example, "at least one of A and B"), it is to be understood as one of the listed items (A or B) or any combination of two or more of the listed items (A and B).

Unless otherwise noted, the terms "comprise," "have," "include," and "contain," are intended to mean an open term (i.e., meaning "including, but not limited to").

It is not intended to be bound by any theory, the examples as set forth below are merely for the purpose of illustrating the working modes of the apparatus, method and system of the present application, but not to limit the scope of the invention.

EXAMPLES

In the results of the examples of the present application, represents $P<0.01$; * represents $P<0.05$; *** represents $P<0.001$, as statistically detected by using t-test.

Example 1: Synthesis of S-Nitrosothiol Silica Nanospheres

A mixed solution of 4 ml of (3-mercaptopropyl) trimethoxysilane and 2 ml of tetraethyl orthosilicate was injected via an injection pump to a mixed solution of 30 ml of deionized water, 30 ml of ethanol and 30 ml of ammonia water at a rate of 0.5 ml/min. During injection, the reaction mixture was kept at 0° C. After completion of injection, the reaction mixture was stirred at room temperature for 2.5 hrs., and then centrifuged at 4000 rpm for 8 min. The precipitates were washed once with 100 ml of ice water and 100 ml of ethanol respectively, and dried under vacuum to give thiolated silica nanospheres.

150 mg thiolated silica nanosphere was dispersed in 4 ml of methanol, and cooled to 0° C. A mixed solution of 2 ml of 1 M sodium nitrite and 1 mM diethyltriaminepentaacetic acid was added under constant stirring, and then 2 ml of 5 M aqueous solution of hydrochloric acid was added. The reaction mixture was stirred in the dark at 0° C. for 2.5 hrs., centrifuged at 4° C. at 4000 rpm for 5 mins. The precipitates were washed once with 30 ml of 1 mM aqueous solution of diethyltriaminepentaacetic acid at 4° C. and 30 ml of methanol at 4° C. respectively, and centrifuged again for collecting the solid. In the dark and at a temperature below −30° C., the solid was dried over under vacuum for 30 mins to give the dried final product, which was stored at −20° C. for next use.

The final product was dissolved in a PBS buffer solution of pH=7.4, and it was measured by using ZS90 Type Particle Size and Zeta Potential Analyzer that the hydrodynamic radius of the product was 423 nm and the polydispersity index was 0.061. The UV-visible spectrum of the solution (as measured by using Thermo Fisher EV300 Type UV spectrophotometer) has a characteristic absorption peak at 330 nm. Under the conditions of 200 W light for 5 hrs., the NO storage was characterized by the total amount of the released nitric oxide as detected by Beyotime NO assay kit (Griess Method, purchased from Shanghai Beyotime Biotechnology Inc.). The NO storage of the final product was measured to be 1.87±0.55 μmol/mg.

Example 2: Synthesis of S-Nitrosoethanedithiol Chitin 2 g of chitin and 5 g of lithium chloride were dispersed in 50 ml of dimethylacetamide, and 20 ml of N,N-diisopropylethylamine was added at 0° C. 20 g of p-toluenesulfonyl chloride was dissolved in 20 ml of dimethylacetamide, and the resultant mixture was added into the chitin-containing solution as prepared above. The mixed solution was stirred at 4° C. for 20 hrs., and then poured into 300 ml of acetone for precipitation and filtration. The precipitates were washed once with 300 ml of methanol, 150 ml of DI water and 300 ml of acetone respectively, and then dried over under vacuum to give p-tosylated chitin.

1 g of p-tosylated chitin and 2.5 g of lithium chloride were dispersed into 40 ml of dimethylacetamide, and then 3 ml of N,N-diisopropylethylamine and 1.5 ml of 1,2-ethanedithiol were added. The mixed solution was stirred at 60° C. under nitrogen for 24 hrs, and then poured into 400 ml of acetone for precipitation and filtration. The precipitates were washed with 400 ml of methanol and 400 ml of acetone respectively, dried over under vacuum, and then dispersed into a 25 ml solution of 10 mM 1,4-dithiothreitol and N,N-diisopropylethylamine in dimethylacetamide. The reaction mixture was stirred at room temperature for 1 hr, and filtered. The precipitates were washed once with 400 ml of methanol and 400 ml of acetone respectively, and dried over under vacuum to give thiolated chitin compound. 200 mg thiolated chitin compound was dispersed into a 5 ml mixed solution of dimethylacetamide/methanol (at a volume ratio of 3/1), and 1 ml of tert-butyl nitrite was added and stirred at room temperature for 12 hrs. Then, the mixed solution was added in to 100 ml of methanol and stirred for 30 mins, filtered, and dried under vacuum to give the final product.

The infrared spectroscopy of the final product (as detected by Nicolet 6700 Type infrared spectrometer) has main absorption peaks (wave numbers): 3600-3200, 3285, 1652, 1537, 1028, 3360-3220, 1250-1300, 1050-1070. The diffuse reflectance UV-visible spectrum thereof (as detected by using Thermo Fisher EV300 Type UV spectrophotometer) shows a characteristic absorption peak at 549 nm. Under the conditions of 200 W light for 5 hrs, the NO storage was characterized by the total amount of the released nitric oxide as detected by Beyotime NO assay kit (Griess Method, purchased from Shanghai Beyotime Biotechnology Inc.). The NO storage of the final product was measured to be 0.37±0.08 μmol/mg.

Example 3: Synthesis of Oligopropylenediamine-Grafted Chitosan NONOate

250 μL of 2-methylaziridine was mixed with 300 μL of 1 M aqueous solution of hydrochloride, and the mixture was added dropwise into 10 ml of 20 mg/mL chitosan aqueous solution. The mixed solution was stirred at room temperature for 4 days and at 78° C. for 20 hrs, and then poured into 300 ml of acetone for precipitation and centrifugation. The precipitates were washed twice with methanol, and dried over under vacuum to give secondary amine modified chitosan. NMR spectroscopy (by using Bruker Avance III Type NMR spectrometer, 400 MHz, $CD_3OD$) shows peaks at 0.8-1.1, 1.9, 2.3-2.7, 3.3-4.0, and 4.4.

50 mg secondary amine modified chitosan was dissolved in a mixed solution of 1 mL of water and 3 mL of methanol, and the mixed solution was added into Parr swing hydrogenator, together with 100 μL of 6 M solution of sodium methoxide. The hydrogenator was repeatedly purged with high purity nitrogen to remove oxygen, filled with gaseous nitric oxide, and kept at 10 atm at room temperature for 4 days for reaction. After completion of reaction, the reaction vessel was repeatedly purged with high purity nitrogen to remove unreacted nitric oxide. Then, the reaction mixture was added into 300 mL of acetone for precipitation, centrifuged to collect the precipitates, and dried under vacuum to give the final product, which was stored at −20° C. for next use.

The infrared spectrum of the final product (comprise diazeniumdiolate) (as detected by using Nicolet 6700 Type infrared spectrometer) comprises main absorption peaks (wave numbers) of: 3600-3200, 3285, 1650, 1587, 1284, and 1059. The UV-visible spectrum thereof (as detected by using Thermo Fisher EV300 Type UV spectrophotometer) comprises a characteristic absorption peak at 252 nm. The sample was dissolved in a PBS solution, and detected by Beyotime NO assay kit (Griess Method) for the total NO releasing amount, so as to determine that the NO storage of the sample which was 0.77±0.11 μmol/mL.

Examples 4-15: Effect of Nitric Oxide Releasing Agent on Ameliorating Proliferative Toxicity of VEGF/VEGFR Inhibitor to HUVEC Cells and Comparison with Sildenafil It was tried to use Sildenafil to treat the side effect of Palmar Plantar Erythrodysesthesia (PPE) caused by anti-VEGF multi-kinase inhibitor as reported (see, Kellen L. Meadows et al., *Support Care Cancer.* 2015 May 23 (5): 1311-1319) However, the therapeutic effect of Sildenafil against PPE caused by anti-VEGF multi-kinase inhibitors is very limited, almost ineffective. In the present application, the effect of the nitric oxide releasing agent is compared with that of Sildenafil.

The cultured HUVEC cells were digested, suspended, counted and seeded into a 96-well plate with 5000-10000 cells per well. The wells were divided to: the blank control group, the VEGF/VEGFR inhibitor group, the VEGF/VEGFR inhibitor+nitric oxide releasing agent group, the VEGF/VEGFR inhibitor solvent group, the nitric oxide releasing agent solvent control group, the VEGF/VEGFR inhibitor+sildenafil group, and sildenafil solvent control group, wherein each well of each group contained a basic medium, and the final liquid volume contained in each well was about 100 μL. The particular grouping situation was as follows:

1) the blank control group: no solution was added except normally replacing the medium;
2) the VEGF/VEGFR inhibitor group: a VEGF/VEGFR inhibitor solution (the final concentration was shown in Table 1, and the solvent of the VEGF/VEGFR inhibitor solution was DMSO);
3) the VEGF/VEGFR inhibitor+nitric oxide releasing agent group: a VEGF/VEGFR inhibitor solution and a nitric oxide releasing agent solution were added (the final concentrations of the VEGF/VEGFR inhibitor and the nitric oxide releasing agent were shown in Table 1, the solvent of the nitric oxide releasing agent solution was selected as ethanol or sterile water depending on the solubility of the nitric oxide releasing agent, and the slight difference of the total volume of each group was complemented by adding the corresponding solvent as selected);
4) the VEGF/VEGFR inhibitor solvent group: an equal volume of DMSO as contained in the corresponding VEGF/VEGFR inhibitor solution in Group 2) was added;
5) the nitric oxide releasing agent solvent control group: an equal volume of the same type of solvent (e.g., ethanol or sterile water) as contained in the corresponding nitric oxide releasing agent solution in Group 3);

6) the VEGF/VEGFR inhibitor+Sildenafil group: a VEGF/VEGFR inhibitor solution was first added, and then a Sildenafil solution was added (the final concentrations of the VEGF/VEGFR inhibitor and Sildenafil were shown in Table 2, the solvent of the Sildenafil solution was DMSO, and the slight difference of the total volume of each group was complemented by adding the corresponding solvent as selected);

7) the Sildenafil solvent control group: an equal volume of DMSO as contained in the corresponding Sildenafil solution in Group 6) was added.

The VEGF/VEGFR inhibitor solvent group was not subject to data processing, and only served as a reference for evaluating the system error of experiments. The nitric oxide releasing agent solvent control group and the Sildenafil solvent control group were used for data correction, thereby eliminating the effect of solvents on results.

After cultured for additional 24-48 hours, the survival rate of cells was determined by Cell Counting Kit-8 (CCK-8) assay kit (C0037, Shanghai Beyotime Biotechnology Inc., Beyotime Biotechnology), to calculate the amelioration effect of VEGF/VEGFR inhibitor to proliferative toxicity and the ameliorating effect of the nitric oxide releasing agent or Sildenafil to the proliferative toxicity. GraphPad Prism 6.0 Software and t-test were used to carry out a statistic analysis of the results and plot a graph.

Figure 4:
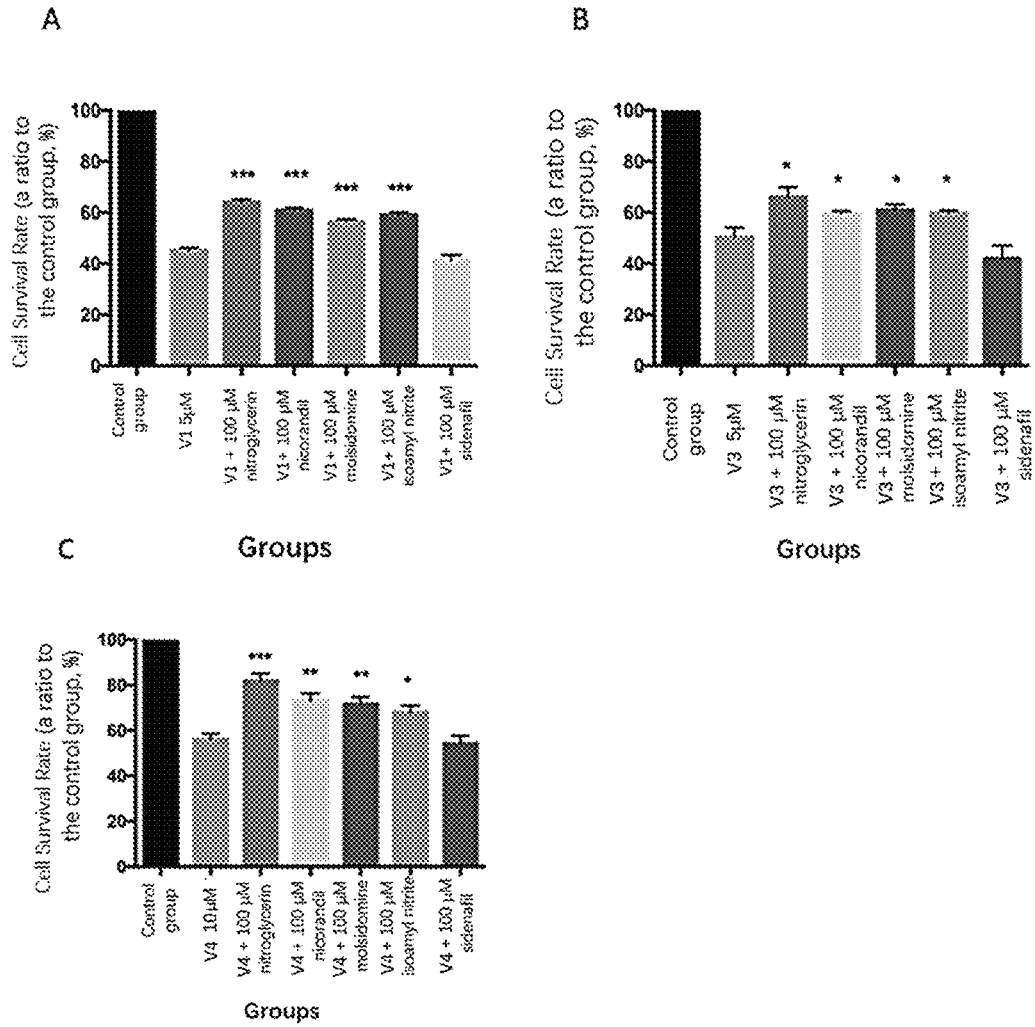
FIGS. 4A-4C depict an exemplary result of cell proliferative toxicity as determined after administration of a nitric oxide releasing agent (or sildenafil) to HUVEC cells.

Table 2 lists various combinations of the VEGF/VEGFR inhibitor with the nitric oxide releasing agent or Sildenafil, and the corresponding experimental results (wherein, the data as listed in the cell survival rate column were the percentages of viable cells increased by the VEGF/VEGFR inhibitor+nitric oxide releasing agent group (or Sildenafil), as compared to the VEGF/VEGFR inhibitor group). FIG. 4A-4C represent the exemplary results of cell proliferative toxicity as determined by the CCK-8 method after 24 hours from the administration of the VEGF/VEGFR inhibitor sorafenib tosylate (V1) or Sunitinib malate (V3) or Regorafenib (V4) and the nitric oxide releasing agent (or Sildenafil) to the HUVEC cells, respectively. Of those, the horizontal axis represents different experiment groups and control groups, and the vertical axis represents the cell survival rate (the survival percentage of other experimental groups or solvent control groups is calculated based on 100% of the cell survival rate of the blank control group). Of those, represents $P<0.001$; ** represents $P<0.01$, indicating that it has significant difference from the corresponding group in which the VEGF/VEGFR inhibitor is administered alone; * represents $P<0.05$, indicating that it has significant difference from the corresponding group in which the VEGF/VEGFR inhibitor is administered alone; as statistically detected by using t-test.

TABLE 2

Experimental Conditions and Results of Examples 4-15

| Ex No. | VEGFR inhibitor | Final Concentration | Nitric oxide releasing agent | Final Concentration | Cell Survival Rate |
|---|---|---|---|---|---|
| 4 | Sorafenib | 5 μM | Nitroglycerin | 100 μM | Increased by 50-60% |
|  | Apatinib | 10 μM |  |  | Increased by 60-70% |
|  | Sunitinib | 5 μM |  |  | Increased by 50-60% |
|  | Regorafenib | 10 μM |  |  | Increased by 30-40% |
|  | Lenvatinib Mesylate | 10 μM |  |  | Increased by 30-50% |
|  | Pazopanib | 10 μM |  |  | Increased by 20-30% |
|  | Axitinib | 10 μM |  |  | Increased by 20-30% |
|  | Nintedanib Esylate | 10 μM |  |  | Increased by 30-50% |
|  | Thalidomide | 10 μM |  |  | Increased by 20-30% |
| 5 | Sorafenib | 5 μM | Molsidomine | 100 μM | Increased by 30-40% |
|  | Apatinib | 10 μM |  |  | Increased by 40-50% |
|  | Sunitinib | 5 μM |  |  | Increased by 20-30% |
|  | Regorafenib | 10 μM |  |  | Increased by 20-30% |
|  | Lenvatinib Mesylate |  |  |  | Increased by 30-50% |
|  | Pazopanib Hydrochloride |  |  |  | Increased by 20-30% |
|  | Axitinib |  |  |  | Increased by 20-30% |
|  | Nintedanib Esylate |  |  |  | Increased by 30-50% |
|  | Thalidomide |  |  |  | Increased by 20-30% |
| 6 | Sorafenib | 5 μM | Nicorandil | 100 μM | Increased by 50-60% |
|  | Regorafenib | 10 μM |  |  | Increased by 20-30% |
|  | Sunitinib | 5 μM |  |  | Increased by 10-20% |
|  | Lenvatinib Mesylate | 10 μM |  |  | Increased by 30-50% |
|  | Pazopanib Hydrochloride |  |  |  | Increased by 20-30% |
|  | Axitinib |  |  |  | Increased by 20-30% |
|  | Nintedanib Esylate |  |  |  | Increased by 30-50% |
|  | Thalidomide |  |  |  | Increased by 20-30% |
|  | Apatinib |  |  |  | Increased by 40-50% |
| 7 | Sorafenib | 5 μM | Isoamyl Nitrite | 100 μM | Increased by 30-40% |
|  | Sunitinib | 5 μM |  |  | Increased by 20-25% |
|  | Regorafenib | 10 μM |  |  | Increased by 15-20% |
|  | Lenvatinib Mesylate | 10 μM |  |  | Increased by 30-50% |
|  | Pazopanib Hydrochloride |  |  |  | Increased by 20-30% |
|  | Axitinib |  |  |  | Increased by 20-30% |
|  | Nintedanib Esylate |  |  |  | Increased by 30-50% |
|  | Thalidomide |  |  |  | Increased by 20-30% |
|  | Apatinib |  |  |  | Increased by 40-50% |
| 8 | Regorafenib | 10 μM | Isosorbide Dinitrate | 100 μM | Increased by 15-20% |
|  | Sunitinib | 5 μM |  |  | Increased by 20-30% |
|  | Sorafenib | 5 μM |  |  | Increased by 20-30% |
| 9 | Regorafenib | 10 μM | 3-morpholinosydnonimine (SIN-1) linsidomine | 100 μM | Increased by 15-20% |

TABLE 2-continued

Experimental Conditions and Results of Examples 4-15

| Ex No. | VEGFR inhibitor | Final Concentration | Nitric oxide releasing agent | Final Concentration | Cell Survival Rate |
|---|---|---|---|---|---|
|  | Sunitinib | 5 μM |  |  | Increased by 10-20% |
|  | Sorafenib | 5 μM |  |  | Increased by 30-40% |
| 10 | Regorafenib | 10 μM | Isosorbide Mononitrate | 100 μM | Increased by 20-30% |
|  | Sunitinib | 5 μM |  |  | Increased by 20-25% |
|  | Sorafenib | 5 μM |  |  | Increased by 30-35% |
| 11 | Regorafenib | 10 μM | Pentaerythritol Tetranitrate | 100 μM | Increased by 20-25% |
|  | Sunitinib | 5 μM |  |  | Increased by 25-35% |
|  | Sorafenib | 5 μM |  |  | Increased by 30-40% |
| 12 | Regorafenib | 10 μM | 3,3-Bis (aminoethyl)-1-hydroxy-2-oxo-1-triazene (NOC-18) | 100 μM | Increased by 15-20% |
|  | Sunitinib | 5 μM |  |  | Increased by 20-30% |
|  | Sorafenib | 5 μM |  |  | Increased by 35-45% |
| 13 | Regorafenib | 10 μM | S-nitrosothiol silica nanospheres | 0.30 mg/mL | Increased by 10-30% |
|  | Sunitinib | 5 μM |  |  | Increased by 15-30% |
|  | Sorafenib | 5 μM |  |  | Increased by 20-25% |
| 14 | Regorafenib | 10 μM | Oligopropylenediamine-grafted chitosan NONOate | 1.80 mg/mL | Increased by 20-25% |
|  | Sunitinib | 5 μM |  |  | Increased by 20-30% |
|  | Sorafenib | 5 μM |  |  | Increased by 30-50% |
| 15 | Regorafenib | 10 μM |  |  | No significant change |
|  | Sunitinib | 5 μM | Sildenafil | 100 μM |  |
|  | Sorafenib | 5 μM |  |  |  |

It can be seen form the results in Table 2 and FIG. 4A-4C that the nitric oxide releasing agents produce a significantly ameliorating effect on the proliferative toxicity, and the ameliorating effect thereof is substantially better than Sildenafil.

Examples 16-32: Effect of Nitric Oxide Releasing Agent on Ameliorating Proliferative Toxicity of VEGF/VEGFR Inhibitor to Human Immortalized Epithelial Cells (HaCaT), Human Oral Mucosa Epithelial Keratinocytes (HOK), Human Small Intestinal Epithelial Cells (FHs 74 Int), Gastric Epithelial Cells (GES-1) and Comparison with Sildenafil A variety of epithelial cells were cultured for use in experiments, wherein: Examples 16-20 utilized human immortalized epithelial cells (HaCaT), and the results correspond to Table 3; Examples 21-24 utilized human oral mucosa epithelial keratinocytes (HOK), and the results correspond to Table 4; Examples 25-28 utilized gastric epithelial cells (GES-1), and the results correspond to Table 5; Examples 29-32 utilized human small intestinal epithelial cells (FHs 74 Int), and the results correspond to Table 6.

The cultured cells were digested, suspended, counted, and seeded into a 96-well plate with 5000-10000 cells per well. The wells were divided to: the blank control group, the VEGF/VEGFR inhibitor group, the VEGF/VEGFR inhibitor+nitric oxide releasing agent group, the VEGF/VEGFR inhibitor solvent group, the nitric oxide releasing agent solvent control group, the VEGF/VEGFR inhibitor+Sildenafil group, and Sildenafil solvent control group, wherein each well of each group contained a basic medium, and the final liquid volume contained in each well was about 100 μL. The particular grouping situation was as follows:

1) the blank control group: no solution was added except normally replacing the medium;
2) the VEGF/VEGFR inhibitor group: a VEGF/VEGFR inhibitor solution (the final concentration was shown in Table 2, and the solvent of the VEGF/VEGFR inhibitor solution was DMSO);
3) the VEGF/VEGFR inhibitor+nitric oxide releasing agent group: a VEGF/VEGFR inhibitor solution and a nitric oxide releasing agent solution were added (the final concentrations of the VEGF/VEGFR inhibitor and the nitric oxide releasing agent were shown in Table 2, the solvent of the nitric oxide releasing agent solution was selected as ethanol or sterile water depending on the solubility of the nitric oxide releasing agent, and the slight difference of the total volume of each group was complemented by adding the corresponding solvent as selected);
4) the VEGF/VEGFR inhibitor solvent group: an equal volume of DMSO as contained in the corresponding VEGF/VEGFR inhibitor solution in Group 2) was added;
5) the nitric oxide releasing agent solvent control group: an equal volume of the same type of solvent (e.g., ethanol or sterile water) as contained in the corresponding nitric oxide releasing agent solution in Group 3);
6) the VEGF/VEGFR inhibitor+sildenafil group: a VEGF/VEGFR inhibitor solution was first added, and then a Sildenafil solution was added (the final concentrations of the VEGF/VEGFR inhibitor and Sildenafil were shown in Table 2, the solvent of the Sildenafil solution was DMSO, and the slight difference of the total volume of each group was complemented by adding the corresponding solvent as selected);
7) the Sildenafil solvent control group: an equal volume of DMSO as contained in the corresponding sildenafil solution in Group 6) was added.

The VEGF/VEGFR inhibitor solvent group was not subject to data processing, and only served as a reference for evaluating the system error of experiments. The nitric oxide releasing agent solvent control group and the sildenafil solvent control group were used for data correction, thereby eliminating the effect of solvents on results.

After cultured for additional 24-48 hours, the survival of cells was determined by Cell Counting Kit-8 (CCK-8) assay kit (C0037, Shanghai Beyotime Biotechnology Inc., Beyotime Biotechnology), to calculate the proliferative toxicity of the VEGF/VEGFR inhibitor to cells and the ameliorating effect of the nitric oxide releasing agent to the proliferative toxicity. GraphPad Prism 6.0 Software and t-test were used to carry out a statistic analysis of the results and plot a graph.

Figure 5:
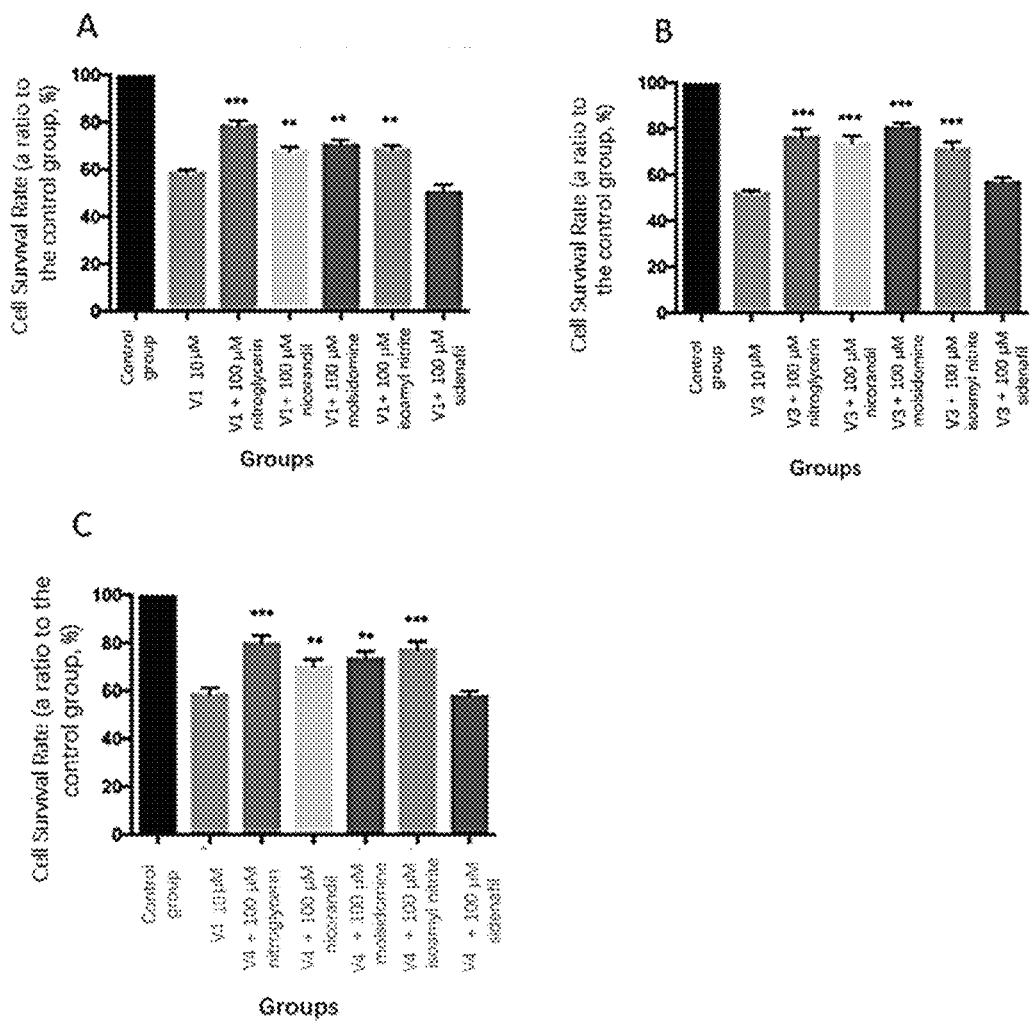
FIGS. 5A-5C depict an exemplary result of cell proliferative toxicity as determined after administration of a nitric oxide releasing agent (or sildenafil) to HaCaT cells.
Figure 6:
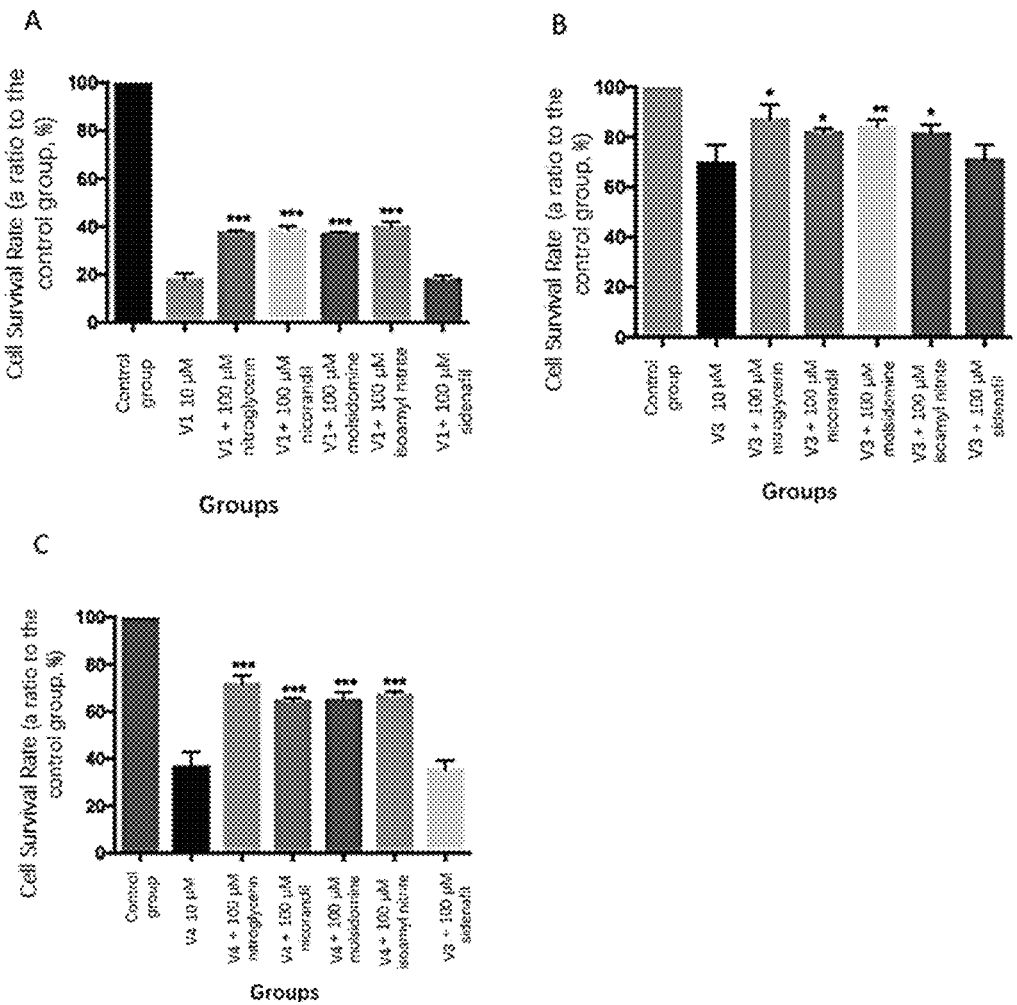
FIGS. 6A-6C depict an exemplary result of cell proliferative toxicity as determined after administration of a nitric oxide releasing agent (or sildenafil) to HOK cells.
Figure 7:
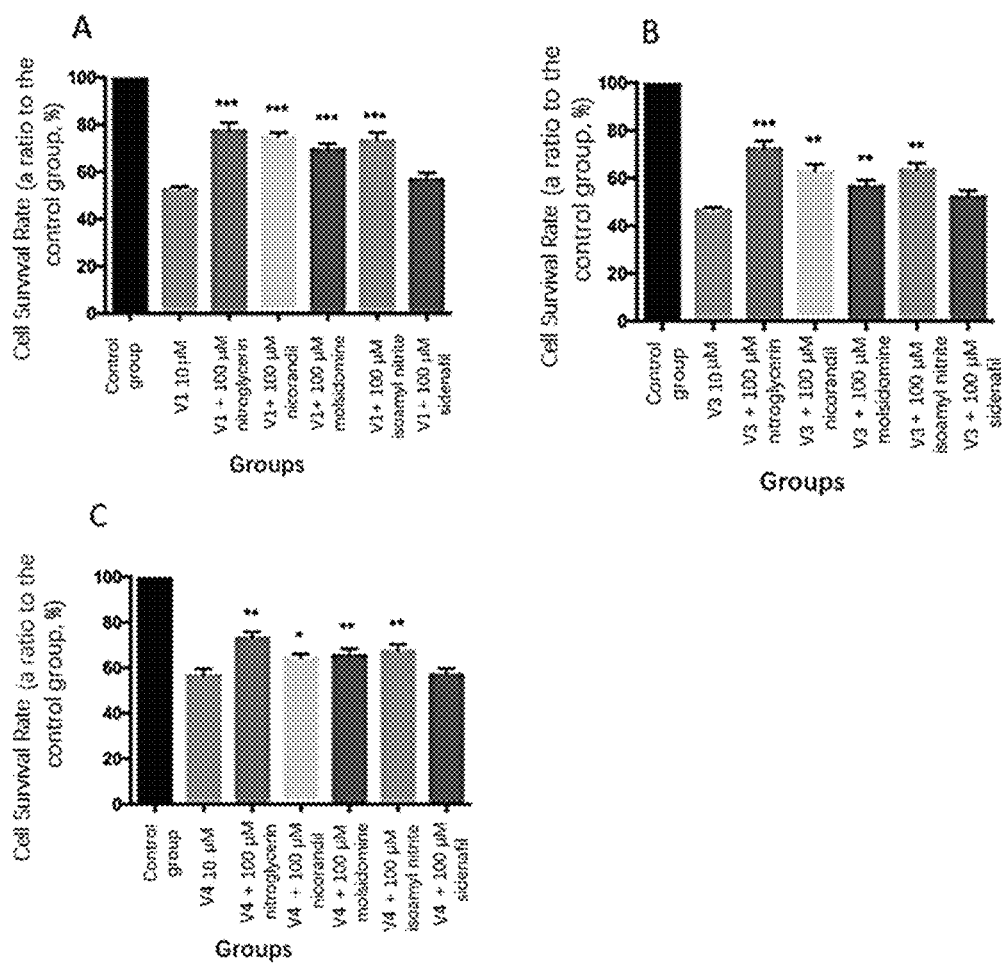
FIGS. 7A-7C depict an exemplary result of cell proliferative toxicity as determined after administration of a nitric oxide releasing agent (or sildenafil) to GES-1 cells.
Figure 8:
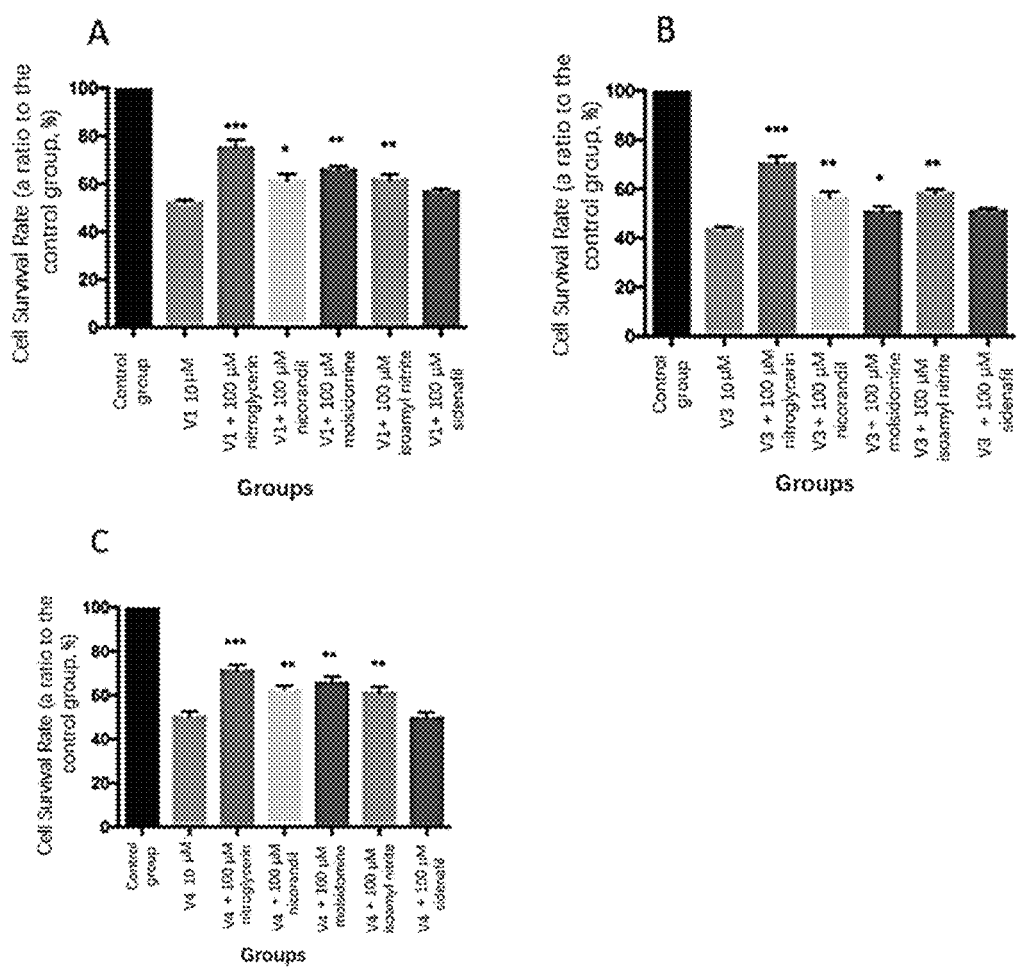
FIGS. 8A-8C depict an exemplary result of cell proliferative toxicity as determined after administration of a nitric oxide releasing agent (or sildenafil) to FHs 74 Int cells.

Tables 3-6 list various combinations of the VEGF/VEGFR inhibitor and the nitric oxide releasing agent or Sildenafil, and the corresponding experimental results (wherein, the data as listed in the cell survival rate column were the percentages of viable cells increased by the VEGF/VEGFR inhibitor+nitric oxide releasing agent group (or Sildenafil), as compared to the VEGF/VEGFR inhibitor group). FIG. 5 represents the experimental results on HaCaT cells, FIG. 6 represents the experimental results on HOK cells, FIG. 7 represents the experimental results on GES-1 cells, FIG. 8 represents the experimental results on FHs 74 Int cells. Of those, the horizontal axis represents the experimental results on different experimental groups and control groups; and the vertical axis represents the survival rate of cells (the survival percentage of cells in other experimental groups or solvent control group is calculated based on 100% of the cell survival rate of the blank control group) wherein FIGS. 5A, 6A, 7A and 8A each represents the exemplary results of cell proliferative toxicity as determined by the CCK-8 method after 24 hours from the administration of the VEGF/VEGFR inhibitor Sorafenib tosylate (V1) and the nitric oxide releasing agent (or Sildenafil) to different types of cells; FIGS. 5B, 6B, 7B and 8B each represents the exemplary results of cell proliferative toxicity as determined by the CKK-8 method after 24 hours from the administration of the VEGF/VEGFR inhibitor Sunitinib malate (V3) and the nitric oxide releasing agent (or Sildenafil) to different types of cells; and FIGS. 5C, 6C, 7C and 8C each represent the exemplary results of cell proliferative toxicity as determined by the CKK-8 method after 24 hours from the administration of the VEGF/VEGFR inhibitor Regorafenib (V4) and the nitric oxide releasing agent (or Sildenafil) to different types of cells. Of those, *** represents $P<0.001$, indicating a significant difference as compared with the control group which is administered with the VEGF/VEGFR inhibitor alone; represents $P<0.01$, indicating a significant difference as compared with the control group which is administered with the VEGF/VEGFR inhibitor alone; * represents $P<0.05$, indicating a significant difference as compared with the control group which is administered with the VEGF/VEGFR inhibitor alone; as statistically detected by using t-test.

TABLE 3

Experimental Conditions and Results of Examples 16-20

| Ex. No. | VEGFR Inhibitor | Final Concentration | Nitric Oxide Releasing Agent | Final Concentration | Cell Survival Rate |
|---|---|---|---|---|---|
| 16 | Sorafenib | 10 μM | Isoamyl Nitrite | 100 μM | Increased by 15-20% |
|  | Regorafenib | 10 μM |  |  | Increased by 28-35% |
|  | Sunitinib | 10 μM |  |  | Increased by 35-45% |
| 17 | Sorafenib | 10 μM | Molsidomine | 100 μM | Increased by 15-20% |
|  | Regorafenib | 10 μM |  |  | Increased by 20-25% |
|  | Sunitinib | 10 μM |  |  | Increased by 55-65% |
| 18 | Sorafenib | 10 μM | Nitroglycerin | 100 μM | Increased by 30-40% |
|  | Regorafenib | 10 μM |  |  | Increased by 30-40% |
|  | Sunitinib | 10 μM |  |  | Increased by 50-60% |
| 19 | Sorafenib | 10 μM | Nicorandil | 100 μM | Increased by 15-20% |
|  | Regorafenib | 10 μM |  |  | Increased by 15-20% |
|  | Sunitinib | 10 μM |  |  | Increased by 50-60% |
| 20 | Regorafenib | 10 μM | Sildenafil | 100 μM | No significant change |
|  | Sunitinib | 10 μM |  |  |  |
|  | Sorafenib | 10 μM |  |  |  |

It can be seen from the results in Table 3 and FIG. 5 that the VEGF/VEGFR inhibitors have a proliferative toxicity on skin cells (HaCaT), while the nitric oxide releasing agents have a significantly ameliorating effect on the proliferative toxicity caused by the VEGF/VEGFR inhibitors, and the ameliorating effect is substantially better than Sildenafil.

TABLE 4

Experimental Conditions and Results of Examples 21-24

| Ex. No. | VEGFR inhibitor | Final Concentration | Nitric oxide releasing agent | Final Concentration | Cell Survival Rate |
|---|---|---|---|---|---|
| 21 | Sorafenib | 10 μM | Isoamyl Nitrite | 100 μM | Increased by 90-100% |
|  | Regorafenib | 10 μM |  |  | Increased by 65-75% |
|  | Sunitinib | 10 μM |  |  | Increased by 15-20% |
| 22 | Sorafenib | 10 μM | Molsidomine | 100 μM | Increased by 90-100% |
|  | Regorafenib | 10 μM |  |  | Increased by 60-70% |
|  | Sunitinib | 10 μM |  |  | Increased by 15-20% |
| 23 | Sorafenib | 10 μM | Nitroglycerin | 100 μM | Increased by 90-100% |

TABLE 4-continued

Experimental Conditions and Results of Examples 21-24

| Ex. No. | VEGFR inhibitor | Final Concentration | Nitric oxide releasing agent | Final Concentration | Cell Survival Rate |
|---|---|---|---|---|---|
| | Regorafenib | 10 μM | | | Increased by 80-90% |
| | Sunitinib | 10 μM | | | Increased by 20-30% |
| 24 | Sorafenib | 10 μM | Nicorandil | 100 μM | Increased by 90-100% |
| | Regorafenib | 10 μM | | | Increased by 60-70% |
| | Sunitinib | 10 μM | | | Increased by 15-20% |
| 20 | Regorafenib | 10 μM | | | No significant change |
| | Sunitinib | 10 μM | Sildenafil | 100 μM | |
| | Sorafenib | 10 μM | | | |

It can be seen from the results in Table 4 and FIG. 6 that the VEGF/VEGFR inhibitors have a proliferative toxicity on human oral mucosa epithelial keratinocytes (HOK), while the nitric oxide releasing agents have a significantly ameliorating effect on the proliferative toxicity caused by the VEGF/VEGFR inhibitors, and the ameliorating effect is substantially better than Sildenafil.

TABLE 5

Experimental Conditions and Results of Examples 25-28

| Ex. No. | VEGFR inhibitor | Final Concentration | the nitric oxide releasing agent | Final Concentration | Cell Survival Rate |
|---|---|---|---|---|---|
| 25 | Sorafenib | 10 μM | Isoamyl Nitrite | 100 μM | Increased by 15-20% |
| | Regorafenib | 10 μM | | | Increased by 20-30% |
| | Sunitinib | 10 μM | | | Increased by 40-50% |
| 26 | Sorafenib | 10 μM | Molsidomine | 100 μM | Increased by 20-30% |
| | Regorafenib | 10 μM | | | Increased by 20-30% |
| | Sunitinib | 10 μM | | | Increased by 15-20% |
| 27 | Sorafenib | 10 μM | Nitroglycerin | 100 μM | Increased by 30-40% |
| | Regorafenib | 10 μM | | | Increased by 40-50% |
| | Sunitinib | 10 μM | | | Increased by 70-80% |
| 28 | Sorafenib | 10 μM | Nicorandil | 100 μM | Increased by 20-30% |
| | Regorafenib | 10 μM | | | Increased by 20-30% |
| | Sunitinib | 10 μM | | | Increased by 30-40% |
| 20 | Regorafenib | 10 μM | | | No significant change |
| | Sunitinib | 10 μM | Sildenafil | 100 μM | |
| | Sorafenib | 10 μM | | | |

It can be seen from the results in Table 5 and FIG. 7 that the VEGF/VEGFR inhibitors have a proliferative toxicity on gastric epithelial cells (GES-1), while the nitric oxide releasing agents have a significantly ameliorating effect on the proliferative toxicity caused by the VEGF/VEGFR inhibitors, and the ameliorating effect is substantially better than Sildenafil.

TABLE 6

Experimental Conditions and Results of Examples 29-32

| Ex. No. | VEGFR inhibitor | Final Concentration | the nitric oxide releasing agent | Final Concentration | Cell Survival Rate |
|---|---|---|---|---|---|
| 29 | Sorafenib | 10 μM | Isoamyl Nitrite | 100 μM | Increased by 40-50% |
| | Regorafenib | 10 μM | | | Increased by 10-15% |
| | Sunitinib | 10 μM | | | Increased by 45-55% |
| 30 | Sorafenib | 10 μM | Molsidomine | 100 μM | Increased by 40-50% |
| | Regorafenib | 10 μM | | | Increased by 10-15% |
| | Sunitinib | 10 μM | | | Increased by 10-15% |
| 31 | Sorafenib | 10 μM | Nitroglycerin | 100 μM | Increased by 60-70% |
| | Regorafenib | 10 μM | | | Increased by 20-30% |
| | Sunitinib | 10 μM | | | Increased by 70-80% |
| 32 | Sorafenib | 10 μM | Nicorandil | 100 μM | Increased by 40-50% |
| | Regorafenib | 10 μM | | | Increased by 10-15% |
| | Sunitinib | 10 μM | | | Increased by 45-55% |
| 20 | Regorafenib | 10 μM | | | No significant change |
| | Sunitinib | 10 μM | Sildenafil | 100 μM | |
| | Sorafenib | 10 μM | | | |

It can be seen from the results in Table 6 and FIG. 8 that the VEGF/VEGFR inhibitors have a proliferative toxicity on human intestinal epithelial cells (FHs 74 Int), while the nitric oxide releasing agents have a significantly ameliorating effect on the proliferative toxicity caused by the VEGF/VEGFR inhibitors, and the ameliorating effect is substantially better than Sildenafil.

Examples 33-46: Determination of Effect of the Nitric Oxide Releasing Agent on Intra/Extra-Cellular NO Level The cultured HUVEC, HaCaT, HOK, FHs 74 Int or GES-1 cells were digested, suspended, counted, and seeded into a 24-well plate with 100,000-200,000 cells per well. After the cells were attached, a nitric oxide releasing agent solution was added to achieve a particular final concentration (e.g., as shown in Tables 7-8). A medium was added into the control group. At various time points after administration of the nitric oxide releasing agent (6 hours, 12 hours, 24 hours and 48 hours, e.g., as shown in Tables 7-8), 50 µL of supernatant of each group was collected for detecting the NO level in the extracellular supernatant. Meanwhile, the remainder supernatant was discarded, and a cell lysis solution was added. After sufficient lysis, 50 µL of lysate was taken for detecting the intracellular NO level. A NO Assay kit (S0021, Beyotime Inc.) was used for detecting the NO level.

Of those, FIGS. 9A-9D each represent the relative NO levels in HUVEC extracellular, HUVEC intracellular, GES-1 extracellular and GES-1 intracellular at 6 h, 12 h, 24 h, 48 h from administration of the nitric oxide releasing agent. NTG represents nitroglycerin. The control group was the basic medium, reflecting the biological level.

FIGS. 10A-10D each represent the relative extracellular NO levels in HUVEC cells, GES-1 cells, HaCaT cells, and HOK cells after 24 hours of treatment with the nitric oxide releasing agent (isosorbide dinitrate, nicorandil, molsidomine, and isoamyl nitrite). The control group was the basic medium, reflecting the biological level. Of those, ** represents P<0.01, indicating a significant difference as compared with the corresponding control group; * represents P<0.05, indicating a significant difference as compared with the corresponding control group; as statistically analyzed by using t-test.

FIGS. 11A-11D each represent the relative intracellular NO levels in HUVEC cells, GES-1 cells, HaCaT cells, and HOK cells after 24 hours of treatment with the nitric oxide releasing agent (isosorbide dinitrate, nicorandil, molsidomine, and isoamyl nitrite). The control group was the basic medium, reflecting the biological level. Of those, * represents P<0.001, indicating a significant difference as compared with the corresponding control group;  represents P<0.01, indicating a significant difference as compared with the corresponding control group; * represents P<0.05, indicating a significant difference as compared with the corresponding control group; as statistically analyzed by using t-test.

Figure 9:
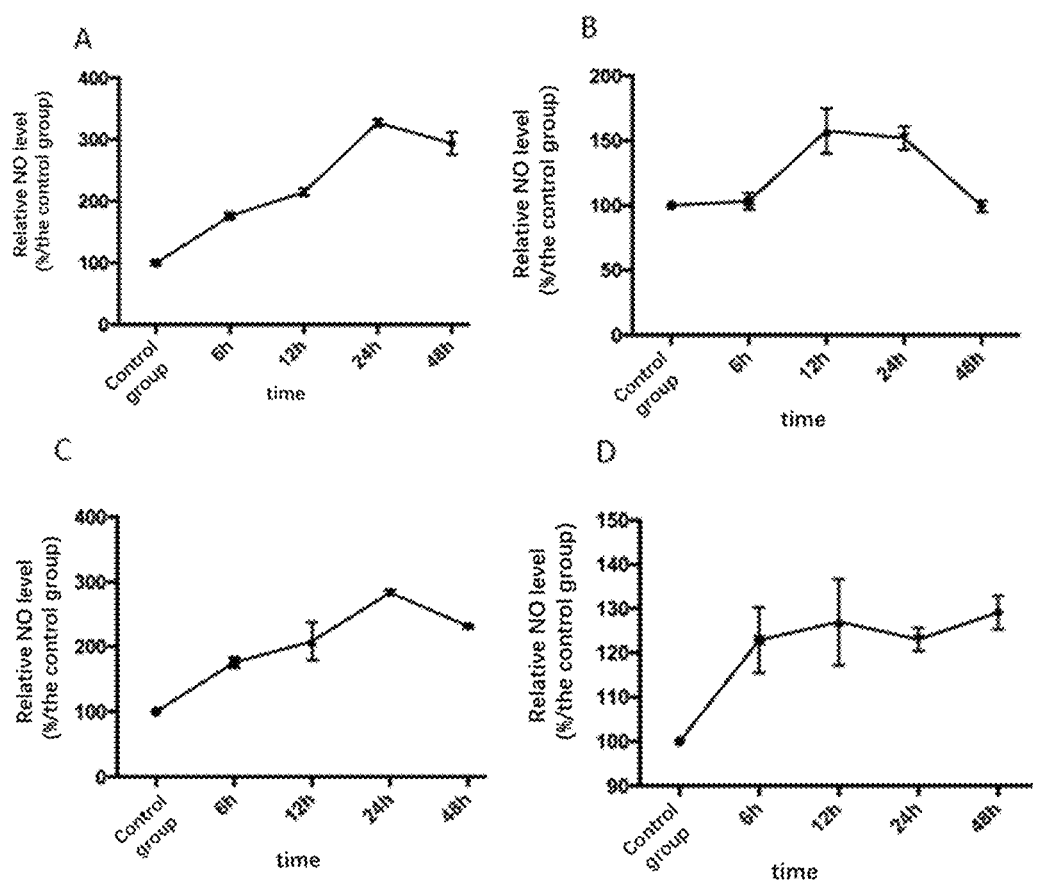
FIGS. 9A-9D depict the relative intracellular and extracellular NO levels of HUVEC and GES-1 cells.
Figure 10:
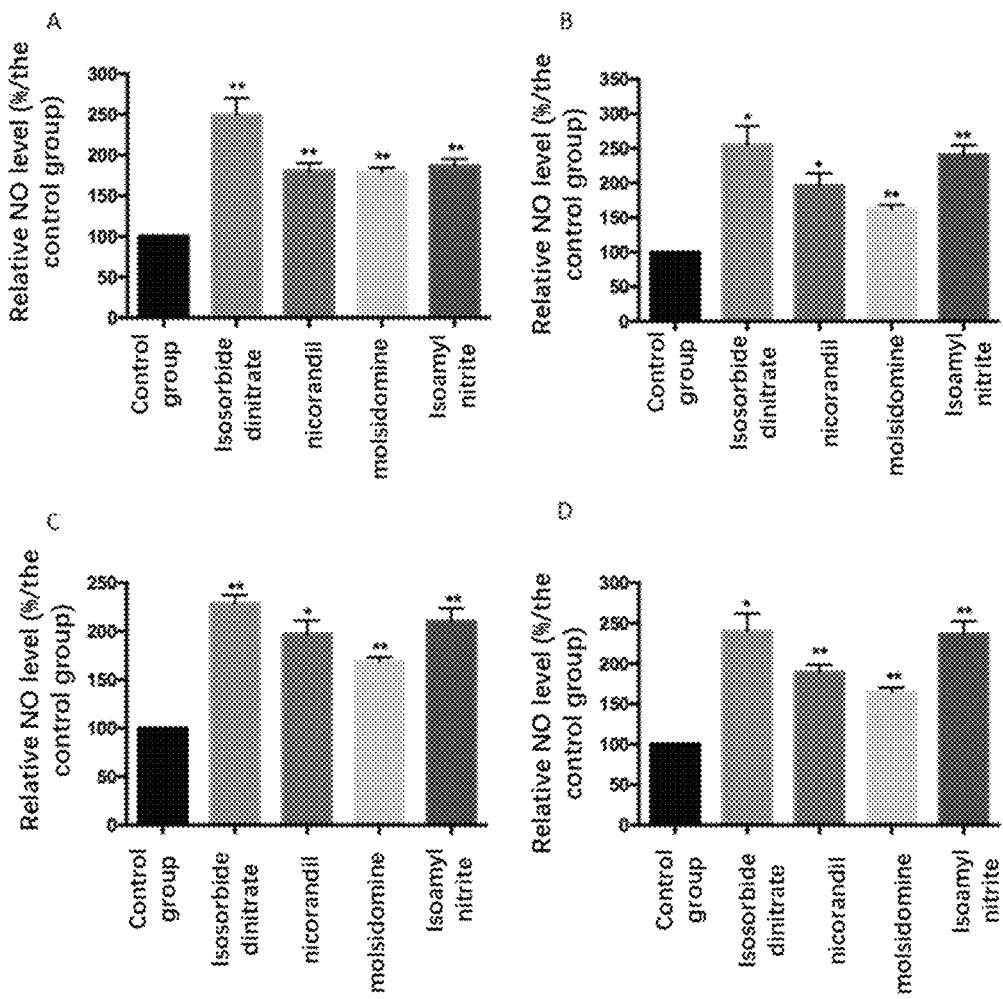
FIGS. 10A-10D depict the relative extracellular NO levels after 24 hours of treatment with a nitric oxide releasing agent.
Figure 11:
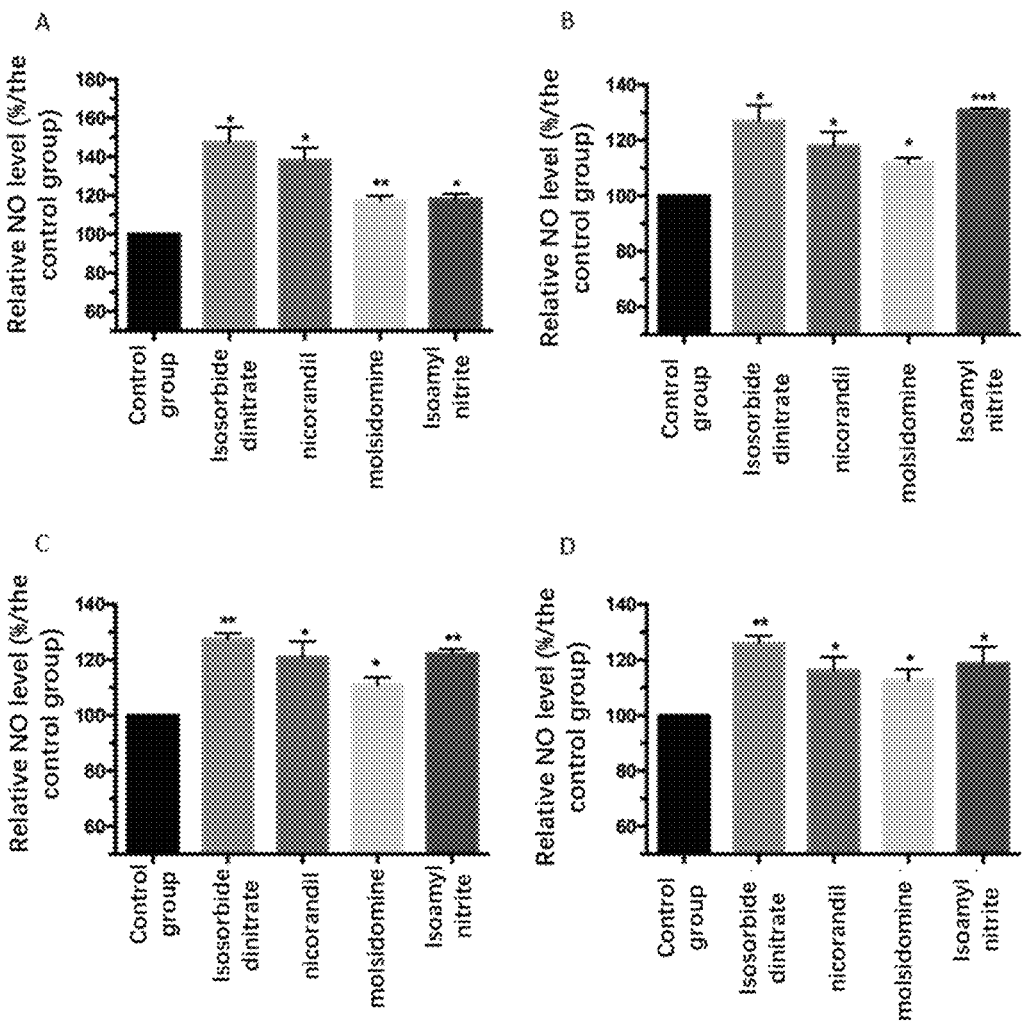
FIGS. 11A-11D depict the relative intracellular NO levels after 24 hours of treatment with a nitric oxide releasing agent.

It can be seen from the results in Tables 7-8 and FIGS. 9-11 that the nitric oxide releasing agent can release nitric oxide and increase the intracellular NO level.

TABLE 7

Experimental Conditions and Results of Examples 33-39

| Ex. No. | Medicament | Final Concentration | Cell Type (Extracellular) | Time Point | NO Level |
|---|---|---|---|---|---|
| 33 | Nitroglycerin (NTG) | 100 µM | HUVEC | 6 h | Increased by 70-80% |
| | | | | 12 h | Increased by 100-120% |
| | | | | 24 h | Increased by 200-235% |
| | | | | 48 h | Increased by 180-210% |
| 34 | Nitroglycerin (NTG) | 100 µM | GES-1 | 6 h | Increased by 70-85% |
| | | | | 12 h | Increased by 87-128% |
| | | | | 24 h | Increased by 170-185% |
| | | | | 48 h | Increased by 125-155% |
| 35 | Isosorbide Dinitrate | 100 µM | HUVEC | 24 h | Increased by 135-165% |
| | Nicorandil | 100 µM | | | Increased by 75-90% |
| | Molsidomine | 100 µM | | | Increased by 75-85% |
| | Isoamyl Nitrite | 100 µM | | | Increased by 80-95% |
| 36 | Isosorbide Dinitrate | 100 µM | HaCaT | 24 h | Increased by 120-150% |
| | Nicorandil | 100 µM | | | Increased by 85-110% |
| | Molsidomine | 100 µM | | | Increased by 66-85% |
| | Isoamyl Nitrite | 100 µM | | | Increased by 100-120% |
| 37 | Isosorbide Dinitrate | 100 µM | HOK | 24 h | Increased by 122-156% |
| | Nicorandil | 100 µM | | | Increased by 80-100% |
| | Molsidomine | 100 µM | | | Increased by 60-80% |
| | Isoamyl Nitrite | 100 µM | | | Increased by 125-147% |
| 38 | Isosorbide Dinitrate | 100 µM | FHs 74 Int | 24 h | Increased by 110-150% |
| | Nicorandil | 100 µM | | | Increased by 80-100% |
| | Molsidomine | 100 µM | | | Increased by 50-80% |
| | Isoamyl Nitrite | 100 µM | | | Increased by 110-125% |
| 39 | Isosorbide Dinitrate | 100 µM | GES-1 | 24 h | Increased by 135-174% |

TABLE 7-continued

Experimental Conditions and Results of Examples 33-39

| Ex. No. | Medicament | Final Concentration | Cell Type (Extracellular) | Time Point | NO Level |
|---|---|---|---|---|---|
| | Nicorandil | 100 μM | | | Increased by 80-110% |
| | Molsidomine | 100 μM | | | Increased by 55-80% |
| | Isoamyl Nitrite | 100 μM | | | Increased by 130-150% |

TABLE 8

Experimental Conditions and Results of Examples 40-46

| Ex. No. | Medicament | Final Concentration | Cell Type (Intracellular) | Time Point | NO Level |
|---|---|---|---|---|---|
| 40 | Nitroglycerin (NTG) | 100 μM | HUVEC | 6 h | Increased by 10-20% |
| | | | | 12 h | Increased by 45-70% |
| | | | | 24 h | Increased by 45-60% |
| | | | | 48 h | Increased by 1-20% |
| 41 | Nitroglycerin (NTG) | 100 μM | GES-1 | 6 h | Increased by 10-30% |
| | | | | 12 h | Increased by 20-35% |
| | | | | 24 h | Increased by 20-25% |
| | | | | 48 h | Increased by 20-30% |
| 42 | Isosorbide Dinitrate | 100 μM | HUVEC | 24 h | Increased by 40-55% |
| | Nicorandil | 100 μM | | | Increased by 30-45% |
| | Molsidomine | 100 μM | | | Increased by 15-25% |
| | Isoamyl Nitrite | 100 μM | | | Increased by 15-30% |
| 43 | Isosorbide Dinitrate | 100 μM | HaCaT | 24 h | Increased by 20-40% |
| | Nicorandil | 100 μM | | | Increased by 15-30% |
| | Molsidomine | 100 μM | | | Increased by 10-25% |
| | Isoamyl Nitrite | 100 μM | | | Increased by 20-40% |
| 44 | Isosorbide Dinitrate | 100 μM | HOK | 24 h | Increased by 20-40% |
| | Nicorandil | 100 μM | | | Increased by 10-30% |
| | Molsidomine | 100 μM | | | Increased by 9-30% |
| | Isoamyl Nitrite | 100 μM | | | Increased by 15-35% |
| 45 | Isosorbide Dinitrate | 100 μM | FHs 74 Int | 24 h | Increased by 15-35% |
| | Nicorandil | 100 μM | | | Increased by 10-30% |
| | Molsidomine | 100 μM | | | Increased by 10-25% |
| | Isoamyl Nitrite | 100 μM | | | Increased by 20-35% |
| 46 | Isosorbide Dinitrate | 100 μM | GES-1 | 24 h | Increased by 20-40% |
| | Nicorandil | 100 μM | | | Increased by 15-25% |
| | Molsidomine | 100 μM | | | Increased by 10-30% |
| | Isoamyl Nitrite | 100 μM | | | Increased by 25-35% |

Examples 47-54: Sildenafil Neither Release Nitric Oxide, Nor Increase the Intra- and Extracellular NO Levels of HUVEC, HaCaT or GES-1

Figure 12:
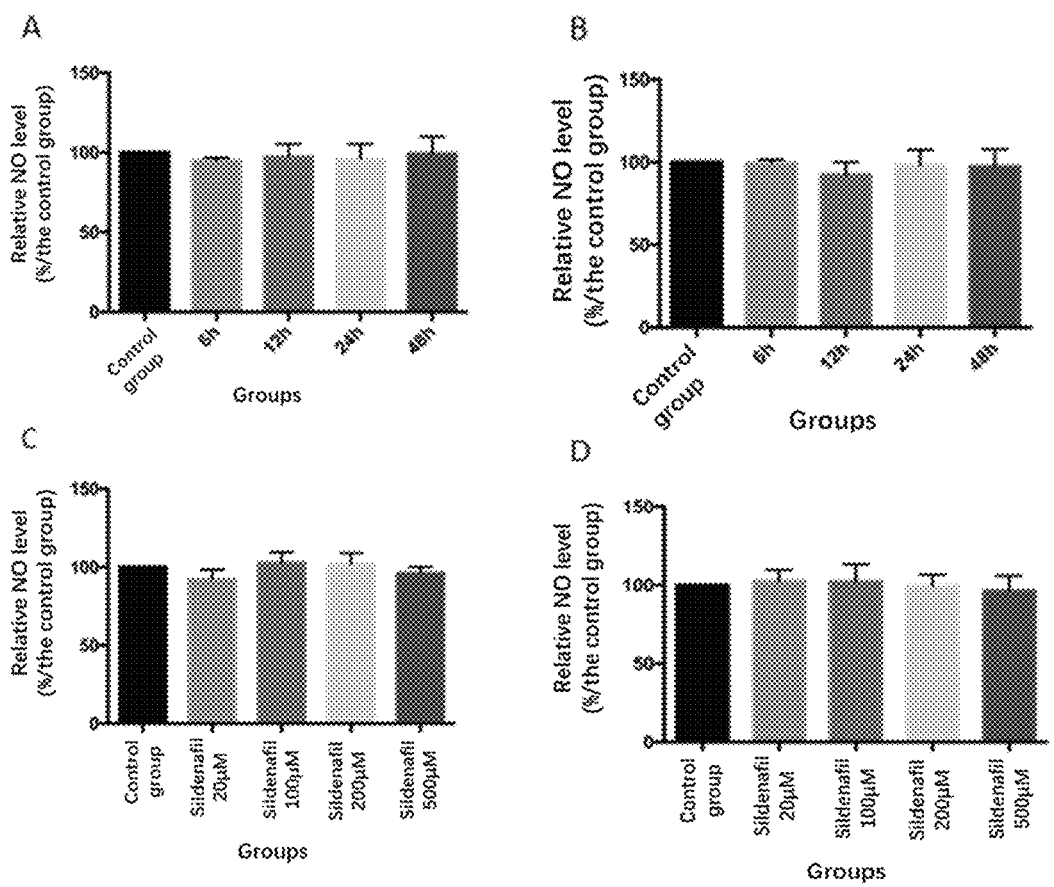
FIGS. 12A-12B depict the relative intracellular and extracellular NO levels at various time points after treatment of HUVEC cells with sildenafil.
FIGS. 12C-12D depict the relative intracellular and extracellular NO levels after 24 hours of treatment of HUVEC cells with sildenafil at various concentrations.
Figure 13:
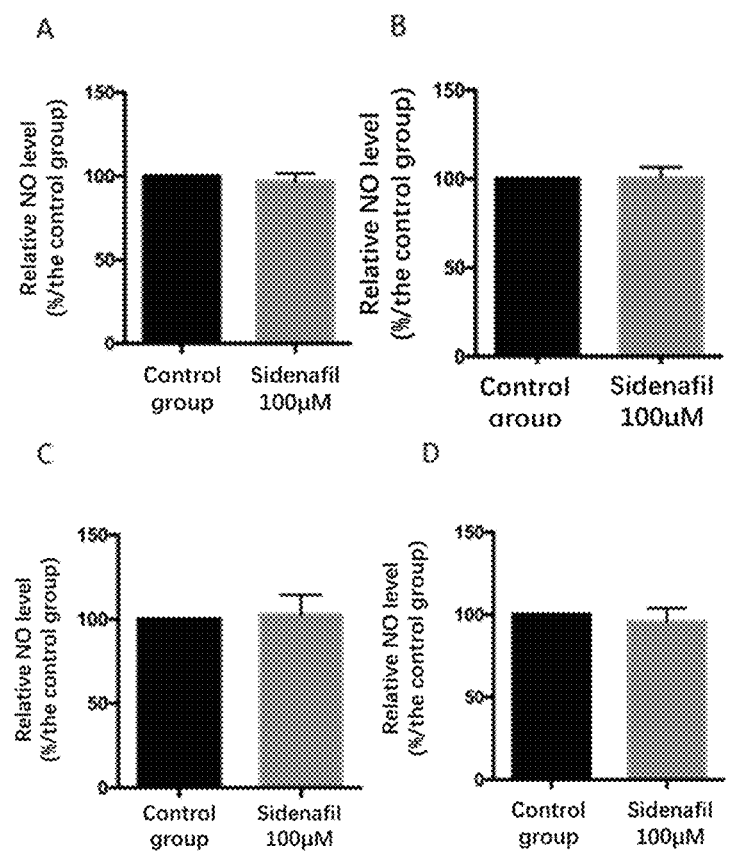
FIGS. 13A-13B depict the relative intracellular and extracellular NO levels after 24 hours of treatment GES-1 cells with 100 μM sildenafil.
FIG. 13C-13D depict the relative extracellular and intracellular NO levels after 24 hours of treatment of HaCaT cells with 100 μM sildenafil.

The cultured HUVEC, HaCaT or GES-1 cells were digested, suspended, counted, and seeded into 6-well plate with 500,000-1,000,000 cells per well. After the cells were attached, a Sildenafil solution was added to achieve a particular final concentration (e.g., as shown in Tables 9-10). A basic medium was added into the control group. At various time points after addition of Sildenafil (6 hours, 12 hours, 24 hours and 48 hours), 50 μL of supernatant of each group was collected for detecting the extracellular NO level. Meanwhile, the remainder supernatant was discarded, and a cell lysis solution was added. After sufficient lysis, 50 μL of lysate was taken for detecting the intracellular NO level. A NO Assay kit (S0021, Beyotime Inc.) was used for detecting the NO level. FIGS. 12-13 lists the experimental results.

Of those, FIGS. 12A-12B each represent the relative extra- and intra-cellular NO levels at various time points after treatment of HUVEC cells with 100 μM of Sildenafil (6 hours, 12 hours, 24 hours, 48 hours). FIGS. 12C-12D each represent the relative extra- and intra-cellular NO levels at 24 hours after treatment of HUVEC cells with different concentrations of Sildenafil. The control group was the basic medium, reflecting the biological level.

FIGS. 13A-13B each represent the relative extra- and intra-cellular NO levels at 24 hours from treatment of GES-1 cells with 100 μM of Sildenafil. FIGS. 13C-13D each represent the relative extra- and intra-cellular NO levels at 24 hours from treatment of HaCaT cells with 100 μM of Sildenafil. The control group was the basic medium, reflecting the biological level.

It can be seen from these results that Sildenafil neither release nitric oxide, nor increase the intra- and extracellular NO levels of HUVEC, HaCaT or GES-1 cells.

TABLE 9

Experimental Conditions and Results of Examples 47-50

| Ex. No. | Medicament | Final Concentration | Cell Type (Extracellular) | Time Point | NO Level |
|---|---|---|---|---|---|
| 47 | Sildenafil | 20 μM<br>100 μM<br>200 μM<br>500 μM | HUVEC | 24 h | No significant change |
| 48 | Sildenafil | 100 μM | HUVEC | 6 h<br>12 h<br>24 h<br>48 h | |
| 49 | Sildenafil | 100 μM | HaCaT | 24 h | |
| 50 | Sildenafil | 100 μM | GES-1 | 24 h | |

TABLE 10

Experimental Conditions and Results of Examples 51-54

| Ex. No. | Medicament | Final Concentration | Cell Type (Intracellular) | Time Point | NO Level |
|---|---|---|---|---|---|
| 51 | Sildenafil | 20 μM<br>100 μM<br>200 μM<br>500 μM | HUVEC | 24 h | No significant change |
| 52 | Sildenafil | 100 μM | HUVEC | 6 h<br>12 h<br>24 h<br>48 h | |
| 53 | Sildenafil | 100 μM | HaCaT | 24 h | |
| 54 | Sildenafil | 100 μM | GES-1 | 24 h | |

Figure 14:
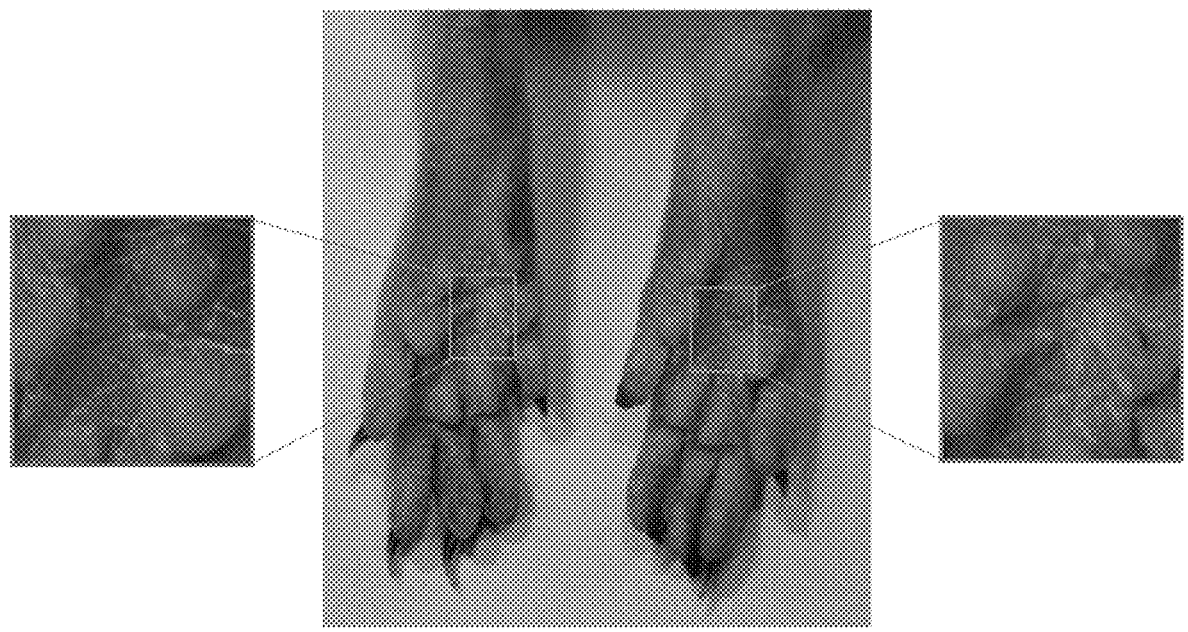
FIG. 14 depicts the photographs of left paw, front side, and right paw of rat model with hand-foot syndrome caused by VEGFR and/or VEGF inhibition.

Examples 55-108: The Nitric Oxide Releasing Agent is Capable of In Vivo Preventing/Treating Hand-Foot Syndrome Caused by Small Molecular VEGFR/VEGF Inhibitors Construction of rat animal model: A small molecular VEGFR/VEGF inhibitor as shown in Table 11 was administered to an 8-week SD female rat by daily gavage, and after several days the symptoms of hand-foot syndrome appeared on paws of the rat (e.g., as shown in FIG. 14) Similar to humans, the rat develops the symptoms of hand-foot syndrome after administration of the VEGFR/VEGF inhibitors, and the symptoms were highly similar in human and rat. Thus, rats are very good animal models for mimicking the side effects (e.g., hand-foot syndrome) caused by the VEGFR/VEGF inhibitors.

The rats (about 200 g) were fed for one week, and then divided to groups (each of which comprised 10 rats) for gavage administration experiments. A variety of small molecular VEGFR/VEGF inhibitors were dissolved in a mixed solution having a ratio of Cremophor EL:ethanol=1:1. Prior to gavage, the VEGFR/VEGF inhibitors medicament solution was diluted with PBS to the desired concentration (about 3 times diluted with a PBS solution). The gavage amount was not more than 2 mL, and the dosage was shown in Table 11. After gavage, the left paw of rat (palm and gaps of the paw) was topically administered with an ointment containing a nitric oxide releasing agent (about 0.05 g), while the right paw was not administered as the blank control. After administration, the rat was fixed in a fixed cylinder for 4 hours. After 4 hours, the rat was released, wiped with water to remove the residual medicament on the administered site, and returned to the cage. The gavage frequency of the VEGFR/VEGF inhibitor is shown in Table 11, but the nitric oxide releasing agent was administered only once per day. The gavage and administration were repeated every day, until the experiment ended. The number of rats on which the administered side kept normal or the symptoms of hand-foot-syndrome was substantially less serious than the side not administered after 15-18 days of administration was counted as the number of rats in which the hand-foot syndrome was effectively inhibited.

Table 11 lists various combinations of animal models of the VEGFR/VEGF inhibitors and the nitric oxide releasing agent ointments, and the corresponding experimental results (wherein, the value in the control rate column=the number of rats in which the hand-foot syndrome was effectively inhibited in each group/the number of the hand-foot syndrome models in each group×100%; the success rate of the hand-foot syndrome model in each group is 30% to 70%, that is, there are about 3-7 successful hand-foot syndrome models among 10 rats; during the modelling process, death of individual rat or unsuccessful modelling occur in different administration groups, death of individual rat or unsuccessful modelling in different drug groups).

TABLE 11

Experimental Conditions and Results of Examples 55-108

| Experiment No. | VEGFR/VEGF inhibitor | Dosage | Frequency | Administration | Concentration | Administered Paw | Days | Control Rate |
|---|---|---|---|---|---|---|---|---|
| 55 | Sorafenib | 80 mg/kg | once daily | Nitroglycerin ointment | 0.05% | Left | 15 | 66.67% |
| 56 | Sorafenib | 80 mg/kg | once daily | Nitroglycerin ointment | 0.15% | Left | 15 | 71.43% |
| 57 | Sorafenib | 80 mg/kg | once daily | Nitroglycerin ointment | 0.2% | Left | 15 | 60% |
| 58 | Apatinib | 105 mg/kg | once daily | Nitroglycerin ointment | 0.05% | Left | 15 | 60% |
| 59 | Apatinib | 105 mg/kg | once daily | Nitroglycerin ointment | 0.15% | Left | 15 | 60% |
| 60 | Apatinib | 105 mg/kg | once daily | Nitroglycerin ointment | 0.2% | Left | 15 | 75% |
| 61 | Lenvatinib | 65 mg/kg | twice daily | Nitroglycerin ointment | 0.05% | Left | 18 | 50% |

TABLE 11-continued

Experimental Conditions and Results of Examples 55-108

| Experiment No. | VEGFR/ VEGF inhibitor | Dosage | Frequency | Administration | Concentration | Administered Paw | Days | Control Rate |
|---|---|---|---|---|---|---|---|---|
| 62 | Lenvatinib | 65 mg/kg | twice daily | Nitroglycerin ointment | 0.15% | Left | 18 | 40% |
| 63 | Lenvatinib | 65 mg/kg | twice daily | Nitroglycerin ointment | 0.2% | Left | 18 | 60% |
| 64 | Regorafenib | 90 mg/kg | once daily | Nitroglycerin ointment | 0.05% | Left | 18 | 50% |
| 65 | Regorafenib | 90 mg/kg | once daily | Nitroglycerin ointment | 0.15% | Left | 18 | 60% |
| 66 | Regorafenib | 90 mg/kg | once daily | Nitroglycerin ointment | 0.2% | Left | 18 | 57.14% |
| 67 | Sunitinib | 120 mg/kg | once daily | Nitroglycerin ointment | 0.2% | Left | 15 | 50% |
| 68 | Cabozantinib | 50 mg/kg | once daily | Nitroglycerin ointment | 0.2% | Left | 18 | 66.67% |
| 69 | Axitinib | 50 mg/kg | once daily | Nitroglycerin ointment | 0.2% | Left | 18 | 50% |
| 70 | Ninteclanib | 110 mg/kg | once daily | Nitroglycerin ointment | 0.2% | Left | 18 | 75% |
| 71 | Brivanib | 80 mg/kg | once daily | Nitroglycerin ointment | 0.2% | Left | 18 | 33.33% |
| 72 | Vatalanib succinate | 150 mg/kg | once daily | Nitroglycerin ointment | 0.2% | Left | 15 | 50% |
| 73 | Fruquintinib | 40 mg/kg | once daily | Nitroglycerin ointment | 0.2% | Left | 16 | 66.67% |
| 74 | Sorafenib | 80 mg/kg | once daily | Isosorbide Mononitrate/Isosorbide Dinitrate (1:1) mixed ointment | 0.2% | Left | 15 | 42.86% |
| 75 | Apatinib | 105 mg/kg | once daily | Isosorbide Mononitrate/Isosorbide Dinitrate (1:1) mixed ointment | 0.2% | Left | 15 | 50% |
| 76 | Lenvatinib | 65 mg/kg | twice daily | Isosorbide Mononitrate/Isosorbide Dinitrate (1:1) mixed ointment | 0.2% | Left | 18 | 50% |
| 77 | Regorafenib | 90 mg/kg | once daily | Isosorbide Mononitrate/Isosorbide Dinitrate (1:1) mixed ointment | 0.2% | Left | 18 | 42.86% |
| 78 | Sunitinib | 120 mg/kg | once daily | Isosorbide Mononitrate/Isosorbide Dinitrate (1:1) mixed ointment | 0.2% | Left | 15 | 33.33% |
| 79 | Sorafenib | 80 mg/kg | once daily | Nicorandil ointment | 0.2% | Left | 15 | 33.33% |
| 80 | Lenvatinib | 65 mg/kg | twice daily | Nicorandil ointment | 0.2% | Left | 18 | 42.86% |
| 81 | Regorafenib | 90 mg/kg | once daily | Nicorandil ointment | 0.2% | Left | 18 | 40% |
| 82 | Apatinib | 105 mg/kg | once daily | Nicorandil ointment | 0.2% | Left | 15 | 25% |
| 83 | Sorafenib | 80 mg/kg | once daily | Sodium nitrate ointment | 0.2% | Left | 15 | 33.33% |
| 84 | Lenvatinib | 65 mg/kg | twice daily | Sodium nitrate ointment | 0.2% | Left | 18 | 42.86% |
| 85 | Regorafenib | 90 mg/kg | once daily | Sodium nitrate ointment | 0.2% | Left | 18 | 50% |
| 86 | Apatinib | 105 mg/kg | once daily | Sodium nitrate ointment | 0.2% | Left | 15 | 40% |
| 87 | Sorafenib | 80 mg/kg | once daily | Isoamyl Nitrite ointment | 0.2% | Left | 15 | 33.33% |
| 88 | Lenvatinib | 65 mg/kg | twice daily | Isoamyl Nitrite ointment | 0.2% | Left | 18 | 42.86% |

TABLE 11-continued

Experimental Conditions and Results of Examples 55-108

| Experiment No. | VEGFR/ VEGF inhibitor | Dosage | Frequency | Administration | Concentration | Administered Paw | Days | Control Rate |
|---|---|---|---|---|---|---|---|---|
| 89 | Regorafenib | 90 mg/kg | once daily | Isoamyl Nitrite ointment | 0.2% | Left | 18 | 40% |
| 90 | Apatinib | 105 mg/kg | once daily | Isoamyl Nitrite ointment | 0.2% | Left | 15 | 20% |
| 91 | Sorafenib | 80 mg/kg | once daily | Sodium nitrite ointment | 0.2% | Left | 15 | 42.86% |
| 92 | Lenvatinib | 65 mg/kg | twice daily | Sodium nitrite ointment | 0.2% | Left | 18 | 33.33% |
| 93 | Sorafenib | 80 mg/kg | once daily | Molsidomine ointment | 0.2% | Left | 15 | 33.33% |
| 94 | Lenvatinib | 65 mg/kg | twice daily | Molsidomine ointment | 0.2% | Left | 18 | 40% |
| 95 | Sorafenib | 80 mg/kg | once daily | sodium nitroprusside ointment | 0.2% | Left | 15 | 42.86% |
| 96 | Lenvatinib | 65 mg/kg | twice daily | sodium nitroprusside ointment | 0.2% | Left | 18 | 28.57% |
| 97 | Sorafenib | 80 mg/kg | once daily | S-nitrosothiol silica nanospheres ointment | 0.2% | Left | 15 | 40% |
| 98 | Lenvatinib | 65 mg/kg | twice daily | S-nitrosothiol silica nanospheres ointment | 0.2% | Left | 18 | 33.33% |
| 99 | Sorafenib | 80 mg/kg | once daily | S-nitrosoethanedithiol chitin ointment | 0.2% | Left | 15 | 28.57% |
| 100 | Lenvatinib | 65 mg/kg | twice daily | S-nitrosoethanedithiol chitin ointment | 0.2% | Left | 18 | 16.67% |
| 101 | Sorafenib | 80 mg/kg | once daily | oligopropylenediamine-grafted chitosan NONOate ointment | 0.2% | Right | 15 | 20% |
| 102 | Lenvatinib | 65 mg/kg | twice daily | oligopropylenediamine-grafted chitosan NONOate ointment | 0.2% | Right | 18 | 14.29% |
| 103 | Sorafenib | 80 mg/kg | once daily | N-nitrosoclibutylamine ointment | 0.2% | Right | 15 | 33.33% |
| 104 | Lenvatinib | 65 mg/kg | twice daily | N-nitrosoclibutylamine ointment | 0.2% | Right | 18 | 25% |
| 105 | Sorafenib | 80 mg/kg | once daily | hydroxyldiazene sulfonic acid-1-oxide disodium salt ointment | 0.2% | Right | 15 | 20% |
| 106 | Lenvatinib | 65 mg/kg | twice daily | hydroxyldiazene sulfonic acid-1-oxide disodium salt ointment | 0.2% | Right | 18 | 33.33% |
| 107 | Sorafenib | 80 mg/kg | once daily | streptozocin ointment | 0.2% | Right | 15 | 20% |
| 108 | Lenvatinib | 65 mg/kg | twice daily | streptozocin ointment | 0.2% | Right | 18 | 16.67% |

NOTE:

The modelling success rate of anti-cancer medicaments are not constant: the success rate of the hand-foot syndrome model in each group is 30% to 70%, that is, there are about 3-7 successful hand-foot syndrome models among 10 rats, during the modelling process, death of individual rat or unsuccessful modelling occur in different administration groups. The control rate refers to the ratio of the number of rats in which the symptoms on the administered paw are less serious than the paw not administrated to the total number of the hand-foot syndrome model rats in the experimental groups.

Figure 15:
FIG. 15 depicts the photographs of left paw, front side, and right paw of a typical rat (administered to the left paw) in the administration groups of examples 55-100 and 111-112 of the present application.
Figure 16:
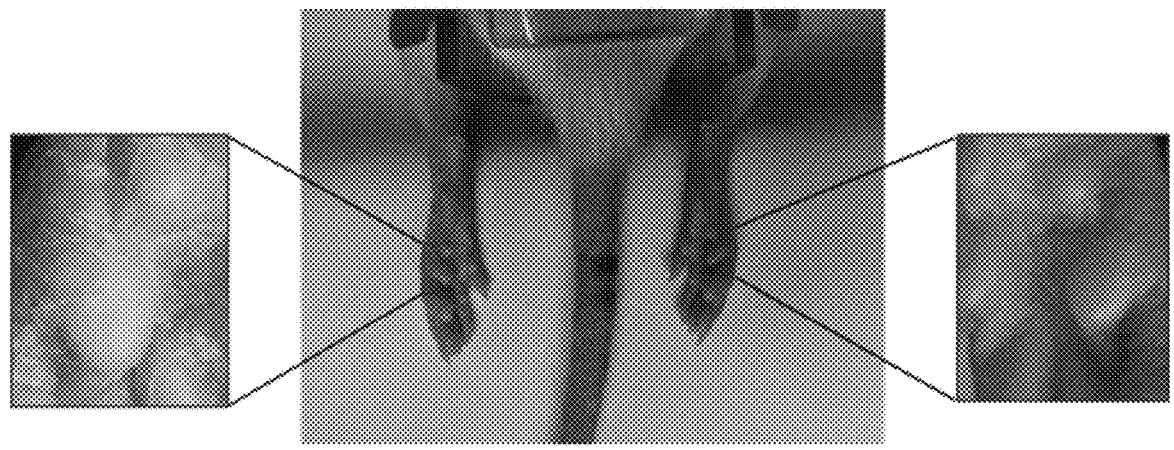
FIG. 16 depicts the photographs of left paw, front side, and right paw of a typical rat (administrated to the right paw) in the administration groups of examples 101-108 of the present application.

It can be seen from the results in Table 11 that the nitric oxide releasing agent is capable of effectively preventing and treating the hand-foot syndrome caused by the VEGFR/VEGF inhibitors. Meanwhile, the results of FIGS. 15-16 also show that the nitric oxide releasing agent is capable of effectively preventing and treating the hand-foot syndrome caused by the VEGFR/VEGF inhibitors. FIG. 15 shows that in the administration groups of Examples 55-100, a typical rat was administered on its left paw (with a nitric oxide releasing agent ointment), and the hand-foot syndrome on its left paw were significantly ameliorated; FIG. 16 shows that in the administration groups of Examples 101-108, a typical rat was administered on its right paw (with a nitric oxide releasing agent ointment), and the hand-foot syndrome on its right paw are also significantly ameliorated.

Examples 109-110: The Nitric Oxide Releasing Agent is Capable of In Vivo Preventing/Treating the Hand-Foot Syndrome Caused by a Small Molecular VEGFR/VEGF Inhibitor Preparation of *Nitrosomonas europaea* lotion: Inoculated *Nitrosomonas europaea* (ATCC 19718) into inorganic medium (ATCC 2265), cultured at about 200 rpm, 26° C., dark condition for 3-5 days until the medium turned turbid to obtain bacterial stock liquid. Diluted the stock liquid to different concentration of solution with the inorganic medium (such as $10^7$, $10^8$, $10^9$, $10^{10}$ cell/ml). The concentration of bacterial was determined with a cytometer, and then, obtain the *Nitrosomonas europaea* lotion.

Construction of rat animal model: A small molecular VEGFR/VEGF inhibitor as shown in Table 12 was administered to an 8-week SD female rat by daily gavage, and after several days the symptoms of hand-foot syndrome appeared on paws of the rat Similar to humans, the rat develops the symptoms of hand-foot syndrome after administration of the VEGFR/VEGF inhibitors, and the symptoms were highly similar in human and rat. Thus, rats are very good animal models for mimicking the side effects (e.g., hand-foot syndrome) caused by the VEGFR/VEGF inhibitors.

The rats (about 200 g) were fed for one week, and then divided to groups (each of which comprised 10 rats) for gavage administration experiments. A variety of small molecular VEGFR/VEGF inhibitors were dissolved in a mixed solution having a ratio of Cremophor EL:ethanol=1:1. Prior to gavage, the VEGFR/VEGF inhibitors medicament solution was diluted with PBS to the desired concentration (about 3 times diluted with a PBS solution). The gavage amount was not more than 2 mL, and the dosage was shown in Table 12. After gavage, the rat was fixed in a fixed cylinder. The left paw of rat was soaked with bacterial lotion. After 10 min, the rat was released, once a day, while the right paw was not soaked as the blank control. The gavage frequency of the VEGFR/VEGF inhibitor is shown in Table 12, but the nitric oxide releasing agent was administered only once per day. The gavage and soaking experiment were repeated every day, until the rat died. The number of rats on which the soaking side kept normal or the symptoms of hand-foot-syndrome was substantially less serious than the unadministered side after 15-18 days of administration was counted as the number of rats in which the hand-foot syndrome was effectively inhibited.

Table 12 lists various combinations of animal models of the VEGFR/VEGF inhibitors and the nitric oxide releasing agent ointments, and the corresponding experimental results (wherein, the value in the control rate column=the number of rats in which the hand-foot syndrome was effectively inhibited in each group/the number of the hand-foot syndrome models in each group×100%; the success rate of the hand-foot syndrome model in each group is 30% to 70%, that is, there are about 3-7 successful hand-foot syndrome models among 10 rats; during the modelling process, death of individual rat or unsuccessful modelling occur in different administration groups, death of individual rats occurs in each administration group).

TABLE 2

Experimental Conditions and Results of Examples 109-110

| Experiment No. | VEGFR inhibitor | Dosage | Frequency | Administration | Concentration wt % | Administered Paw | Days | Control Rate |
|---|---|---|---|---|---|---|---|---|
| 109 | Sorafenib | 80 mg/kg | once daily | Bacterial lotion | $10^9$bacteria/mL | 左 | 15 | 33.33% |
| 110 | Lenvatinib | 65 mg/kg | twice daily | Bacterial lotion | $10^9$bacteria/mL | 左 | 15 | 25% |

It can be seen from Table 12 that the nitric oxide releasing agent is capable of effectively preventing and treating the hand-foot syndrome caused by the VEGFR/VEGF inhibitors.

Examples 111-112: The Nitric Oxide Releasing Agent is Capable of In Vivo Preventing/Treating the Hand-Foot Syndrome Caused by a Protein Macromolecular VEGFR/VEGF Inhibitor Ramucirumab or Bevacizumab was diluted with normal saline to the desired concentration. Rats (about 200 g) were fed for one week, and then divided to groups (each of which comprised 10 rats) for injection administration experiments. The diluted Ramucirumab was administered by intravenous infusion for 60 mins with a dosage of 40 mg/kg. It was administered once per week, together with administration of paclitaxel (10 mg/kg). The left paw (the palm and gaps of paw) of the rat was topically administered with an ointment containing a nitric oxide releasing agent (about 0.05 g), while the right paw was not administered as the blank control. After administration, the rat was fixed in a fixed cylinder for 4 h. After 4 h, the rat was released, wiped with water to remove the residual medicament on the administered site, and returned to the cage. The experiments lasted for 2-4 weeks. The experimental phenomena were observed, until the experimental rat died and the experiment was over.

Table 13 lists various combinations of animal models of the VEGFR/VEGF inhibitors and the nitric oxide releasing agent ointments, and the corresponding experimental results (wherein, the value in the control rate column=the number of rats in which the hand-foot syndrome was effectively inhibited in each group/the number of the hand-foot syndrome models in each group×100%; the success rate of hand-foot syndrome modelling in each group is 10% to 30%, that is, there are about 1-3 hand-foot syndrome models in 10 rats)

effectively preventing the hand-foot syndrome caused by the monoclonal antibody-based VEGFR/VEGF inhibitors.

Examples 113-124: Experiments for Demonstrating the Ability of Treating the Hand-Foot Syndrome Caused by the Small Molecular VEGFR/VEGF Inhibitors in Rat Models Rats (about 200 g) were fed for one week, and then divided to groups (each of which comprised 10 rats) for gavage administration experiments. A VEGFR/VEGF inhibitor was dissolved in a mixed solution having a ratio of Cremophor EL:ethanol=1:1, and diluted with PBS to the desired concentration (about 3 times diluted with a PBS solution) prior to gavage. The gavage amount was not more than 2 mL, and the dosage was shown in Table 14. The gavage was repeated every day for VEGFR/VEGF inhibitor, until the rat developed the symptoms of hand-foot syndrome. At this time, the therapeutic experiment was initiated. During the process of therapeutic experiments, the rat was continuously subject to gavage with the VEGFR/VEGF inhibitor at a low frequency (the frequency of gavage was described as Table 14). After gavage, the rat was topically administered on its left paw (palm and gaps of paw) with a nitric oxide releasing agent ointment (about 0.05 g), while the right paw was not administered as the blank control. After administration, the rat was fixed in a fixed cylinder for 4 hours. After 4 hours, the rat was released, wiped with water to remove the residual medicament on the administered site, and returned to the cage. The gavage frequency of the VEGFR/VEGF inhibitor is shown in Table 14, but the nitric oxide releasing agent was administered only once per day. After 6-10 days of administration, the number of rats in which the administered side returned to normal or exhibited significantly less serious than the side not administrated was counted as the number of rats in which the hand-foot syndrome was effectively inhibited.

TABLE 13

Experimental Conditions and Results of Examples 111-112

| Experiment No. | VEGFR inhibitor/ VEGF inhibitor | Classification of Inhibitor | Dosage | Frequency | Administration | Concentration | Administered Paw | Days | Control Rate |
|---|---|---|---|---|---|---|---|---|---|
| 111 | Ramucimmab | Monoclonal antibody | Administered in combination with paclitaxel, injected over 60 min | Intraperitoneally injected once per week | Nitroglycerin ointment | 0.2% | Left | 23 | 50% |
| 112 | Bevacizumab | Monoclonal antibody | Administered in combination with 5-FU, injected over 60-90 mins | Injected through caudal vein once per week | Nitroglycerin ointment | 0.2% | Left | 18 | 50% |

NOTE:
The modelling success rate of anti-cancer medicaments are not constant:The success rate of hand-foot syndrome in each group is 10%-30%, that is, there are about 1-3 hand-foot syndrome models in 10 rats, during the modelling process, death of individual rat or unsuccessful modelling in different administration groups. The control rate refers to the ratio of the number of rats in which the symptoms on the administered paw are less serious than the unadministered paw to the total number of the hand-foot syndrome model rats in the experimental groups.

FIG. 15 shows the conditions of the left paw, front side, and right paw of a typical rat in the administration groups of examples 111-112, after it was topically administered on its left paw (with a nitric oxide releasing agent ointment).

It can be seen from the results in Table 13 and FIG. 15 that the nitric oxide releasing agent ointment is capable of Table 14 summarizes animal studies of administration of various small molecular VEGFR/VEGF inhibitors and the nitric oxide releasing agent ointments, and the corresponding experimental results (wherein, the value in the ameliorated ratio=the number of rats in which the hand-foot syndrome was effectively treated in each group/the number of the hand-foot syndrome models in each group×100%).

TABLE 14

Experimental Conditions and Results of Examples 113-124

| Experiment No. | VEGFR inhibitor | Dosage | Frequency | Days of Administration Modelling | Administration | Days of Adminitrations | Concentration | administration Paw | Ameliorated Rate |
|---|---|---|---|---|---|---|---|---|---|
| 113 | Sorafenib | 80 mg/kg | Once per day during modelling, and once per two days after the treatment was initiated | 8 | Nitroglycerin ointment | 5 | 0.2% | Left | 50% |
| 114 | Apatinib | 105 mg/kg | Once per day during modelling, and once per two days after the treatment was initiated | 10 | Nitroglycerin ointment | 5 | 0.2% | Left | 40% |
| 115 | Lenvatimb | 65 mg/kg | Twice per day during modelling, and once per day after the treatment was initiated | 13 | Nitroglycerin ointment | 6 | 0.2% | Left | 42.86% |
| 116 | Regorafenib | 90 mg/kg | Once per day during modelling, and once per two days after the treatment was initiated | 12 | Nitroglycerin ointment | 5 | 0.2% | Left | 33.33% |
| 117 | Sunitinib | 120 mg/kg | Once per day during modelling, and once per two days after the treatment was initiated | 10 | Nitroglycerin ointment | 6 | 0.2% | Left | 40% |
| 118 | Sorafenib | 80 mg/kg | Once per day during modelling, and once per two days after the treatment was initiated | 8 | Isosorbide Dinitrate and Isosorbide Mononitrate mixed ointment | 8 | 0.2% | Left | 50% |
| 119 | Apatinib | 105 mg/kg | Once per day during modelling, and once per two days after the treatment was initiated | 10 | Isosorbide Dinitrate and Isosorbide Mononitrate mixed ointment | 7 | 0.2% | Left | 50% |
| 120 | Sorafenib | 80 mg/kg | Once per day during modelling, and once per two | 8 | Nicorandil ointment | 9 | 0.2% | Left | 40% |

TABLE 14-continued

Experimental Conditions and Results of Examples 113-124

| Experiment No. | VEGFR inhibitor | Dosage | Frequency | Days of Administration Modelling | Administration | Days of Adminitrations | Concentration | administration Paw | Ameliorated Rate |
|---|---|---|---|---|---|---|---|---|---|
| 121 | Apatinib | 105 mg/kg | Once per day during modelling, and once per two days after the treatment was initiated | 10 | Nicorandil ointment | 9 | 0.2% | Left | 40% |
| 122 | Sorafenib | 80 mg/kg | Once per day during modelling, and once per two days after the treatment was initiated | 8 | sodium nitroprusside ointment | 8 | 0.2% | Left | 20% |
| 123 | Sorafenib | 80 mg/kg | Once per day during modelling, and once per two days after the treatment was initiated | 8 | a polymer ointment | 10 | 0.2% | Left | 33.33% |
| 124 | Sorafenib | 80 mg/kg | Once per day during modelling, and once per two days after the treat ment was initiated | 8 | Molsidomine ointment | 8 | 0.2% | Right | 16.67% |

NOTE:
The modelling success rate of anti-cancer medicaments are not constant: The success rate of hand-foot syndrome in each group is 40%-70%, that is, there are about 1-3 hand-foot syndrome models in 10 rats, during the modelling process, death of individual rat or unsuccessful occur in different administration groups. The control rate refers to the ratio of the number of rats in which the symptoms on the administered paw are less serious than the unadministered paw to the total number of the hand-foot syndrome model rats in the experimental groups.

Figure 17:
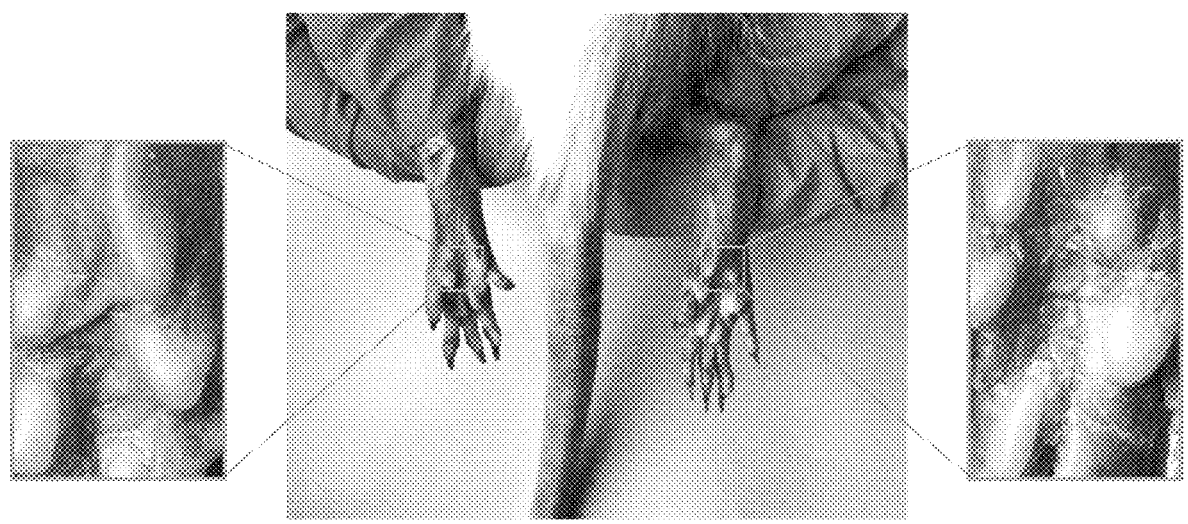
FIG. 17 depicts the photographs of left paw, front side, and right paw of a typical rat (administered to the left paw) in the administration groups of examples 113-123 of the present application.
Figure 18:
FIG. 18 depicts the photographs of left paw, front side, and right paw of a typical rat (administrated to the right paw) in the administration group of example 124 of the present application.

FIG. 17 shows the conditions of the left paw, front side, and right paw of a typical rat in the administration groups of examples 113-124 after it was topically administered on its left paw (with a nitric oxide releasing agent ointment). FIG. 18 shows the conditions of the left and right paws of a typical rat in the administration group of examples 124 after it was administered on its right paw (with a nitric oxide releasing agent ointment).

It can be seen from the results in Table 14 and FIG. 17-18 that the nitric oxide releasing agent ointment is capable of effectively treating the hand-foot syndrome caused by the small molecular VEGFR inhibitors.

Examples 125-142: Comparison of 0.2% Nitroglycerin Ointment with Other Currently Clinically Available Investigational Medicaments and Other Nitric Oxide Releasing Agents in the Experiments of Preventing the Hand-Foot Syndrome Caused by the Small Molecular VEGFR/VEGF Inhibitors Rats (about 200 g) were fed for one week, divided to groups (each of which comprised 10 rats), and then subjected to gavage administration experiments. A VEGFR inhibitor was dissolved in a mixed solution having a ratio of Cremophor EL:ethanol=1:1, and diluted with PBS to the desired concentration (about 3 times diluted with a PBS solution) prior to gavage. The gavage amount was not more than 2 mL, and the dosage was shown in Table 15. After gavage, the left paw (palm and gaps of paw) of the rat was topically administered with nitroglycerin ointment (about 0.05 g), and the right paw was topically administered with the currently clinically available investigational medicaments or the other nitric oxide releasing agent ointment in the same manner. After administration, the rat was fixed by a fixed cylinder for about 4 hours. After 4 hours, the rat was released, wiped with water to remove the residual medicament on the administered site, and returned to the cage. The gavage frequency of the VEGFR/VEGF inhibitors is shown in Table 15, but the clinically available other skin medicaments and the nitric oxide releasing agents were administered only once. The rat was subject to gavage with the VEGFR/VEGF inhibitors, until the paw administered with the clinically available investigational medicament (or the other nitric oxide releasing agent) developed the symptoms of hand-foot syndrome or the rat died. After 15-18 days of administration, the number of rats in which the paw administered with nitroglycerin ointment exhibited normal or significantly less serious than the paw administered with the clinically investigational medicament (or the other nitric oxide releasing agent) was counted as the number of rats in which the hand-foot syndrome was effectively prevented.

Table 15 lists the combination of experiments of 0.2% nitroglycerin ointments and clinically investigational medicaments (or the other nitric oxide releasing agent), and the corresponding experimental results (wherein, the value in the relative ameliorated rate column=the number of rats in which the hand-foot syndrome on the left paw was significantly less serious than the hand-foot syndrome on the right paw in each group/the hand-foot syndrome model in each group×100%).

TABLE 15

Experimental Conditions and Results of Examples 125-142

| Experiment No. | VEGFR inhibitor | Dosage | Frequency | Administration Left | Administration Right | Administration Days | Relative Ameliorated Rate |
|---|---|---|---|---|---|---|---|
| 125 | Sorafenib | 80 mg/kg | once per day | 0.2% Nitroglycerin ointment | 1% Sildenafil | 15 | 66.67% |
| 126 | Apatinib | 105 mg/kg | once per day | 0.2% Nitroglycerin ointment | 1% Sildenafil | 15 | 75% |
| 127 | Lenvatinib | 100 mg/kg | twice per day | 0.2% Nitroglycerin ointment | 1% Sildenafil | 18 | 60% |
| 128 | Regorafenib | 90 mg/kg | once per day | 0.2% Nitroglycerin ointment | 1% Sildenafil | 18 | 75% |
| 129 | Sunitinib | 120 mg/kg | once per day | 0.2% Nitroglycerin ointment | 1% Sildenafil | 15 | 66.67% |
| 130 | Sorafenib | 80 mg/kg | once per day | 0.2% Nitroglycerin ointment | urea frost | 15 | 60% |
| 131 | Sorafenib | 80 mg/kg | once per day | 0.2% Nitroglycerin ointment | Vaseline ointment | 15 | 66.67% |
| 132 | Sorafenib | 80 mg/kg | once per day | 0.2% Nitroglycerin ointment | Urea ointment | 15 | 57.14% |
| 133 | Sorafenib | 80 mg/kg | once per day | 0.2% Nitroglycerin ointment | brimonidine ointment | 15 | 60% |
| 134 | Sorafenib | 80 mg/kg | once per day | 0.2% Nitroglycerin ointment | vitamin B6 ointment | 15 | 57.14% |
| 135 | Sorafenib | 80 mg/kg | once per day | 0.2% Nitroglycerin ointment | Nicotine ointment | 15 | 66.67% |
| 136 | Sorafenib | 80 mg/kg | once per day | 0.2% Nitroglycerin ointment | Dexamethasone ointment | 15 | 75% |
| 137 | Sorafenib | 80 mg/kg | once per day | 0.2% Nitroglycerin ointment | hydrocortisone ointment | 15 | 60% |
| 138 | Sorafenib | 80 mg/kg | once per day | 0.2% Nitroglycerin ointment | Vk1 ointment (0.1%) | 15 | 66.67% |
| 139 | Sorafenib | 80 mg/kg | once per day | 0.2% Nitroglycerin ointment | elythrocin ointment | 15 | 66.67% |
| 140 | Sorafenib | 80 mg/kg | once per day | 0.2% Nitroglycerin ointment | triamcinolone ointment | 15 | 60% |
| 141 | Sorafenib | 80 mg/kg | once per day | 0.2% Nitroglycerin ointment | 0.2% Isoamyl Nitrite ointment | 15 | 50% |

TABLE 15-continued

Experimental Conditions and Results of Examples 125-142

| Experiment No. | VEGFR inhibitor | Dosage | Frequency | Administration Left | Administration Right | Administration Days | Relative Ameliorated Rate |
|---|---|---|---|---|---|---|---|
| 142 | Sorafenib | 80 mg/kg | once per day | 0.2% Nitroglycerin ointment | 0.2% streptozocin ointment | 15 | 60% |

It can be seen from the results in Table 15 that as compared with 1% Sildenafil, 0.2% nitroglycerin ointments are capable of effectively controlling the hand-foot syndrome caused by the VEGFR inhibitor and/or the VEGF inhibitor; as compared with the currently clinically available other investigational medicaments (which produce almost no therapeutically effect on the hand-foot syndrome caused by the VEGFR inhibitor and/or the VEGF inhibitor), 0.2% nitroglycerin ointments are capable of effectively inhibiting the hand-foot syndrome caused by the VEGFR inhibitor and/or the VEGF inhibitor; as compared with other the nitric oxide releasing agent ointments, 0.2% nitroglycerin ointments are capable of more effectively controlling the hand-foot syndrome caused by the VEGFR inhibitor and/or the VEGF inhibitor. The concentration of 0.2% nitroglycerin ointments is significantly lower than the concentrations of the currently clinically available other investigational medicaments, which can be seen 0.2% nitroglycerin ointments has an unexpected technological effect.

Examples 143: Effect of the Nitric Oxide Releasing Agent on the Therapeutic Effect of the VEGFR/VEGF Inhibitor BALB/C nude mouse (liver cancer cell HepG2 transplanted tumor) model was constructed. After the models were stable, the model mice were divided to three groups (in which the average of the rat tumor size kept uniform as possible), each of which comprised 10 mice, which were subject to gavage and topical administration experiments.

A VEGFR inhibitor was dissolved in a mixed solution having a ratio of Cremophor EL:ethanol=1:1 (volumetric ratio), and diluted with PBS to the desired concentration (about 3 times diluted with a PBS solution) prior to gavage. The gavage amount was not more than 0.2 mL, and the dosage was 30 mg/kg per day. The tumor-bearing mouse was orally administered Sorafenib every day for the purpose of controlling or reducing the tumor. Meanwhile, a medicament for treating the side effect was externally administered on the back of the mouse in a manner of external administration (the particular grouping was as follows: Group A: gavage+administration with excipient; Group B: gavage+administration with 0.15% nitroglycerin ointment; Group C: gavage+administration with 0.2% nitroglycerin ointment; about 5.8 $cm^2$ of administered area were labelled with a marking pen, and the administered area cannot be an area which the mouth of mouse can touch or an area closely near the tumor). After completion of gavage every day, a blank ointment was topically administered to uniform to the labelled area of the back of the model mouse to keep the skin moist. After administration, each mouse was held in a relatively independent space for 4 hours. After 4 hours, the residual ointment on the back of mouse was wiped off with a paper towel or a wetter paper towel. Then, the mouse was returned to the former cage for normal activity. The tumor size was measured and recorded every two days. After 20 days of experiments, the mouse was dissected. The tumor was removed, weighed and recorded. The change of tumor volume of different experimental groups was observed.

Figure 19:
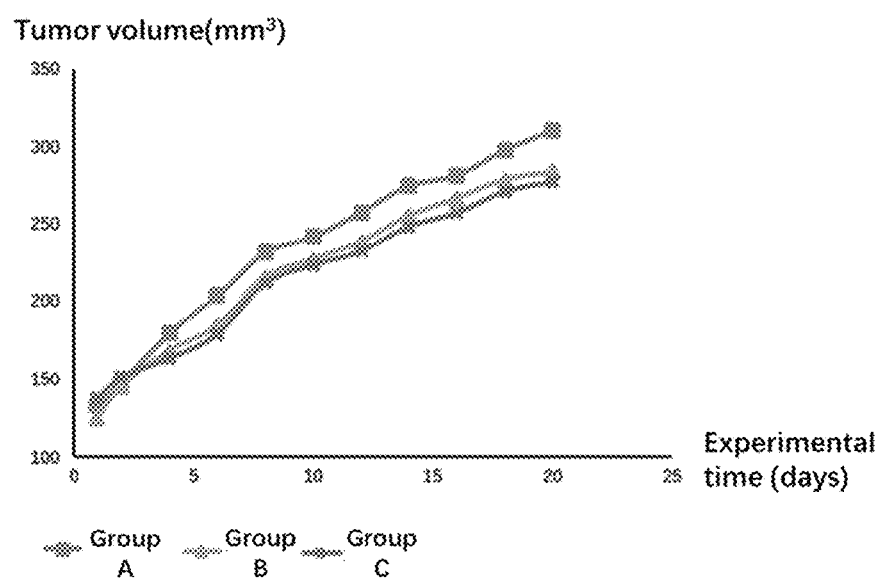
FIG. 19 depicts the effect of tumor volume change in a tumor-bearing rat which is treated with a VEGFR/VEGF inhibitor when the nitric oxide releasing agent of example 143 of the present application is external administered.

The experimental results are shown in FIG. 19. It can be seen from the results in FIG. 19 that in different experimental groups, the tumor volume of the groups administered with ointment (Group B or Group C) is less than the experiment group (Group A), and the tumor volume of Group C is close to or slightly less than the tumor volume of Group B. Thus, it can be seen that the external ointment containing the nitric oxide releasing agent would not reduce the effects of the VEGFR/VEGF inhibitor on tumors.

Examples 144-145: Effect of Nitric Oxide Releasing Agent on Ameliorating Proliferative Toxicity of VEGF/VEGFR Inhibitor to HUVEC, HaCaT Cells and Comparison with Calcium Channel Blockers It has been reported that calcium channel blockers (such as, Diltiazem) may be used to treat the side effect of Hand-Foot Syndrome (HFS) caused by anti-VEGFR multi-kinase inhibitor (see, U.S. Patent Application US2016/0101114A1). However, the therapeutic effect of Diltiazem against HFS caused by anti-VEGFR multi-kinase inhibitors is very limited. In the present application, the effect of the nitric oxide releasing agent is compared with that of calcium channel blockers.

The cultured HUVEC, HaCat cells were digested, suspended, counted and seeded into a 96-well plate with 5000 cells per well. The wells were divided to: the blank control group, the VEGF/VEGFR inhibitor group, the VEGF/VEGFR inhibitor+nitric oxide releasing agent group, the VEGF/VEGFR inhibitor solvent group, the nitric oxide releasing agent solvent control group, the VEGF/VEGFR inhibitor+calcium channel blocker group, and calcium channel blocker solvent control group, wherein each well of each group contained a basic medium, and the final liquid volume contained in each well was about 100 μL. The particular grouping situation was as follows:
 1) the blank control group: no solution was added except normally replacing the medium;
 2) the VEGF/VEGFR inhibitor group: a VEGF/VEGFR inhibitor solution (the final concentration was shown in Table 16, and the solvent of the VEGF/VEGFR inhibitor solution was DMSO);
 3) the VEGF/VEGFR inhibitor+nitric oxide releasing agent group: a VEGF/VEGFR inhibitor solution and a nitric oxide releasing agent solution were added (the final concentrations of the VEGF/VEGFR inhibitor and the nitric oxide releasing agent were shown in Table 16, the solvent of the nitric oxide releasing agent solution was selected as ethanol or sterile water depending on the solubility of the nitric oxide releasing agent, and the slight difference of the total volume of each group was complemented by adding the corresponding solvent as selected);

4) the VEGF/VEGFR inhibitor solvent group: an equal volume of DMSO as contained in the corresponding VEGF/VEGFR inhibitor solution in Group 2) was added;

5) the nitric oxide releasing agent solvent control group: an equal volume of the same type of solvent (e.g., ethanol or sterile water) as contained in the corresponding nitric oxide releasing agent solution in Group 3);

6) the VEGF/VEGFR inhibitor+calcium channel blocker group: a VEGF/VEGFR inhibitor solution was first added, and then a calcium channel blocker solution was added (the final concentrations of the VEGF/VEGFR inhibitor and Sildenafil were shown in Table 16, the solvent of the Sildenafil solution was DMSO, and the slight difference of the total volume of each group was complemented by adding the corresponding solvent as selected);

7) the calcium channel blocker solvent control group: an equal volume of DMSO as contained in the corresponding calcium channel blocker solution in Group 6) was added.

The VEGF/VEGFR inhibitor solvent group was not subject to data processing, and only served as a reference for evaluating the system error of experiments. The nitric oxide releasing agent solvent control group and the calcium channel blocker solvent control group were used for data correction, thereby eliminating the effect of solvents on results.

After cultured for additional 24 hours, the survival rate of cells was determined by Cell Counting Kit-8 (CCK-8) assay kit (C0037, Shanghai Beyotime Biotechnology Inc., Beyotime Biotechnology), to calculate to calculate the amelioration effect of VEGF/VEGFR inhibitor to proliferative toxicity and the ameliorating effect of the nitric oxide releasing agent or calcium channel blocker to the proliferative toxicity. GraphPad Prism 6.0 Software and t-test were used to carry out a statistic analysis of the results and plot a graph.

Figure 20:
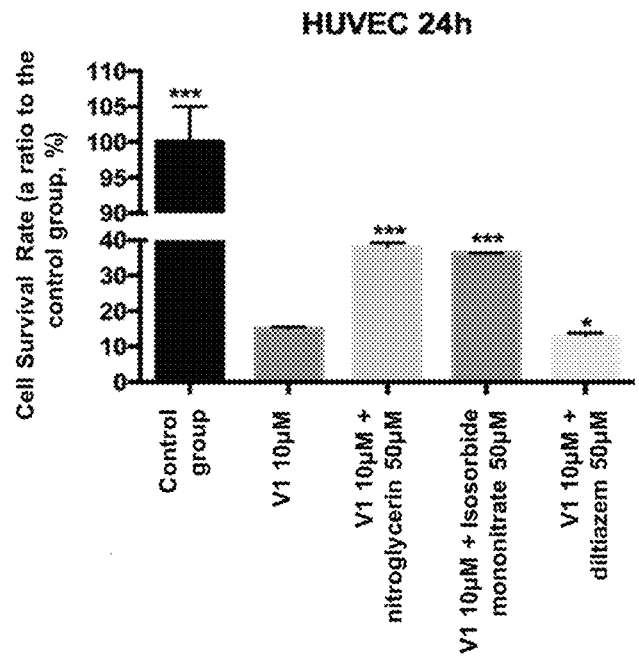
FIG. 20 depicts an exemplary result of cell proliferative toxicity as determined after administration of a nitric oxide releasing agent (or Diltiazem) to HUVEC cells.
Figure 21:
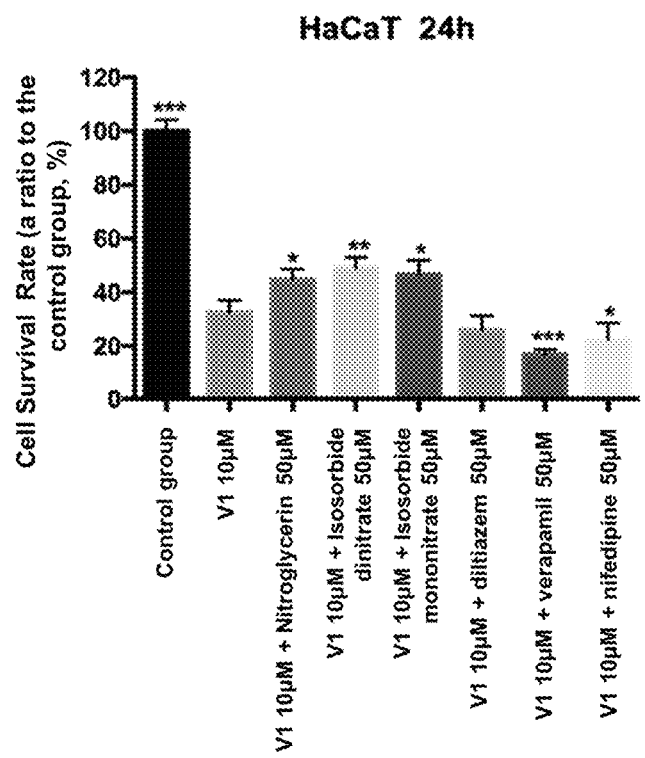
FIG. 21 depicts an exemplary result of cell proliferative toxicity as determined after administration of a nitric oxide releasing agent (or calcium channel blocker) to HaCaT cells.

Table 16 lists various combinations of the VEGF/VEGFR inhibitor with the nitric oxide releasing agent or (calcium channel blocker) and the corresponding experimental results (wherein, the data as listed in the cell survival rate column were the percentages of viable cells increased by the VEGF/VEGFR inhibitor+nitric oxide releasing agent group (or calcium channel blocker), as compared to the VEGF/VEGFR inhibitor group). FIG. 20 represents the exemplary results of cell proliferative toxicity as determined by the CCK-8 method after 24 hours from the administration of the VEGF/VEGFR inhibitor sorafenib tosylate (V1) and the nitric oxide releasing agent (or Diltiazem) to the HUVEC cells, respectively. FIG. 21 represents the exemplary results of cell proliferative toxicity as determined by the CCK-8 method after 24 hours from the administration of the VEGF/VEGFR inhibitor sorafenib tosylate (V1) and the nitric oxide releasing agent (or calcium channel blocker) to the HaCat cells, respectively. Of those, the horizontal axis represents different experiment groups and control groups, and the vertical axis represents the cell survival rate (the survival percentage of other experimental groups or solvent control groups is calculated based on 100% of the cell survival rate of the blank control group). Of those, * represents $P<0.001$; ** represents $P<0.01$; * represents $P<0.05$, indicating that it has significant difference from the corresponding group in which the VEGF/VEGFR inhibitor is administered alone; as statistically detected by using t-test.

TABLE 16

Experimental Conditions and Results of Examples 144-145

| Ex No. | Cell Type | VEGFR inhibitor | Final Concentration | Nitric oxide releasing agent | Final Concentration | Cell Survival Rate |
| --- | --- | --- | --- | --- | --- | --- |
| 144 | HUVEC | Sorafenib (V1) | 10 μM | Nitroglycerin | 50 μM | Increased by 25-50% |
| | | | | Isosorbide Mononitrate | 50 μM | Increased by 20-40% |
| | | | | Diltiazem | 50 μM | Decreased significantly |
| 145 | HaCaT | Sorafenib (V1) | 10 μM | Nitroglycerin | 50 μM | Increased by 20-40% |
| | | | | Isosorbide Dinitrate | 50 μM | Increased by 20-50% |
| | | | | Isosorbide Mononitrate | 50 μM | Increased by 20-50% |
| | | | | Diltiazem Verapamil Nifedipine | 50 μM 50 μM 50 μM | No significant increase or decrease |

Examples 146: Determination of Effect of the Nitric Oxide Releasing Agent (or Calcium Channel Blocker) on Extra-Cellular NO Level Compared effect of the nitric oxide releasing agent with calcium channel blocker on the concentration of extra-cellular NO. The results showed calcium channel blocker was not capable of increasing the concentration of extra-cellular NO, and was not capable of producing NO, therefore calcium channel blocker is not a nitric oxide releasing agent.

The cultured HaCaT cells were digested, suspended, counted, and seeded into a 24-well plate with 200,000 cells per well. After the cells were attached, a nitric oxide releasing agent (or calcium channel blocker) solution was added to achieve a particular final concentration (e.g., as shown in Tables 17). A basic medium was added into the control group. At 24 hours after administration of the nitric oxide releasing agent (or calcium channel blocker), 50 μL of supernatant of each group was collected for detecting the NO level in the extracellular supernatant A NO Assay kit (S0021, Beyotime Inc.) was used for detecting the NO level.

Figure 22:
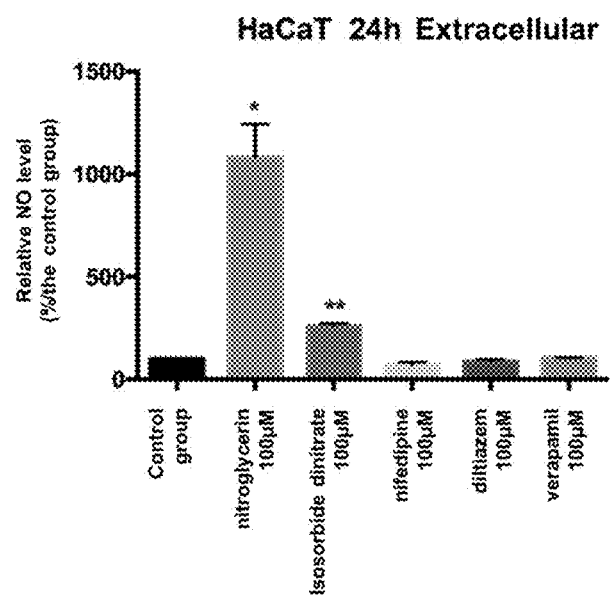
FIG. 22 depicts the relative NO levels after administration of a nitric oxide releasing agent (or calcium channel blocker) to HaCaT cells.

FIG. 22 represents the relative extracellular NO levels in outside HaCaT cells after 24 hours of treatment with the nitric oxide releasing agent (or calcium channel blocker). The control group was the basic medium, reflecting the biological level. Of those, represents P<0.001, ** represents P<0.01, * represents P<0.05, indicating a significant difference as compared with the corresponding control group; as statistically analyzed by using t-test.

TABLE 17

Experimental Conditions and Results of Examples 146

| Ex. No. | Medicament | Final Concentration | Cell Type (Extracellular) | Time Point | NO Level |
|---|---|---|---|---|---|
| 146 | Nitroglycerin | 100 μM | HaCaT | 24 h | Increased by 800-1000% |
|  | Isosorbide Dinitrate | 100 μM |  |  | Increased by 100-300% |
|  | Nifedipine | 100 μM |  |  | No Significant Change |
|  | Diltiazem | 100 μM |  |  |  |
|  | Verapamil | 100 μM |  |  |  |

Example 147: Determination of the Effect of the Nitric Oxide Releasing Agent on Expression Levels of Calmodulin and Calreticulin in HaCat Cell Calmodulin (CaM) is an intermediate calcium-binding messenger protein and an intracellular target of the secondary messenger $Ca^{2+}$ (Chin D and Means A R, 2000). Calmodulin acts as part of a calcium signal transduction pathway and the binding of $Ca^{2+}$ is required for the activation of calmodulin, therefore calmodulins usually act as marker of calcium signal transduction pathway (Berchtold and Villalobo, 2014). The binging between calreticulin (CRT) with $Ca^{2+}$ inactivates it (Michalak M, et al., 2002). In the present application, compared effect of the nitric oxide releasing agent with calcium channel blocker on expression levels of calmodulin and calreticulin in HaCat cell The cultured HaCaT cells were digested, suspended, counted, and seeded into a 6-well plate with 200,000 cells per well. After the cells were attached, a nitric oxide releasing agent (or calcium channel blocker) solution was added to achieve a particular final concentration. A basic medium was added into the control group. At 24 hours after administration of the nitric oxide releasing agent (or calcium channel blocker), RIPA lysate (P0013C, Beyotime Biotechnology) was used to extract protein. The change of expressions of calmodulin and calreticulin was determined by Western Blot.

Figure 23:
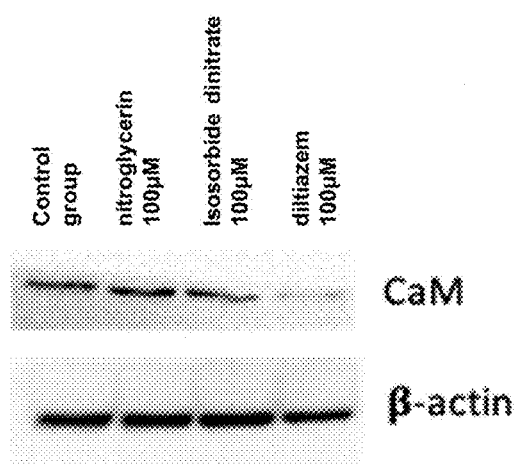
FIG. 23 depicts the expression level of Calmodulin (CaM) after administration of a nitric oxide releasing agent (or calcium channel blocker) to HaCaT cells.
Figure 24:
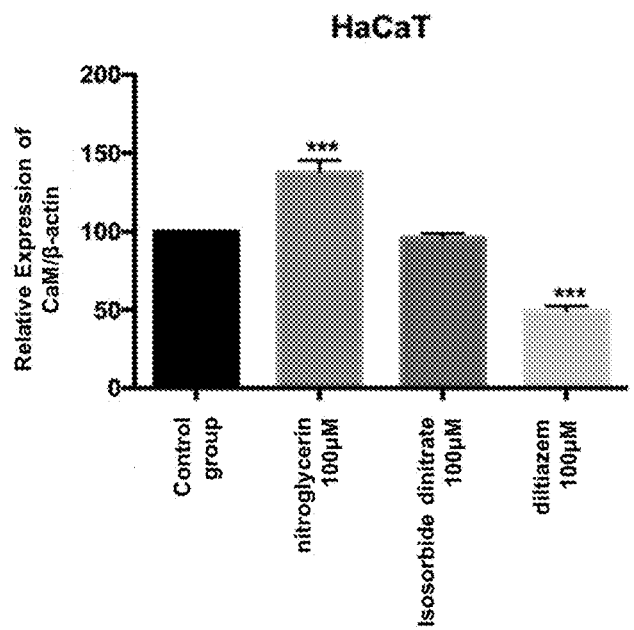
FIG. 24 depicts the result of gray value analysis of the expression level of Calmodulin (CaM) after administration of a nitric oxide releasing agent (or calcium channel blocker) to HaCaT cells.
Figure 25:
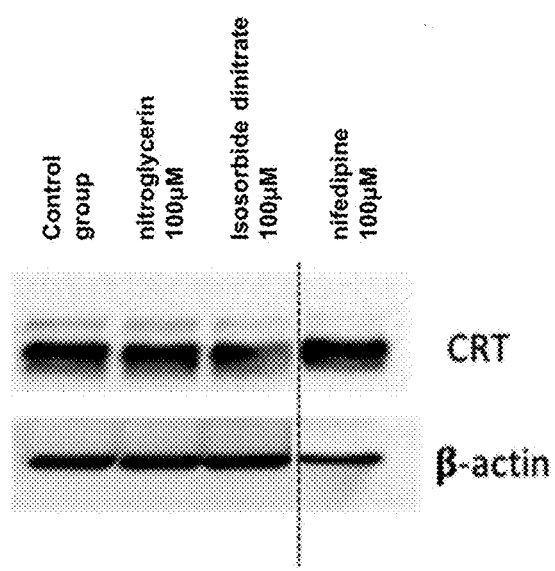
FIG. 25 depicts the expression level of Calreticulin after administration of a nitric oxide releasing agent (or calcium channel blocker) to HaCaT cells.
Figure 26:
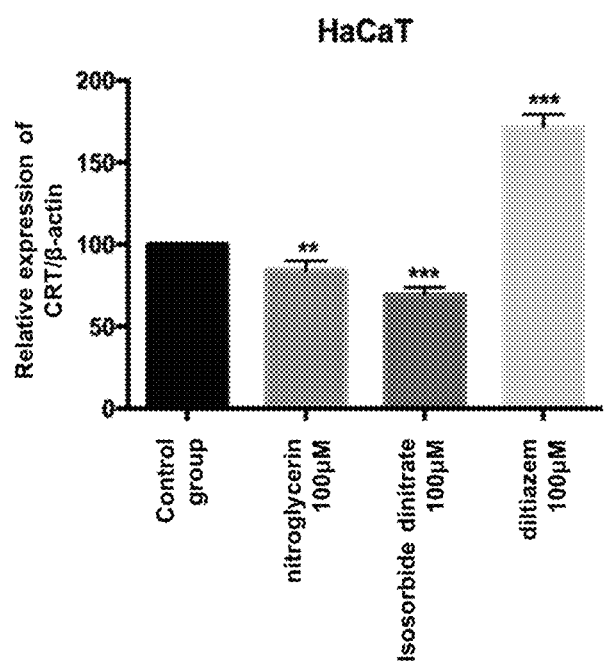
FIG. 26 depicts the result of gray value analysis of the expression level of Calreticulin after administration of a nitric oxide releasing agent (or calcium channel blocker) to HaCaT cells.

FIG. 23 represents the expression level of calmodulin (CaM) in HaCaT cells after 24 hours of treatment with the nitric oxide releasing agent (or calcium channel blocker). FIG. 24 represents the result of gray value analysis of relative expression of calmodulin. FIG. 25 represents the expression level of calreticulin (CRT) in HaCaT cells after 24 hours of treatment with the nitric oxide releasing agent (or calcium channel blocker). FIG. 26 represents the result of gray value analysis of relative expression of calreticulin.

Image Lab was used to analyze the gray value results. GraphPad Prism 6.0 Software and t-test were used to carry out a statistic analysis of the results and plot a graph. Of those, represents P<0.001, ** represents P<0.01, * represents P<0.05, indicating a significant difference as compared with the corresponding control group; as statistically analyzed by using t-test.

It can be seen from the results in FIGS. 23-24 that compared with the control group, the calmodulin of the nitric oxide releasing agent group had no significant change, while the calmodulin of calcium channel blocker diltiazem group decreased significantly. The results in FIGS. 25-26 show that compared with the control group, the calreticulin of the nitric oxide releasing agent group reduced slightly, while the expression of calreticulin of calcium channel blocker nifedipine group increased significantly. Therefore, the nitric oxide releasing agent doesn't belong to calcium channel blocker.

Examples 148-159: Comparison of 0.2% Nitroglycerin Ointment and Other Nitric Oxide Releasing Agents with Calcium Channel Blocker in the Experiments of Preventing the Hand-Foot Syndrome Caused by the Small Molecular VEGFR/VEGF Inhibitors Rats (about 200 g) were fed for one week, divided to groups (each of which comprised 10 rats), and then subjected to gavage administration experiments. A VEGFR/VEGF inhibitor was dissolved in a mixed solution having a ratio of Cremophor EL:ethanol=1:1, and diluted with PBS to the desired concentration (about 3 times diluted with a PBS solution) prior to gavage. The gavage amount was not more than 2 mL, and the dosage was shown in Table 18. After gavage, the left paw (palm and gaps of paw) of the rat was topically administered with nitroglycerin ointment (or other nitric oxide releasing agents) (about 0.05 g), and the right paw was topically administered with calcium channel blocker ointment in the same manner. After administration, the rat was fixed by a fixed cylinder for about 4 hours. After 4 hours, the rat was released, wiped with water to remove the residual medicament on the administered site, and returned to the cage. The gavage frequency of the VEGFR/VEGF inhibitors is shown in Table 18. The rat was subject to gavage with the VEGFR/VEGF inhibitors, until the paw administered with calcium channel blocker ointment developed the symptoms of hand-foot syndrome or the rat died. After 15-18 days of administration, the number of rats in which the paw administered with nitroglycerin ointment (or the other nitric oxide releasing agent) exhibited normal or significantly less serious than the paw administered with the calcium channel blocker ointment was counted as the number of rats in which the hand-foot syndrome was effectively prevented.

Table 18 lists the combination of experiments of 0.2% nitroglycerin ointments (or the other nitric oxide releasing agent) and calcium channel blocker ointment, and the corresponding experimental results (wherein, the value in the relative ameliorated rate column=the number of rats in which the hand-foot syndrome on the left paw was significantly less serious than the hand-foot syndrome on the right paw in each group/the hand-foot syndrome model in each group×100%).

TABLE 18

Experimental Conditions and Results of Examples 148-159

| Experiment No. | VEGFR inhibitor | Dosage | Frequency | Administration Left | Administration Right | Administration Days | Relative Ameliorated Rate |
|---|---|---|---|---|---|---|---|
| 148 | Sorafenib | 80 mg/kg | once per day | 0.2% Nitroglycerin ointment | 0.2% Diltiazem ointment | 15 | 83.33% |
| 149 | Apatinib | 105 mg/kg | once per day | 0.2% Nitroglycerin ointment | 0.2% Diltiazem ointment | 15 | 60% |
| 150 | Lenvatinib | 100 mg/kg | twice per day | 0.2% Nitroglycerin ointment | 0.2% Diltiazem ointment | 18 | 77.78% |
| 151 | Regorafenib | 90 mg/kg | once per day | 0.2% Nitroglycerin ointment | 0.2% Diltiazem ointment | 18 | 75% |
| 152 | Sorafenib | 80 mg/kg | once per day | 0.2% Nitroglycerin ointment | 0.2% Verapamil ointment | 15 | 71.43% |
| 153 | Sorafenib | 80 mg/kg | once per day | 0.2% Nitroglycerin ointment | 0.2% Nifedipine ointment | 15 | 66.67% |
| 154 | Sorafenib | 80 mg/kg | once per day | 0.2% Isosorbide dinitrate and isosorbide mononitrate mixed ointment | 0.2% Diltiazem ointment | 15 | 60% |
| 155 | Sorafenib | 80 mg/kg | once per day | 0.2% Isosorbide dinitrate and isosorbide mononitrate mixed ointment | 0.2% Nifedipine ointment | 15 | 66.67% |
| 156 | Sorafenib | 80 mg/kg | once per day | 0.2% Isosorbide dinitrate and isosorbide mononitrate mixed ointment | 0.2% Nifedipine ointment | 15 | 60% |
| 157 | Sorafenib | 80 mg/kg | once per day | 0.2% Nicorandil ointment | 0.2% Diltiazem ointment | 15 | 66.67% |
| 158 | Sorafenib | 80 mg/kg | once per day | 0.2% Nicorandil ointment | 0.2% Verapamil ointment | 15 | 57.14% |
| 159 | Sorafenib | 80 mg/kg | once per day | 0.2% Nicorandil ointment | 0.2% Nifedipine ointment | 15 | 62.5% |

NOTE:
The modelling success rate of anti-cancer medicaments are not constant: the success rate of the hand-foot syndrome model in each group is 30% to 90%, that is, there are about 3-9 successful hand-foot syndrome models among 10 rats, during the modelling process, death of individual rat or unsuccessful modelling in different administration groups. The control rate refers to the ratio of the number of rats in which the symptoms on the paw administered with nitroglycerin ointment are less serious than the paw administered with other medicaments to the total number of the hand-foot syndrome model rats in the experimental groups.

Figure 27:
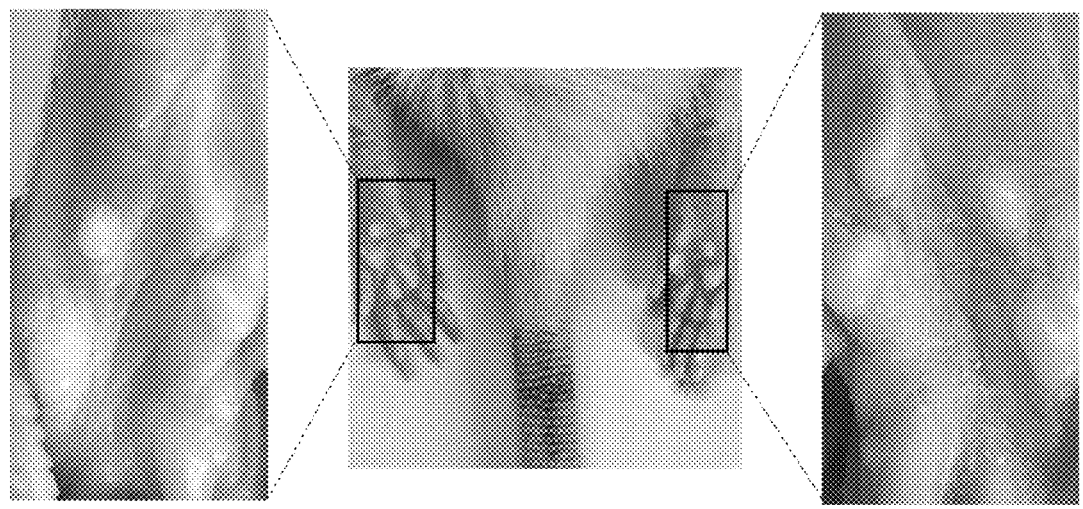
FIG. 27 depicts the photographs of left paw, front side, and right paw of a typical rat (administrated to the left paw and right paw) in the administration groups of examples 148-153 of the present application.
Figure 28:
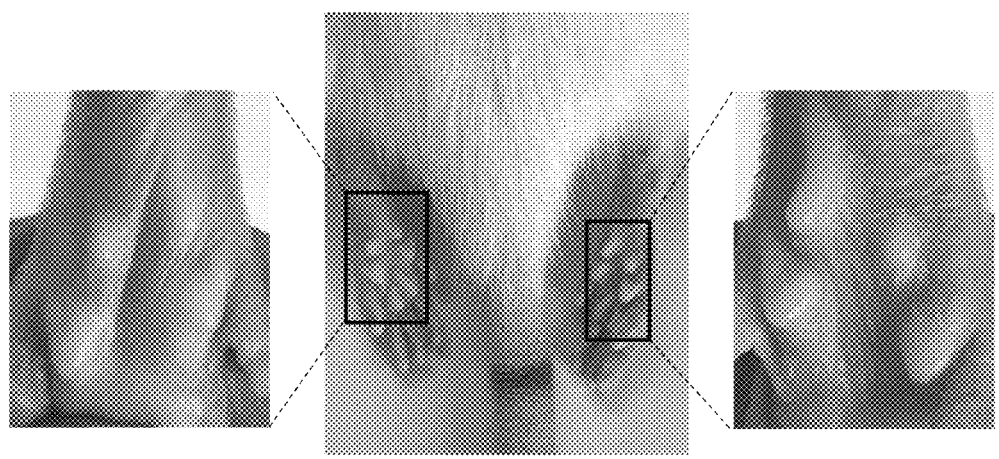
FIG. 28 depicts the photographs of left paw, front side, and right paw of a typical rat (administrated to the left paw and right paw) in the administration groups of examples 154 of the present application.

FIG. 27 shows the conditions of the left paw, front side, and right paw of a typical rat in the administration groups of examples 148-153 after it was topically administered on its left paw (with 0.2% Nitroglycerin ointment) and on its right paw (with 0.2% Diltiazem ointment). FIG. 28 shows the conditions of the left paw, front side, and right paws of a typical rat in the administration group of examples 154 after it was administered on its left paw (0.2% Isosorbide dinitrate and isosorbide mononitrate mixed ointment) and on its right paw (0.2% Diltiazem ointment).

It can be seen from the results in Table 18 and FIG. 27 that as compared with 0.2% calcium channel blocker ointment, 0.2% nitroglycerin ointment and other nitric oxide releasing agent are capable of effectively controlling the hand-foot syndrome caused by the VEGFR/VEGF inhibitor.

Preferred embodiments of the present application are described herein, including the best mode known by the inventors for carrying out the application. Upon reading of the description, variations of those preferred embodiments will be apparent to those of ordinary skill in the art. The inventors expect that the skilled person can apply such variants if required, and the inventors intend to implement the present application in a manner other than those specifically described herein. Thus, the present application includes all the modifications and equivalents of the subject matter described in the appended claims as permitted by applicable laws. Moreover, the present application includes any combination of all possible variations of the aforesaid elements, unless otherwise indicated or clearly contradict with the context.

The invention claimed is:

1. A method for preventing or treating VEGF-inhibition and/or VEGFR-inhibition associated hand-foot syndrome in a subject, comprising administering to the subject a medicament comprising an effective amount of a nitric oxide releasing agent, wherein said VEGF-inhibition and/or VEGFR-inhibition is associated with an administration of a VEGF inhibitor and/or a VEGFR inhibitor to said subject.

2. The method of claim 1, wherein said nitric oxide releasing agent comprises nitroglycerin, isosorbide mononitrate and/or isosorbide dinitrate.

3. The method of claim 1, wherein said medicament is administered topically.

4. The method of claim 2, wherein said medicament is an ointment, lotion, or cream.

5. The method of claim 2, wherein said nitric oxide releasing agent is present in said medicament at a concentration of from about 0.01% (w/w) to about 1% (w/w).

6. The method of claim 2, wherein said nitric oxide releasing agent is nitroglycerin.

7. The method of claim 2, wherein said nitric oxide releasing agent is isosorbide mononitrate.

8. The method of claim 2, wherein said nitric oxide releasing agent is isosorbide dinitrate.

9. The method of claim 1, wherein said subject is a cancer patient on a VEGF inhibitor and/or VEGFR inhibitor treatment.

10. The method of claim 1, wherein said VEGF inhibitor and/or VEGFR inhibitor comprises Ramucirumab, Bevacizumab, Regorafenib, Ponatinib, Cabozantinib, Lenvatinib, Sorafenib, Pazopanib, Apatinib, Axitinib, Nintedanib, Vandetanib, Sunitinib, Midostaurin, Tivozanib, Fruquintinib, Cediranib, Brivanib, Donafenib, Sulfatinib, Anlotinib, Famitinib, Tesevatinib, Vorolanib, Motesanib, Linifanib, Semaxanib, Dovitinib, Orantinib, Vatalanib, Telatinib, Glesatinib, Delitinib, Ilorasertib, Rebastinib, Golvatinib, Foretinib, Ningetinib, Tafetinib, Altiratinib, TAS-115, Chiauranib, Henatinib, 4SC-203, AAL-993, ACTB-1003, AEE-788, AMG-628, Arenobufagin, BAW2881, BIBF-1202, BMS-690514, BMS-794833, CEP-11981, CEP-5214, CP-547632, CYC116, DW532, ENMD-2076, FIIN-1, GFB-204, BFH-772, BMS599626, BMS690514, PP 121, MGCD 265 analogue, AC480, Ki 8751, KRN 633, WHI-P 154, TAK593, JI 101, AZD-2932, SCR-1481B1, Isoliquiritigenin, JNJ-26483327, KI-20227, LY2457546, ODM-203, OSI-930, PF-00337210, CGP41231, R1530, RAF265, SAR131675, Semaxinib, SIM010603, SKLB1002, SKLB610, SU 5205, SU11652, SU14813, SU-1498, SU-4312, SU5402, T-1840383, Tanshinone IIA, TAS-115, TG 100572, TG 100801, TG100572 HCl, Toceranib, Tyrosine phosphorylation inhibitor A9, Tesevatinib, XL-844, XL999, ZD4190 HCl, ZM-306416, ZM323881 HCl, ABT-510, NVP-ACC789, ADT-OH, BMS-645737, EG 00229, XL-820, SGI-7079, Endostatin, Taxifolin, Aflibercept, a pharmaceutically acceptable salt thereof and/or any combination of the foregoing.

11. A method for preventing or treating a VEGF-inhibition and/or VEGFR-inhibition associated epithelial disease or disorder in a subject, comprising administering to the subject an effective amount of a nitric oxide releasing agent for preventing or treating the disease or disorder, wherein said VEGF-inhibition and/or VEGFR-inhibition is associated with an administration of a VEGF inhibitor and/or a VEGFR inhibitor to said subject.

12. The method of claim 11, wherein said VEGF inhibitor and/or VEGFR inhibitor comprises Ramucirumab, Bevacizumab, Regorafenib, Ponatinib, Cabozantinib, Lenvatinib, Sorafenib, Pazopanib, Apatinib, Axitinib, Nintedanib, Vandetanib, Sunitinib, Midostaurin, Tivozanib, Fruquintinib, Cediranib, Brivanib, Donafenib, Sulfatinib, Anlotinib, Famitinib, Tesevatinib, Vorolanib, Motesanib, Linifanib, Semaxanib, Dovitinib, Orantinib, Vatalanib, Telatinib, Glesatinib, Delitinib, Ilorasertib, Rebastinib, Golvatinib, Foretinib, Ningetinib, Tafetinib, Altiratinib, TAS-115, Chiauranib, Henatinib, 4SC-203, AAL-993, ACTB-1003, AEE-788, AMG-628, Arenobufagin, BAW2881, BIBF-1202, BMS-690514, BMS-794833, CEP-11981, CEP-5214, CP-547632, CYC116, DW532, ENMD-2076, FIIN-1, GFB-204, BFH-772, BMS599626, BMS690514, PP 121, MGCD 265 analogue, AC480, Ki 8751, KRN 633, WHI-P 154, TAK593, JI 101, AZD-2932, SCR-1481B1, Isoliquiritigenin, JNJ-26483327, KI-20227, LY2457546, ODM-203, OSI-930, PF-00337210, CGP41231, R1530, RAF265, SAR131675, Semaxinib, SIM010603, SKLB1002, SKLB610, SU 5205, SU11652, SU14813, SU-1498, SU-4312, SU5402, T-1840383, Tanshinone IIA, TAS-115, TG 100572, TG 100801, TG100572 HCl, Toceranib, Tyrosine phosphorylation inhibitor A9, Tesevatinib, XL-844, XL999, ZD4190 HCl, ZM-306416, ZM323881 HCl, ABT-510, NVP-ACC789, ADT-OH, BMS-645737, EG 00229, XL-820, SGI-7079, Endostatin, Taxifolin, Aflibercept, a pharmaceutically acceptable salt thereof and/or any combination of the foregoing.

13. The method of claim 11, wherein said epithelial disease or disorder comprises VEGF-inhibition and/or VEGFR-inhibition associated rash, VEGF-inhibition and/or VEGFR-inhibition associated hand-foot syndrome, VEGF-inhibition and/or VEGFR-inhibition associated pruritus, VEGF-inhibition and/or VEGFR-inhibition associated erythema, VEGF-inhibition and/or VEGFR-inhibition associated xerosis cutis, VEGF-inhibition and/or VEGFR-inhibition associated alopecia, VEGF-inhibition and/or VEGFR-inhibition associated paronychia, VEGF-inhibition and/or VEGFR-inhibition associated pigmentation disorder, VEGF-inhibition and/or VEGFR-inhibition associated oral mucositis, VEGF-inhibition and/or VEGFR-inhibition associated xerostomia, VEGF-inhibition and/or VEGFR-inhibition associated epistaxis, VEGF-inhibition and/or VEGFR-inhibition associated nasopharyngitis, VEGF-inhibition and/or VEGFR-inhibition associated cheilitis, VEGF-inhibition and/or VEGFR-inhibition associated esophagitis, VEGF-inhibition and/or VEGFR-inhibition associated esogastritis, VEGF-inhibition and/or VEGFR-inhibition associated gastric ulcer, VEGF-inhibition and/or VEGFR-inhibition associated diarrhea, VEGF-inhibition and/or VEGFR-inhibition associated vomiting, VEGF-inhibition and/or VEGFR-inhibition associated nausea, VEGF-inhibition and/or VEGFR-inhibition associated anorexia, VEGF-inhibition and/or VEGFR-inhibition associated constipation, and/or VEGF-inhibition and/or VEGFR-inhibition associated abdominal pain.

14. The method of claim 11, wherein said epithelial disease or disorder comprises VEGF-inhibition and/or VEGFR-inhibition associated hand-foot syndrome.

15. The method of claim 11, wherein said nitric oxide releasing agent is nitroglycerin, isosorbide mononitrate, and/or isosorbide dinitrate.

16. The method of claim 11, wherein said nitric oxide releasing agent is administered topically.

17. The method of claim 16, wherein said nitric oxide releasing agent is topically administered at a site that is not the occurrence site of cancer or potential metastatic site of cancer.

18. The method of claim 16, wherein said nitric oxide releasing agent is formulated into an ointment, lotion, or cream.

19. The method of claim 11, wherein said subject is a cancer patient on a VEGF inhibitor and/or VEGFR inhibitor treatment.

20. The method of claim 11, wherein said nitric oxide releasing agent is administered at a concentration of from about 0.01% (w/w) to about 1% (w/w).

21. The method of claim 1, wherein said nitric oxide releasing agent is present in said medicament at a concentration of from about 0.05% (w/w) to about 1% (w/w).

22. The method of claim 4, wherein said nitric oxide releasing agent is present in said medicament at a concentration of from about 0.05% (w/w) to about 1% (w/w).

23. The method of claim 6, wherein said nitric oxide releasing agent is present in said medicament at a concentration of from about 0.05% (w/w) to about 1% (w/w).

24. The method of claim 23, wherein said medicament is an ointment, lotion, or cream.

25. The method of claim 9, wherein said nitric oxide releasing agent is nitroglycerin.

26. The method of claim 25, wherein said nitric oxide releasing agent is present in said medicament at a concentration of from about 0.05% (w/w) to about 1% (w/w).

27. The method of claim 26, wherein said medicament is an ointment, lotion, or cream.

28. The method of claim 27, wherein said nitric oxide releasing agent is present in said medicament at a concentration of about 0.2% (w/w).

29. The method of claim 27, wherein said nitric oxide releasing agent is present in said medicament at a concentration of about 0.5% (w/w).

30. The method of claim 27, wherein said nitric oxide releasing agent is present in said medicament at a concentration of from about 1% (w/w).

* * * * *